US011473148B2

(12) United States Patent
Feber et al.

(10) Patent No.: US 11,473,148 B2
(45) Date of Patent: Oct. 18, 2022

(54) METHODS OF DIAGNOSING BLADDER CANCER

(71) Applicant: UCL Business PLC, London (GB)

(72) Inventors: Andrew Feber, London (GB); John Kelly, London (GB)

(73) Assignee: UCL Business PLC

( * ) Notice: Subject to any disclaimer, the term of this patent is extended or adjusted under 35 U.S.C. 154(b) by 296 days.

(21) Appl. No.: 15/738,539

(22) PCT Filed: Jun. 24, 2016

(86) PCT No.: PCT/GB2016/051903
§ 371 (c)(1),
(2) Date: Dec. 20, 2017

(87) PCT Pub. No.: WO2016/207656
PCT Pub. Date: Dec. 29, 2016

(65) Prior Publication Data

US 2018/0305765 A1 Oct. 25, 2018

(30) Foreign Application Priority Data

Jun. 24, 2015 (GB) ..................................... 1511152

(51) Int. Cl.
*C12Q 1/6886* (2018.01)
*C12Q 1/686* (2018.01)
*C12Q 1/6827* (2018.01)
*C12Q 1/6858* (2018.01)
*G01N 33/574* (2006.01)

(52) U.S. Cl.
CPC ........... *C12Q 1/6886* (2013.01); *C12Q 1/686* (2013.01); *C12Q 1/6827* (2013.01); *C12Q 1/6858* (2013.01); *C12Q 2523/125* (2013.01); *C12Q 2600/118* (2013.01); *C12Q 2600/154* (2013.01); *C12Q 2600/16* (2013.01); *G01N 33/57407* (2013.01)

(58) Field of Classification Search
CPC ........................ C12Q 1/6886; C12Q 2600/154
See application file for complete search history.

(56) References Cited

U.S. PATENT DOCUMENTS

2013/0224738 A1 8/2013 Scher et al.

FOREIGN PATENT DOCUMENTS

WO 2010/123354 A2 10/2010
WO 2010/149782 A1 12/2010
WO 2014/042763 A1 3/2014

OTHER PUBLICATIONS

Reinert, T. Advances in Urology, vol. 2012, Article ID 503271, 11 pages. (Year: 2012).*

Schlake et al., "NMP-22, urinary cytology, and cystoscopy: a 1 year comparison study", (2012) Can J Urol. 19:6345-6350.

Siegel et al., "Cancer Statistics, 2011 The Impact of Eliminating Socioeconomic and Racial Disparities on Premature Cancer Deaths", (2011) CA Cancer J Clin. 61:212-236.

Singal et al., "Microsoft® Word™ Macro for Analysis of Cytosine Methylation by the BisulfiteDeamination Reaction", (2001) Biotechniques 30: 116-120.

Su et al., "A Panel of Three Markers Hyper- and Hypomethylated in Urine Sediments Accurately Predicts Bladder Cancer Recurrence",(2014) Clin Cancer Res. 20:1978-1989.

Teschendorff et al., "A beta-mixture quantile normalization method for correctingprobe design bias in Illumina Infinium 450 k DNA methylation data", (2013) Bioinformatics. 29:189-196.

Tewhey et al., "Microdroplet-based PCR amplification for large scale targeted sequencing", (2009) Nat Biotechnol. 27:1025-1031.

Tilki et al., "Urine Markers for Detection and Surveillance of Non-Muscle-Invasive Bladder Cancer", (2011) Eur Urol. 60:484-492.

Van Rhijn et al., "UrineMarkers for Bladder Cancer Surveillance: ASystematic Review", (2005) Eur Urol. 47:736-748.

Venkatesan et al., "Positive Predictive Value of Specific Mammographic Findings according to Reader and Patient Variables", (2009) Radiology. 250:648-657.

Wolff et al., "Unique DNA methylation patterns distinguish non-invasive and invasive urothelial cancers and establish an epigenetic field defect in premalignant tissue", (2010) Cancer Res. 70:8169-8178.

Xiong & Laird, "COBRA: a sensitive and quantitative DNA methylation assay", (1997) Nucleic Acids Res. 25:2532-2534.

Yu et al., "A Novel Set of DNA MethylationMarkers in Urine Sediments for Sensitive/Specific Detection of Bladder Cancer", (2007) Clin Cancer Res. 13:7296-7304.

Zaak et al., "Endoscopic Detection of Transitional Cell Carcinoma With 5-Aminolevulinic Acid: Results of 1012 Fluorescence Endoscopies", (2001) Urology. 57:690-694.

Kim et al., "HOXA9, ISL1 and ALDH1A3 methylation patterns as prognostic markers for nonmuscle invasive bladder cancer: Array-based DNA methylation and expression profiling", (2013) International Journal of Cancer. 133:1135-1142.

Kandimalla et al., "Genome-wide Analysis of CpG Island Methylation in BladderCancer Identified TBX2, TBX3, GATA2, and ZIC4 as pTa-Specific Prognostic Markers", (2012) European Urology. 61: 1245-1256.

(Continued)

*Primary Examiner* — Diana B Johannsen
(74) *Attorney, Agent, or Firm* — Norton Rose Fulbright US LLP

(57) ABSTRACT

The present invention relates to methods of diagnosing bladder cancer in a patient, involving determining the methylation status of Methylation Variable Positions (MVPs) in DNA from the patient and providing a diagnosis based on methylation status data. The invention also relates to methods of treating bladder cancer comprising providing a diagnosis of bladder cancer by the diagnostic methods defined herein followed by administering one or more anti-cancer agents to a patient. The invention also relates to methylation-discriminatory arrays comprising probes directed to the MVPs defined herein and kits comprising the arrays.

20 Claims, 12 Drawing Sheets

Specification includes a Sequence Listing.

(56) References Cited

OTHER PUBLICATIONS

Beukers et al., "The Use of Molecular Analyses in Voided Urine for the Assessment of Patients with Hematuria", (2013) PloS One. 8: e77657.
Chen, Pi-Che et al.,"Distinct DNA methylation epigenotypes in bladder cancer from different Chinese sup-populations and its implication in cancer detection using voided urine", (2011) BMC Medical Genomics. 4: 45.
Feber et al. "Using high-density DNA methyl at ion arrays to profile copy number alterations", Genome Biology, vol. 15, No. 2, Feb. 3, 2014 (Feb. 3, 2014), page R30, Biomed Central Ltd., London, GB.
Reinert et al. "Comprehensive Genome Methylation Analysis in Bladder Cancer: Identification and Validation of Novel Methylated Genes and Application of These as Urinary Tumor Markers", Clinical Cancer Research, vol. 17, No. 17, Jul. 25, 2011 (Jul. 25, 2011), pp. 5582-5592.
Chihara et al. "Diagnostic markers of urothelial cancer based on DNA methylation analysis" BMC Cancer, Biomed Central, vol. 13, No. I, Jun. 4, 2013 (Jun. 4, 2013), p. 275, London, GB.
Anbazhagan et al., "Spreadsheet-Based Program for the Analysis of DNA Methylation" Biotechniques, (2001) 30: 110-114.
Andersson et al., "Filtration Device for On-Site Collection, Storage and Shipment of Cells from Urine and Its Application to DNA-Based Detection of Bladder Cancer" PLoS One, (2014) 9:e94023.
Aronesty, E. "Comparison of Sequencing Utility Programs" The Open Bioinformatics Journal. (2013) 7: 1-8.
Belinsky et al., "Gene-Promoter Hypermethylation as a Biomarker in Lung Cancer" Nat Rev Cancer, (2004) 4:707-717.
Beukers et al., "Hypermethylation of the Polycomb Group Target Gene PCDH7 in Bladder Tumors from Patients of All Ages" (2013) J Urol. 190:311-316.
Blick et al., "Evaluation of diagnostic strategies for bladder cancer using computed tomography (CT) urography, flexible cystoscopy and voided urine cytology: results for 778 patients from a hospital haematuria clinic" (2012) BJU Int. 110:84-94.
Burke et al., "The community-based morbidity of flexible cystoscopy" (2002) BJU Int. 89:347-349.
Burns et al., "APOBEC3B is an enzymatic source of mutation in breast cancer" (2013) Nature. 494:366-370.
Butcher et al., "Probe Lasso: A novel method to rope in differentially methylated regions with 450K DNA methylation data", (2015) Methods. 72:21-28.
Campan et al., "Genome-Scale Screen for DNA Methylation-Based Detection Markers for Ovarian Cancer", (2011) PLoS One. 6:e28141.
Catalona et al., "Measurement of Prostate-Specific Antigen in Srum as a Screening Test for Prostate Cancer" (1991) N Engl J Med. 324:1156-1161.
Cha et al., "Accurate Risk Assessment of Patients with Asymptomatic Hematuria for the Presence of Bladder Cancer", (2012) World J Urol. 30:847-852.
Chung et al., "Detection of Bladder Cancer Using Novel DNA Methylation Biomarkers in Urine Sediments", (2011) Cancer Epidemiol Biomarkers Prev. 20:1483-1491.
Deaton et al., "Cell type-specific DNA methylation at intragenic CpG islands in the immune system", (2011) Genome Res. 21:1074-1086.
Denzinger et al., "Clinically Relevant Reduction in Risk of Recurrence of Superficial Bladder Cancer Using 5-Aminolevulinic Acid-Induced Fluorescence Diagnosis: 8-Year Results of Prospective Randomized Study", (2007) Urology. 69:675-679.
Eng, J. "Receiver Operating Characteristic Analysis: A Primer1", (2005) Academic Radiology .12(7): 909-916.
Fackler et al., "Novel Methylated Biomarkers and a Robust Assay to Detect Circulating Tumor DNA in Metastatic Breast Cancer", (2014). Cancer Res. 74:2160-2170.
Friedrich et al., "Detection of Methylated Apoptosis-Associated Genes in Urine Sediments of Bladder Cancer Patients", (2004) Clin Cancer Res 440. 10:7457-7465.
Frommer et al., "A genomic sequencing protocol that yields a positive display of 5-methylcytosine residues in individual DNA strands" (1992) Proc. Natl Acad. Sci. USA. 89: 1827-1831.
Gerlinger et al., "Intratumour Heterogeneity in Urologic Cancers: From Molecular Evidence to Clinical Implications", (2015) Eur Urol. 67: 729-737.
Gonzalgo et al., "Rapid quantitation of methylation differences at specific sites using methylation-sensitive single nucleotide primer extension (Ms-SNuPE)", (1997) Nucleic Acids Res. 25: 2529-2531.
Guilhamon et al., "Meta-analysis of IDH-mutant cancers identifiesEBF1 as an interaction partner for TET2", (2013) Nat Commun. 4:2166.
Hajdinjak et al., "UroVysion FISH test for detecting urothelial cancers: Meta-analysis ofdiagnostic accuracy and comparison with urinary cytology testing", (2008) Urol Oncol. 26:646-651.
Herman et al., "Methylation-specific PCR: A novel PCR assay for methylation status of CpG islands", (1996) Proc. Natl Acad. Sci. USA. 93: 9821-9826.
Hoffman et al., "Prostate-specific antigen testing accuracy in community practice", (2002) BMC Fam Pract. 3:19.
Hoffmann et al., "MdR1 and ERCC1 Expression Predict Outcome of Patients with Locally Advanced Bladder Cancer Receiving Adjuvant Chemotherapy", (2010) Neoplasia. 12:628-636.
Hoque et al., "Quantitation of Promoter Methylation of Multiple Genes in Urine DNA and Bladder Cancer Detection", (2006) J Natl Cancer Inst. 98:996-1004.
Hoque et al., "Genome-Wide Promoter Analysis Uncovers Portions of the Cancer Methylome", (2008) Cancer Res. 68:2661-2670.
Jemal et al., "Cancer Statistics, 2009", (2009) CA Cancer J Clin. 59:225-249.
Kandimalla et al., "A 3-Plex Methylation Assay Combined with the FGFR3 Mutation Assay Sensitively Detects Recurrent Bladder Cancer in Voided Urine", (2013) Clin Cancer Res. 19:4760-4769.
Kandimalla et al.,"DNA methylation-based biomarkers in bladder cancer", (2013) Nat Rev Urol.
Kelly et al., "Assessment and management of non-visible haematuria in primary care", (2009) BMJ. 338:a3021.
Khadra et al., "A Prospective Analysis of 1,930 Patients With Hematuria Toevaluate Current Diagnostic Practice", (2000) J Urol. 163:524-527.
Komori et al., "Application of microdroplet PCR for large-scale targeted bisulfite sequencing", (2011) Genome Res. 21:1738-1745.
Krueger & Andrews, "Bismark: a flexible aligner and methylation caller for Bisulfite-Seq applications", (2011) Bioinformatics. 27(11):1571-2.
Kulis & Esteller, "DNA Methylation and Cancer", (2010) Adv Genet. 70:27-56. 469.
Leng et al., "Defining a Gene Promoter Methylation Signature in Sputum for Lung Cancer Risk Assessment", (2012) Clin Cancer Res. 18:3387-3395.
Li et al., "MethPrimer: designing primers for methylation PCRs", (2002) Bioinformatics. 18: 1427-1431.
Lotan et al., "Sensitivity and Specificity of Commonly Available Bladder Tumor Markers Versus Cytology: Results of a Comprehensive Literature Review and Meta-Analyses", (2003) Urology. 61:109-118; discussion 118.
Lowe et al., "Marmal-aid—a database for Infinium HumanMethylation450", (2013) BMC Bioinformatics. 14:359.
Lyratzopoulos et al., "Gender inequalities in the promptness of diagnosis of bladder and renal cancer after symptomatic presentation: evidence from secondary analysis of anEnglish primary care audit survey", (2013) BMJ Open. 3.
Mandel et al., "The Effect of Fecal Occult-Blood Screening On the Incidence of Colorectal Cancer", (2000) N Engl J Med. 343:1603-1607.
Morris et al., "ChAMP: 450k Chip Analysis Methylation Pipeline", (2013) Bioinformatics.
Morris et al., "ChAMP: 450k Chip Analysis Methylation Pipeline", (2014) Bioinformatics. 30:428-430.
Olkhov-Mitsel et al., (2012) Cancer Medicine. 1(2): 237-260.
Paul et al., "Assessment of RainDrop BS-seq as a method for large-scale, targeted bisulfite sequencing", (2014) Epigenetics. 9. 678-684.

(56) References Cited

OTHER PUBLICATIONS

Philipp et al., "Prognostic role of methylated free circulating DNA in colorectal cancer", (2012) Int J Cancer. 131:2308-2319.
Atul Kumar, et al; "Comparison of NMP22 BladderChekTest and Urine Cytology for the Detection of Recurrent Bladder Cancer"; Jpn J. Clin Oncol 2006:36(3); 172-175.
Kirsten L. Greene, et al; "Diagnostic Utility of the ImmunoCyt/uCyt+ Test in Bladder Cancer"; 2006 MedReviews, LLC; Reviews in Urology; col. 8, No. 4; pp. 190-197.
Michelle D. Reid-Nicholson, et al; "The Use of Urovysion Fluorescence in situ Hybridization in the Diagnosis and Surveillance of Non-Urothelial Carcinoma of the Bladder"; Modern Pathology (2009) 22; 119-127.
Ainel Aleman, et al; "Identification of PMF1 Methylation in Association with Bladder Cancer Progression": Clin Cancer Res 2008:14 (24) Dec. 15, 2008; 8236-8243.
V. Cebrian, et al; "Discovery of Myopodin Methylation in Bladder Cancer"; Journal of Pathology 2008; 216: 111-119.

* cited by examiner

D

| Digest protocol | n | Yield: Median conc. (ng/μL) | Lower quartile (ng/μL) | Upper quartile (ng/μL) | Range (ng/μL) | Purity: $A_{260/230}$>1.79 (% of samples) | $A_{260/280}$>1.79 (% of samples) |
|---|---|---|---|---|---|---|---|
| 1 h at 56°C | 43 | 16.8 | 8.2 | 105.3 | 3.8-482.9 | 30 | 40 |
| 48 h at 21°C | 35 | 29.9 | 14.2 | 55.6 | 4.8-264.7 | 43 | 89 |

E

SEQUENCE LISTING

<160> NUMBER OF SEQ ID NOS: 657

<210> SEQ ID NO 1
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 1
ttgcgaaggc cgagatctgg gcctgccagg ggcctgcccg agtcctctat cgcgggtcca 60
cgtggccacc aatgacccgc ggcgcccccg cgtgtccccg cagccactcc gcggaagcag 120
cg 122

<210> SEQ ID NO 2
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 2
cctgctcgcc cgcggccggc agtgagggcg gcagcggctc gtagcggtcg cagccgccgc 60
cgccacagcc gccttgaggc ggggcccctc caccatcggc cacctccggc tccagcaggt 120
gg 122

<210> SEQ ID NO 3
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 3

```
ccgggacccc gtccctcttt ccccttcagt cttcagggag ggggaggcgc tccgcattag     60

cggggcagtt cagcaacccc gaccccaccc gcgtggctcc aggcccaggg gtccgttcac    120

tt                                                                   122
```

<210> SEQ ID NO 4
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 4

```
gtggagagct cactctgcag aataaaatca agaacaccac ggttgtagct gctgtggact     60

cggcggtctg agcagcctcc ccgagagccg tagttgctag tagaagtaag attgagctct    120

gg                                                                   122
```

<210> SEQ ID NO 5
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 5

```
ctccaaatca aaaccactaa gagttcctcc cgcgcagact gctgcccctt cagctgccct     60

cgattttgct ccacgcctgc cggccagagc ctcccggcgt ttcttccgcc ccagcggagt    120

gc                                                                   122
```

<210> SEQ ID NO 6
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 6

```
ggagcgctag tacttgcttc tcgactcccc ggccgccgcc tccggccgcc ccggggattc     60

cgccaccaaa cgcacgcgtc ccaggtgggc acccgcctcg gtccgtcttt gagtctgacc    120

ct                                                                   122
```

<210> SEQ ID NO 7
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 7

```
gcctctcttg acgcagctgt aaaatgcgga tgacaccatc tggttttgct cagaggaatc     60

cggtttggga aagggatgtg ttttcttccc gggccaagtt accaccaccc gcggcgccca    120

ct                                                                   122


<210> SEQ ID NO 8
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 8

tggctgccgg gggcgggaaa gtgatttctc ggaaagcaga gcacttcgaa gaaggcgggc     60

cgcgcgagcc aagctgacgc tattggtcgg tgtggccgtc gctctgcgca ccgcccgtcc    120

cc                                                                   122


<210> SEQ ID NO 9
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 9

gcagtggagg ggacgagggc ttgtcgggtg ggaaacttaa ttcaaaatgg ctgctggaaa     60

cgcttgggtt ttattcgtag caaatgttgc caatttctcc ggccagatac gctaaaccga    120

tc                                                                   122


<210> SEQ ID NO 10
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 10

ggcggcggcg gcagctgcgg cggcggcggc ggcaaacggg tagccctcgt ggtgcaccac     60

cgggtggtgg ggaaaaccac ctaccagact catttcgccc tccgcgcccc tccacgcgcc    120

cc                                                                   122


<210> SEQ ID NO 11
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 11

tctccaagac tgcctcacag ggacccccag gaggctccga accatccagc tttctgtcac     60

cgccgccgcc accagcgttg tgaacctctg accctcgcgg ctctgcgtcc attctcaggt    120
```

```
ac                                                                    122


<210> SEQ ID NO 12
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 12

tcccaccgcg agaagctcac caagcctgaa ctcttcaatg gcgcggagaa gaagcgcaag      60

cgcacgtcca tcgctgcgcc agagaagcgc tcgctcgaag cctactttgc cattcagcct     120

cg                                                                    122


<210> SEQ ID NO 13
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 13

ccagaggttc gacctccagg gcagcgcagg gtaccccggc ttcggagcgg gaagggagcg      60

cgccccgtcc tggagctccg actcccaccc catctgcgct gagccggagg cgctggtttg     120

gg                                                                    122


<210> SEQ ID NO 14
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 14

ctctgggctt gttttcagct tatttaattc acactgaaat gtttctgcgc gggacgaact      60

cggtgtcacc gggtccctcc cggagggtta cttcctgccc ccgacagtgt aatgaggcaa     120

ga                                                                    122


<210> SEQ ID NO 15
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 15

cgggggtgac ggggcgcggg cgcggggtgg gctgggggcg cggatcagtg ggacggagtt      60

cggggttcgg ctccgagcgg gcgggctgga agtgggggat ccctcagccg cctccacggg     120

cc                                                                    122
```

<210> SEQ ID NO 16
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 16

```
ggaggacgag gcggagagcc acccaagaaa ggtggcggag gcggggagac cctgcgggca     60

cggctcacgc gcacatcccc ggcttccccg ggctccgcgc cttcccaaga gccccgttgt    120

ct                                                                   122
```

<210> SEQ ID NO 17
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 17

```
acttgtctcc ggattcgttt tggaggacca gtatccgact atgctgaagc ctgcggtggc     60

cgagaaaggc gtcagcaaac gaggccttcg ggggtgtcat cttagagctc cagcggacct    120

cc                                                                   122
```

<210> SEQ ID NO 18
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 18

```
ggggaagagg cggcagcggt gaggccaggt cgctcctcct cgcgctcccc gccctttcgc     60

cgcctccgcc cccgagccga gcccaccgcc tgttgcagcc aaagccgcga tgctctgtct    120

gg                                                                   122
```

<210> SEQ ID NO 19
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 19

```
gtgcggtagt aattgagcac ataggcgaag acgcccgggt gccggtcgaa gaagaactcg     60

cggccgccac cgggatggtc gctggccctg ccgccgcggg aactgcagtt gcccgcgccg    120

cc                                                                   122
```

<210> SEQ ID NO 20
<211> LENGTH: 122

<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 20
ggctctccga gggccttggg gttgggatcc ctaggtgcag cccgttgaca gtcggcccca 60
cggccatgga cgtcctttcc ccaagttagc tgagcgcctg ccaccgagat cccccgagcc 120
tg 122

<210> SEQ ID NO 21
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 21
agattagcca ccccgtgcgc ccaggtgaaa gatatcattc ttccgtgcga tccgaagtgc 60
cgtggaagtt agtgccctag cccagtccag gaggaagggg cgtcgtgccg gcggttttaa 120
gc 122

<210> SEQ ID NO 22
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 22
gccgagcccg aaccccaagc cgcggagcca gcacctcctc cagtcggggt cgtccgctcc 60
cggccgttga gccaccgccg ccacccggta gtgtgtcccg ctgccccaat ccgcctcatc 120
aa 122

<210> SEQ ID NO 23
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 23
gagactgcgg ctcgcgggtc tctccaccct ccccctgcgt cctcctccgc cctcctctgc 60
cggatccgac ctgcgcccct acgctggccc agctgctagg aactagcgcc ccgagcgccg 120
cc 122

<210> SEQ ID NO 24
<211> LENGTH: 122
<212> TYPE: DNA
<213> ORGANISM: Homo sapiens
<220> FEATURE:

<221> NAME/KEY: misc_feature
<222> LOCATION: (61)..(61)
<223> OTHER INFORMATION: /note="Nucleotide may be methylated to form 5-methylcytosine"

<400> SEQUENCE: 24
ttacttggga ggtcccgggt atctgaagcg gatcccgggt ctggggacat gaaggggcgc 60
cgtggcctta gggaaggccc caaagaggcc taggccccgg aggaggcaag agccgcggcc 120
ta 122

<210> SEQ ID NO 25
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 25
ggggagaggc cgcgggtcca gaaaccgtta ctggatgggc cggtgggatg tggcgcgggc 60
cgggtggggc gcgacagtct gagccgagac ccgcgtgggc ttaagggtgc gcgaggcggg 120
tg 122

<210> SEQ ID NO 26
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 26
cgggcccctt ttaagcgctt ggagtcacta ggaatgtacc aacggccctc ggagggagga 60
cgaggcggag agccacccaa gaaaggtggc ggaggcgggg agaccctgcg ggcacggctc 120
ac 122

<210> SEQ ID NO 27
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 27
ggcggagagc cacccaagaa aggtggcgga ggcggggaga ccctgcgggc acggctcacg 60
cgcacatccc cggcttcccc gggctccgcg ccttcccaag agccccgttg tctccggcgt 120
cc 122

<210> SEQ ID NO 28
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 28
acacggggcg taaagcgcgg cggggagtcc ggggggctcc cgcctggagg gctgtgtgag 60
cggcgggccg cggggcggcg cggggggcgc tctccactct gcggaagctg ccccctctgc 120
cc 122

<210> SEQ ID NO 29
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 29
cggcgcacac tgaaccgaag acctcgtagg cgggcctcgg ggggatgatg ccgttggcgg 60
cggccagcgc cagcccctcg gcagtgccgt agagcagctg cagctcgcgc gcctcgttct 120
cc 122

<210> SEQ ID NO 30
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 30
ccctgcgggg caagggggc tggtggaatc tggcggtccc cagctgcccg tgtcccgggt 60
cggtgcgctc ggcgcacccg tggtgacagt gcccggcgtc tgctcccacc cgcccgcccg 120
cc 122

<210> SEQ ID NO 31
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 31
aaaaagaacg tgagatatta gagagaaacg attgtctcaa accgaaacag ctctcctacg 60
cgaaccccag atattcctga cttggagtag ctaagatttt atcagcattc tgggaatttg 120
ca 122

<210> SEQ ID NO 32
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 32

```
cttttaccca aagcttggtc aggagccctg agctgcgatt ggccgacggg tagaccgtcc     60

cgggtggcgg agacacgcgc tgattgggca acagcgacca ctttctcttc ccatctctgg    120

tg                                                                   122


<210> SEQ ID NO 33
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 33

ggcgtgtccc attgcagcac cgacccggac accccgagcc gagagccagg cgggcgggaa     60

cgctccgggc ttcctgcact ggcaggcgca gccggcccac gcccgccccc tgctgttacc    120

ac                                                                   122


<210> SEQ ID NO 34
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 34

gattttctga tctagcaaag accttcccac accccgggaa aggacaaggg aagggcttct     60

cgcccgtgtg cacgcggatg tgatttacaa gtttgtattt ggctttgaag ggctttccct    120

gg                                                                   122


<210> SEQ ID NO 35
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 35

gtgaagttcc gcaaagtgct tcgcagcggg ccgagcccgc gggagccacc tgcccggccc     60

cgacgcgcat ggtcatttat aaatttaaaa ctcttccgta gcaaccggtt atgtacagag    120

tc                                                                   122


<210> SEQ ID NO 36
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 36

gtggcgctcg ctgtccgtgc agcgggcgga ggcggccgcg gtgcctttgt gtgcggtggg     60
```

```
cgcggcgatg ggctgctccg gcccgcagcc cgaggggagc ggcgggcccg ggccggggcc    120

ag                                                                   122


<210> SEQ ID NO 37
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 37

cctgtccgcg ccgcccgcgc ggtctccggc cccctgcgcg aggtcctccc tcctgcctcg     60

cgctccacgg ctcctccgcg ctctgcctcc cgcggcgcct gccgcctccc ctgcgcggat    120

ca                                                                   122


<210> SEQ ID NO 38
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 38

ttacgatttc actaatggca gctcaaagct gctgagctct gccctgacgg catgcgcccc     60

cgcttctgtg agagcacgct tcctggcatg gggtcgaat catgtcgata aaatgggctc    120

gg                                                                   122


<210> SEQ ID NO 39
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 39

tgcctccctc gtcgcccggc aagggcaggg gcgggggtgg cgtcgggggg tcgctgtggc     60

cggaatccag ggaggtgcgg cggggcgagc gcagcagcgc cgcctgatgg tagggcacac    120

tc                                                                   122


<210> SEQ ID NO 40
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 40

cgagccgggg gtggcgggcg gggacgtctg ctcgtcagag tcattcaatg aagatatagc     60

cgtgttcgcc aaacaggtca gcaaaataga tgttaaaaag taaaagaaac aaaaagagag    120

cc                                                                   122
```

<210> SEQ ID NO 41
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 41
tttaattctt ctgcccggga gacctaaccg ccgaatgcgt tcggaggtat gtttttttaat 60 cgccaggaaa gggggagaga gagagaaaga gagagagaga gagagaggaa aggaggagag 120
aa 122

<210> SEQ ID NO 42
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 42
aggaggagca cgtgcggtcg gtggggcgca gggccgggga gccagggggg tgccggggct 60
cgaggccgcg gggccgcggg ggccgcgctc tgctctccgc ccaggctggg ccactggagc 120
gc 122

<210> SEQ ID NO 43
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 43
aggcgaaggc cgcccccggga gagcggggtc ccgggagagc ggggtcccgg ctgtggggga 60
cgcgggccga ggctgtcgcg aagccgctga cggccgaggc gctcccggtt ttcgcggcgc 120
ac 122

<210> SEQ ID NO 44
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 44
gcggggtggg ctgggggcgc ggatcagtgg gacggagttc ggggttcggc tccgagcggg 60
cgggctggaa gtgggggatc cctcagccgc ctccacgggc cggccccgcg ctcacgtcgg 120
tt 122

<210> SEQ ID NO 45

<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 45
cgctggcgct ccgcgatgag cgtgcacttg gcgcacaggc agtccttcca gcgacagtag 60
cgtttgtggc ccttgagggc cgacaccacg ccatggttgc gacagcgcgc gcacttgggg 120
gt 122

<210> SEQ ID NO 46
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 46
ccgcggtcct gcagttgccg ctccggtccc cagcgctggc cggcgacccg aggcgcggct 60
cgcacctacc tgcagccccg cttcccggtg gcggcaacac ctagcgatgc tcctgcagct 120
tt 122

<210> SEQ ID NO 47
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 47
ctggtggctt gtccgatttg cacggtgact tgattacact ctctcattca tggtcacttc 60
cgaagcgctt tagtgccttc cgtccctaaa ccgccaacag ccagaacggc ttctccccgc 120
gg 122

<210> SEQ ID NO 48
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 48
tttcttccgc cccagcggag tgcgctgggg cgcgccaggg ctaggcccgc cggaggagcg 60
cgtccccagc cttccgcgca cagagccgca tcccgccccg ccctgcgctg gactggttca 120
ag 122

<210> SEQ ID NO 49
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 49
cccggggctt aacggctgct ggagccactt tataattagc cccaaaccga aggaggcgcg 60
cgcgccccaa tcgccggcgg gctgcagctg acgcaggccc tacgccagcc ccgcgccgac 120
gc 122

<210> SEQ ID NO 50
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 50
ggcgagcggc ggggccgggg catcccagct cctgccaagc ttggcggcgc gaggaggagt 60
cgccgggcgc agcccccaat cacccaggaa cgcggggacg cctgggccac tgctccggcc 120
ga 122

<210> SEQ ID NO 51
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 51
cacaggtttc cgtggtgtag tggttatcac attcgcctta cacgcgaaag gtcctcgggt 60
cgaaaccgag cggaaacaac ttgcaatttt tcggggtgtt tctgttttcc aagattccct 120
ta 122

<210> SEQ ID NO 52
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 52
gtaaaaaccc gttttatggg ggaacgtaat tgtgagcggg atgcgctctc tttagaatcg 60
cgtcctccca aatgctcccg ccgtcccatt accggaatgg ggaccattcg gctgctgcag 120
at 122

<210> SEQ ID NO 53
<211> LENGTH: 122
<212> TYPE: DNA
<213> ORGANISM: Homo sapiens
<220> FEATURE:
<221> NAME/KEY: misc_feature
<222> LOCATION: (61)..(61)

<223> OTHER INFORMATION: /note="Nucleotide may be methylated to form 5-methylcytosine"

<400> SEQUENCE: 53
ggccccgcat cgcctggcgc aattggaata acaaatgcga cgcacgcaaa ttgtccacct 60
cgtgttgcta agcgattgtt tgtcggcccc gcacgcacag ctcagcatgg gaggaccgcg 120
ag 122

<210> SEQ ID NO 54
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 54
ggcgcggcgg gggtgacggg gcgcgggcgc ggggtgggct gggggcgcgg atcagtggga 60
cggagttcgg ggttcggctc cgagcgggcg ggctggaagt gggggatccc tcagccgcct 120
cc 122

<210> SEQ ID NO 55
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 55
gctgccgggg gcgggaaagt gatttctcgg aaagcagagc acttcgaaga aggcgggccg 60
cgcgagccaa gctgacgcta ttggtcggtg tggccgtcgc tctgcgcacc gcccgtcccc 120
cc 122

<210> SEQ ID NO 56
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 56
ctgctcgctg ggcgctgagg agggtgggcg cggtggcggg ctgagggcgg cggcggcgag 60
cgcagaaggc tgaggcgctc gtccatgcgg cggggaagag gcggcagcgg tgaggccagg 120
tc 122

<210> SEQ ID NO 57
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 57
actgcttgca ctctgcggct gagcccttgg ccgggagggg cttcttgcca ccaccgcccg 60
cgctaccacc tgcgccgccg cccccagcca cacggggccg cttcctcttg cagccttccg 120
cg 122

<210> SEQ ID NO 58
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 58
ggcgggccag ggagcaccca gtgcgccccc tccgcgggcg gcacaagagc agcgctcggc 60
cgccgcctcc agccaactcg ggtccctccc acggcgacca atcagtgcga agctggctgg 120
gc 122

<210> SEQ ID NO 59
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 59
atttcggaga ccgaattcaa aatgaaaaac cgggctgctg tcccgcacgg agcctctggg 60
cgccgctgtc ggccagtgca gagcaagcgc tgacgccggg gatccgtcag cctctggcct 120
gg 122

<210> SEQ ID NO 60
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 60
acctccgctc gtattgggct gggagttcag agccgcgcgc agaacccggg ttggccgcaa 60
cgtctgtgtt ctcagcggtg gccgggaacc tgggatcagg gtcacctgag ctgacggggt 120
gg 122

<210> SEQ ID NO 61
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 61
ccggaggttc gatggccgcc gggccagtgc gggctcagag gaagaccctg caaaaaagag 60

```
cgctcgcccc caccccctgga gccgaccctg cgcagtaggg ccgcagccgg tccccgcggg    120

ca                                                                    122


<210> SEQ ID NO 62
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 62

ggcgcagata taagcggcgg cccatctgaa gagggctcgg caggcgcccg gggtcctcag     60

cgctgcagac tcctgacctg ccgactgcgg atcccgagtc cccggatccc ggacccatcc    120

tg                                                                    122


<210> SEQ ID NO 63
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 63

gtcggatctc taaattatct aatctggcgg ctgcgtacga ctcagggaaa gccctggccg     60

cgagcttttt caccaggctt gagctcagca gccgggcccg cagtgttgcc gccagtgggg    120

ag                                                                    122


<210> SEQ ID NO 64
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 64

gtctctccac gcgctgccgc ctagcaaagg cgcatcttta ggtcggtagt gaggtgcggc     60

cgggacgctg caactcgctc cgggacttgt aaacctggca ggtgttcgaa gagggccact    120

gg                                                                    122


<210> SEQ ID NO 65
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 65

cactcaacca ttataagttc accccagccg tcagcgatgg cgtaggtagg tagtcgtggc     60

cgagtggtta aggcgatgga cttgaaatcc attggggttt ccccgcgcag gttcgaatcc    120
```

tg 122

<210> SEQ ID NO 66
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 66
gtgtagagaa caacagtcgc tccttagata ttactccagg acggaaacct gattgcaaac 60
cgctgttcct tcgaaacttg caaaacccgg aacagaaaac tcccgcccag ccaattttag 120
ct 122

<210> SEQ ID NO 67
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 67
attcagaccg aatggctgcg cggtgatgga tgcggattta cggcctcctt ggctgcggcg 60
cgctgggcct gattatcact ataaacaggc gtccgcggag ggcgggggcg gaggcccgcg 120
tc 122

<210> SEQ ID NO 68
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 68
ttaaccacag agttgttctt gattgtaagg gacttcgccc acttggttga agtggagagc 60
cggtcctcat tccagacgtc ccgcacggca gtcgctcatg gctccctcca ggccgggagc 120
ca 122

<210> SEQ ID NO 69
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 69
gcagggaccc ggctggccgc ctccccttgc aggaaacagg tgtttgaacg cgatagcggc 60
cgccagtcaa ctaaggcatt aaaagctcgc tttataacat cgatttcctg gagtgcggtg 120
gg 122

<210> SEQ ID NO 70
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 70
tgcttctcga ctccccggcc gccgcctccg gccgccccgg ggattccgcc accaaacgca 60
cgcgtcccag gtgggcaccc gcctcggtcc gtctttgagt ctgaccctag cgcaagagtc 120
cc 122

<210> SEQ ID NO 71
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 71
ggactccgag ccggggcgtc tcaggggcag agcgcacggc acagcggggc gggcgtgggg 60
cgtgcggagc gagggctcgg ttctgggacc cctctcgcct tctctcagac ggctggggag 120
ga 122

<210> SEQ ID NO 72
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 72
ctgcggggcg cgcgcccgcc tccgcgtccc cttaggattc ccgcccaccg cgcgggcgcg 60
cgtcccgctc tcgggggcag ccgccgggcc tgcatttctt gcagccctca aggcccctcg 120
gt 122

<210> SEQ ID NO 73
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 73
ggaaccagat cttgacctgc gtgggcgtga ggcggatgag gctggccagg tgttcgcgct 60
cgggcgccga caggtaccgc tgctgccgaa agcgccgctc cagctcgtag gtctgcgcct 120
tg 122

<210> SEQ ID NO 74
<211> LENGTH: 122
<212> TYPE: DNA

<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 74
actgcggcca cagcttctgc ctcaggtgca tctccgagtt ctgcgagaag tcggacggcg 60
cgcagggcgg cgtctacgcc tgtccgcagt gccggggccc cttccggccc tcgggctttc 120
gc 122

<210> SEQ ID NO 75
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 75
ggatgcagac gcaccagcgg ctgctcacac tccctccaca aacctgccgg agtctccact 60
cgcccgccaa ctgtagcctc catctgcgcc ccacgccccc gcacaagccc cctccgtcgc 120
gg 122

<210> SEQ ID NO 76
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 76
ggcgcaaaag gggccgcccc cgtgccggga acagactttg aagtgggttt ttagcgcgca 60
cgtgtgagag ccgggccagg gccggagcgg ggacccgctg ggaggaaaga ggaggctccg 120
gc 122

<210> SEQ ID NO 77
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 77
ctcccaccca tcgccaccgc gtccacactc cgccgcattc cagagaaaaa gaaaaggcca 60
cggcctcgta aagctcccag ctggcccgga ccccgagctc ctcccggtta gaagccgaag 120
cg 122

<210> SEQ ID NO 78
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 78
gatttccttt aaagtaccta ccacgccacc cgctacctgt aataatccat ctgaagaggt 60
cgccgggcag cgcctcggca gacagactga cctgcgggga ggtgcggttt ccagtggcgc 120
gg 122

<210> SEQ ID NO 79
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 79
cggcgcaggc cccgcacccc cgactctgcc cgccctctgt tacggacacc cgctgggcca 60
cgtggtcgcg actggcttct cccagcggcc agcctggcca ccccgactcc cagggagggg 120
ga 122

<210> SEQ ID NO 80
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 80
tcggccctcc gccccggggc atcctggcct gagcaacgac ccgggctccc gggccacccc 60
cggctccagc cacccgctcc gcccggctga aactcaggcg ctttccgagg agaagtgcgg 120
cg 122

<210> SEQ ID NO 81
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 81
ttctcaccga aagcacgtaa tcgccggtgt aactcatgtt ggctgggggg cctcccggcg 60
cgcgcggaga ggctggggtg cgcccccatg cagcatgctt gtgctcaatt gcagggtcct 120
cg 122

<210> SEQ ID NO 82
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 82
gctgaagtcg gggtgctcgg ccagcgtcgc cgcctgccgg ggaggctggc ccagggtccc 60
cggcgcatag cggccaacgc tcagctcatc cgcggcgtcg gcgcccagca ggaacgagtc 120
ca 122

<210> SEQ ID NO 83
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 83
gggttgggtt ggggctggag tagccgaggc cggcctgggt ccgggcagtc aggcctgacg 60
cggccccgcg cccttccccg gcagagaagc ccgggacggc catgtgcgtg ggctgcggga 120
gt 122

<210> SEQ ID NO 84
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 84
gcgcttccgg cgatccgcct gggcggctgg gtccgcgaag ccaatgcgct gaacggtgcc 60
cgagtcttcc taactatcct gtgcttggcc gttgccactg ggccctggtg actaagccca 120
ag 122

<210> SEQ ID NO 85
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 85
taccggccct cagcttgggt gcatctcctc caccagctgc cccgcgccga cttccagctc 60
cgcccggtgc ccagcgtttt cgcgccccaa gagcaggaat accagcaggt gggaccgggc 120
gc 122

<210> SEQ ID NO 86
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 86

```
gtcccaaatt ccccgggccg cggctaatta tcgggagctt gatgttgata agtaaagcgc     60

cggagtgcgg gcgaagcatg tgtggggctc cgggtccctg tctccgccgc cgccgcccgc    120

gc                                                                   122


<210> SEQ ID NO 87
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 87

gaggggcggt caacttctgg gaatggccaa gaggggtgct ctgaggcccg agccggggtc     60

cggtgcccgc ggccggcggc cggggtctgt ttactccggc gacgtgcgga gaggacccaa    120

gc                                                                   122


<210> SEQ ID NO 88
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 88

cgccgccttt ccctcctcgc ctcttccttc cttccgggtc gtgccctcca acctgctgtg     60

cgttaccgca gccaagtttc caccgcccgg cggagcgcat tgtgaacagc agctgacaaa    120

tt                                                                   122


<210> SEQ ID NO 89
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 89

ccgactcggg atgacaattg acggggatca agggattgcc cattctgtgc ctgtaagaac     60

cgattcgtgc cagagaaact catcaagtgg aggcggagaa taaagaccgt tcgggggtaa    120

at                                                                   122


<210> SEQ ID NO 90
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 90

ggcagctcaa agctgctgag ctctgccctg acggcatgcg cccccgcttc tgtgagagca     60

cgcttcctgg catgggggtc gaatcatgtc gataaaatgg gctcggtttc atgaagtacc    120
```

cc 122

<210> SEQ ID NO 91
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 91
gaaagccgct actccctggc tggctgagct acagctcccg cagcgcgccc aggagtgcgc 60
cggagattcg gaaacccgca gagacttctc aagtcagcag gaacttggaa accgctgttc 120
cc 122

<210> SEQ ID NO 92
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 92
ctcgctcggg cgtgttcctg cgccgaccgg acggccggac tccagcacct tggcccggcc 60
cgcgaacgct gagcacgcgc ggaaaccctt taaaggtagc acatttttcg ggtgtcgcgg 120
gg 122

<210> SEQ ID NO 93
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 93
ctggaaaagc cgggagggag tcggaggcgc cagcccactg gggaggtggc gctgggcgcg 60
cgggatgcgc ggggagcctt ctctgcagga gccgcacagt gcactgctgc gcgctgggca 120
gt 122

<210> SEQ ID NO 94
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 94
tctcccgtag ccctgcgggc cgctcttcac tgctctccag acttggggcc ctatctgagg 60
cgtcccaaac accaacttct ggctcctggc cccaactcga gaggcttcca gcgaggacga 120
ag 122

<210> SEQ ID NO 95
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 95
gagcccaccg cctgttgcag ccaaagccgc gatgctctgt ctgggtctgg cgcggtcagc 60
cgggctcccg cacggggacg cctcctccct ccttctcgcg ctctccgccc cctcccctgc 120
gg 122

<210> SEQ ID NO 96
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 96
cgaagttgtt gttggcggcg gcagtggccg gctgcgctgg ggaaggcccg gcggggtaag 60
cggcagtgca gctgtagcca gggctgcagg ccgcgccgcc gtaacccgga taggcggggt 120
ag 122

<210> SEQ ID NO 97
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 97
gtccattctc aggtactgaa agttttccgg gctcttccgc acccgcggat gtggcgaagc 60
cgcggggcag ctccgctcgc gctccagtcg caggatgtcc ttgaccgaga agggggtgga 120
gg 122

<210> SEQ ID NO 98
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 98
cgcccccgcc cccgccaccg ctgccgccgt cgccgctgcc accgggctat aaaaaccggc 60
cgagccccta aaggtgcgga tgcttattat agatcgacgc gacaccagcg cccggtgcca 120
gg 122

<210> SEQ ID NO 99
<211> LENGTH: 122

<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 99
cagtgacggg aaccaatgag ctgccaactc gcgcgtctcc ggcgtgactg ccgagattga 60
cgtggaggac acgtcaaatt gattcccgca cgctgcagcc tcccggtcag acgaatttct 120
cc 122

<210> SEQ ID NO 100
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 100
ctccgcctcc tcccagaccc ttctccgggt gcgactgacg tggctccgca ccaatcagga 60
cgccccgagc cgcggtggag ggactgtcct gcctgcacct atcagcagtg cggggccggg 120
ct 122

<210> SEQ ID NO 101
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 101
ttagcacccg ggcgccgggg ccctcgccct tccgcagcct tcactccagc cctctgctcc 60
cgcacgccat gaagtcgccg ttctaccgct gccagaacac cacctctgtg gaaaaaggca 120
ac 122

<210> SEQ ID NO 102
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 102
aggcgcagcc agcggcactt caaagcgggt gctcctcgca cttaggctga gtttagccgg 60
cgggagcctg gagtccgctc ggcacgagcg cggggacgcg ggagccgcgc gggacccaag 120
ca 122

<210> SEQ ID NO 103
<211> LENGTH: 122
<212> TYPE: DNA
<213> ORGANISM: Homo sapiens
<220> FEATURE:

<221> NAME/KEY: misc_feature
<222> LOCATION: (61)..(61)
<223> OTHER INFORMATION: /note="Nucleotide may be methylated to form 5-methylcytosine"

<400> SEQUENCE: 103
ggccgcgttc cggttccggt aggttgcccg ggagacgcgg gtacacagag aagcggctcc 60
cgtcggaggc cgagtcgtcg ccacgatcgc ccccttggtg gactcgcagg ccgagcggct 120
tc 122

<210> SEQ ID NO 104
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 104
gggagcgcat tttccggctg agatgtcggg actctgcttc cccaaccgaa cgcgatcaca 60
cgggaaactc ttcgcccaca acagatgaga tggccaaagg attgctgagt gcgcacacgc 120
aa 122

<210> SEQ ID NO 105
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 105
ggactcatgc agaagaggac attccgcagg taggtacaat cccagcgctg gggcctgggg 60
cgtccggggg gcggcctttg agcttcccgg ataccgctcg cctgctcccg gagctgttcg 120
gc 122

<210> SEQ ID NO 106
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 106
gggggagtta aaaaaatttc tgagaaaact cggaacttgc gctccaggaa cgactgcgca 60
cgtggcgcgg cggtggcggc gcggaggacc caggcgaagg cgaaggcgaa ggcgaaggcg 120
ca 122

<210> SEQ ID NO 107
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 107
gactgcgtcg cctcgggtgg caggtggcgg tgcgggcggg cgctgcaagc cggagagggg 60
cgcgggaggg cgagtttcgg ctgtggccct gggactccga gccggggcgt ctcaggggca 120
ga 122

<210> SEQ ID NO 108
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 108
gagggcgtct cggggaggcc agggacaggt ctgcgacgaa gtccagcacc gtagtgtcca 60
cgcagctctc cggataggcc gccatcgctt cggcttggcc ctgcctctca tcggttttcc 120
gc 122

<210> SEQ ID NO 109
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 109
gtataccgct ccacaccctt tcgtgcccgc gcgctgaagg ttctggggtt cgtatccgcg 60
cgcttgcgct gcaagactcg gcaagtttgt tccgactgta actccgggga tgaggaacgg 120
gg 122

<210> SEQ ID NO 110
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 110
cacagaggag gggttggggg cagcggaaaa tcgggcaggt cgaggcagcc gaaccccgga 60
cgatgtcccc ccacccaccc cgaaggtcgc agcctgggcc gcgttctcag caggagtcgg 120
gc 122

<210> SEQ ID NO 111
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 111

```
cagaaggacc atctgcggac tcgttttcac tgctccagct cccgaaatcg tttctctgga     60

cgcggcagta tccgcagcgc atgcaccctc ctctggactt ccgcagccca gacctgcgct    120

ta                                                                   122


<210> SEQ ID NO 112
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 112

gggggcaccc agggcaggct ggtcttgagc ctggagaagg ctttgctcag cacgcgcatc     60

cgggcacgct cacgggcgtt ggccgcgttc cgctgcgact gcttgcactc tgcggctgag    120

cc                                                                   122


<210> SEQ ID NO 113
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 113

tcggagaccg aattcaaaat gaaaaaccgg gctgctgtcc cgcacggagc ctctgggcgc     60

cgctgtcggc cagtgcagag caagcgctga cgccggggat ccgtcagcct ctggcctggg    120

at                                                                   122


<210> SEQ ID NO 114
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 114

ctttctccac ggtcacttca cagctaagat ttctttcttt ccgagctgta gaaggcagaa     60

cgctctcggg aggacgaagt gatccgaagg gatgtggcaa gcgcactttc cgatggagat    120

gc                                                                   122


<210> SEQ ID NO 115
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 115

gggagggatc tgtgctcact ttctccaata cttggcttgg agggtcagtt ttcctgtttg     60
```

cggggtgctt gaattcttgg atgagaaaaa gggctgactt ggggcgggag ccgctgaaca 120
ga 122

<210> SEQ ID NO 116
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 116
gcaagacggc cgcgttccgg ttccggtagg ttgcccggga gacgcgggta cacagagaag 60
cggctcccgt cggaggccga gtcgtcgcca cgatcgcccc cttggtggac tcgcaggccg 120
ag 122

<210> SEQ ID NO 117
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 117
tctgagaagt gtcctcctcg ctctcttata aaaacaggac ttgttgccga ggtcagcgcg 60
cgcatcgagt gtgccaggcg tgtgcgtggt ttctgctgtg tcattgcttt cacggaaggt 120
gg 122

<210> SEQ ID NO 118
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 118
ggaactacgg acagtgagcc ctggcgctcg ctgccctgcg ccttaatttg ctggcggcgg 60
cgatcccgga ggcccgcagc cagtcagcgc cgtctcacgt caccgcttcc tgattccgcc 120
gc 122

<210> SEQ ID NO 119
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 119
gctcggggcc cctgggcggc aggaacggca cgtccgctag gagcaggcag ggtgctcgag 60
cggccgccgg cggctgcgtg ccgaagccac agaggaggcc gagtcccagc ggtagggccc 120
ca 122

<210> SEQ ID NO 120
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 120
aatcactgta gttaaaaatg tatgggattt ttgccgtcgg agcacctcgt atccggcgcg 60
cgggcccagt gtgggactgc ggctgggagc ccgggccctc cgggagtgaa gatacctttg 120
ga 122

<210> SEQ ID NO 121
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 121
gcgggctccc cctggccaca tcccgggcct ctcacacaag aagaatagtt ctgtttccgc 60
cgtaaacccc cacacaaagg ctgcccggcc accgggtccc ctgtccccct tcccggggac 120
tt 122

<210> SEQ ID NO 122
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 122
gtaggctgga ccaggaagga gacctggttc gtttcgccca ggctgtcacg gcttcaagag 60
cgcctctccg ctatttccgt cgctcgacag acgggctgag ctctttggag tgatgttggg 120
tt 122

<210> SEQ ID NO 123
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 123
ccggcggggg ctgggccggg cgggtgggtt tctgagccgc agcgcttgga gctgggggag 60
cgggagcagg ggcggcccgg cgggcgggcc gggacccggc ttttccggct acccgtgggc 120
ca 122

<210> SEQ ID NO 124

```
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 124

ggaggttaat agcgactgac gacaaagggc caaggtgcaa ttcctaaagc ggggattcgc     60

cgggtgaggc agaaatcagc ctccggggag atgggtcccc ccttcccgac gcgcccctgc    120

ac                                                                   122


<210> SEQ ID NO 125
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 125

cttcggtttt ccggccagac ccggaaaaac gaaaacacag cttggggagc ccccactagc     60

cggcgcctgt gccagctcac ctctggccat ggcgcagctg ccggtgcaca cggcggccaa    120

gg                                                                   122


<210> SEQ ID NO 126
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 126

tcggcctggc caggcggggg gtcttcttcc cagtccgcgg aagccaggtc cgggagacgg     60

cggggctcac tgtgccttcg gacctacact ctgctcgggg gccggatttc tgcaaagcgt    120

cc                                                                   122


<210> SEQ ID NO 127
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 127

agcctaggat tcgactttga atggtccgtt aatgtggtcg caaaacgtga ctcggttcat     60

cgggcgctcc ctgtaagcaa gacaagcacc cacctgcggt cagagcaggg gtccggctcg    120

cg                                                                   122


<210> SEQ ID NO 128
<211> LENGTH: 122
<212> TYPE: DNA
<213> ORGANISM: Homo sapiens
```

<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 128
gcgggaggga ggagcggcgc ggcgggggtg acggggcgcg ggcgcggggt gggctggggg 60
cgcggatcag tgggacggag ttcggggttc ggctccgagc gggcgggctg gaagtggggg 120
at 122

<210> SEQ ID NO 129
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 129
gggggcggaa caccaggcct cctgactgcc ggggagtggg gcgcagaggg agcgggttcg 60
cgcggagggc aactcacgga ggagaagttg tgcggcccgc agagctcgcc gcggtacttg 120
ca 122

<210> SEQ ID NO 130
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 130
agcaggagcc cccacatggc ggggattgag tgccaggggc gcgcgggcta cggcgggtgg 60
cgggtcggtc tcttcctgcc gagtgcgccg agccccccgc cccttcctgc cccccgcccc 120
tc 122

<210> SEQ ID NO 131
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 131
cgtaaagcgc ggcggggagt ccggggggct cccgcctgga gggctgtgtg agcggcgggc 60
cgcggggcgg cgcgggggc gctctccact ctgcggaagc tgccccctct gccctccggt 120
cc 122

<210> SEQ ID NO 132
<211> LENGTH: 122
<212> TYPE: DNA
<213> ORGANISM: Homo sapiens
<220> FEATURE:
<221> NAME/KEY: misc_feature
<222> LOCATION: (61)..(61)

```
<223> OTHER INFORMATION: /note="Nucleotide may be methylated to form
      5-methylcytosine"

<400> SEQUENCE: 132

cggccgcgtg ctgtacagtg tgagggaacg tgtaccaaac gctcgcggga tacctgtgcc     60

cgtctagcca agagtgcacc cgtgtgcgcg agcgggcttc tgggacgccg ccgtggtcgg    120

gg                                                                   122


<210> SEQ ID NO 133
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 133

ggggaggggg cggaggaggc tgagccaggc agagtcgcca gcggagactc gcgagtggcg     60

cgcgggagga gcggccgccg gcgctgggct tgccttgctg ctgctgctgc tgctgcctcc    120

cc                                                                   122


<210> SEQ ID NO 134
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 134

acacctcccc tttcccccac caactccccc aaagtttctc ccaacacatc ctccggccgg     60

cgcccacacg catacctgtc accagccctg cctcgcattt gcgttctcga tccagttcca    120

tc                                                                   122


<210> SEQ ID NO 135
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 135

gtatccggga ctccgaaacg cgcggcgagc agccccctcc cccaccgccc agacggggtg     60

cgaccgccca cgtgtcgccc cttgcccagt cgggtccttc cctcgggctc cgggagccgg    120

ag                                                                   122


<210> SEQ ID NO 136
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"
```

<400> SEQUENCE: 136
gaacgcgggc ggcgagacgg cggcaggacg gcggcaggta ggcacagtgg gcgggtaggg 60
cgcccgtgtc ccgcgcggtc cggtcccgcg gggtccccga cgccaggcgg ggcgtggggg 120
tg 122

<210> SEQ ID NO 137
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 137
acattcatgt ctagggacgc agggtgcaga agcgagactc gagagtccac cggccagggg 60
cgtctgtcca cgggtctgca cgggagcgca ccgccgctcg gcccgggggc gtccgtggcg 120
ct 122

<210> SEQ ID NO 138
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 138
taattcgcga acagtcggga gaacaaacag ccaagcggcg ctgcagtggc cgcacttgcg 60
cgcgtctcaa tcctgggggc tctgcgcgcc cgccccagtc cctcgcccca ttgactcagt 120
gg 122

<210> SEQ ID NO 139
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 139
ccggtccccc tccatgctcg ctcggccgtg cgcttacccg ctgcacaacg cgtcccgccc 60
cggcctccag cccactctcc gcgccgcgcc agcctcgaac ctggatctcc gcgggcgcct 120
gg 122

<210> SEQ ID NO 140
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 140
cgctggaaaa tgctgaagga cagcgagaag atcccgttca tccgggaggc ggagcggctg 60

```
cggctcaagc acatggccga ctaccccgac tacaagtacc ggccccggaa aaagcccaaa    120

at                                                                    122


<210> SEQ ID NO 141
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 141

ttcctcttgc cctcctcctt cttgctccct cccccatccc acccactcta ggaagagccg     60

cgcttcggaa cgaccccgtt ggccatgctg gcggcgacct gcaacaagat cggcaacacg    120

ag                                                                    122


<210> SEQ ID NO 142
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 142

atcatctcat tggtgagctc cttgaagcgc agccacagct cgctctcctc caggcccacg     60

cgcagttcgc gctctgtggg gtcgcccttc tcgctgcccg cctgcagctc attctccacg    120

gc                                                                    122


<210> SEQ ID NO 143
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 143

gccaaggagc tgaggaaatc cggcgcagac tctcccagct ggcaccaaag ccttccgctt     60

cgccgagatc ctctcaggtg ctcttgagga cgcgagcgac ttccctagga gcgaacttcc    120

gc                                                                    122


<210> SEQ ID NO 144
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 144

ccctcgggga cagcccggcc ggccacgccg ccgaactcgc catgggcctc tctccgcatc     60

cgcatgtgca tccgcaaccg cttccgtccc gctgagcgca cgaaccctct cgctcctgtc    120
```

```
cc                                                                  122


<210> SEQ ID NO 145
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 145

tcctcaagag aggtagggtc cgttcccccc ggcggggccg gttagctcag ttggttagag     60

cgtggcgcta ataacgccaa ggtcgcgggt tcgatccccg tacgggccac aggcttttct    120

aa                                                                  122


<210> SEQ ID NO 146
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 146

gagcaggctc cccagcgtag cgagtccttg ttatggaaag ggtcgtttcg gctcaggatg     60

cgcgctcccg gcgtagacct ggggataggg gtccctgtcg cgctcgcccc acccctgcag    120

gg                                                                  122


<210> SEQ ID NO 147
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 147

gtggcggcgg gacaccccgc gcaggccaac aaaaggaggg gagccgctcg ctcccgcttc     60

cgcgttttca ttcaacttcc tgggcctaaa gcgccctcca gcagcctgcg ggccgccatc    120

gg                                                                  122


<210> SEQ ID NO 148
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form
      5-methylcytosine"

<400> SEQUENCE: 148

aaacggcgtc tgtggggagt agctaggggc ctgcccggcg ggggcgcagg aacccggttg     60

cggtgccggg aggagggtcg ggagggtctc agccccctcc ttgctcccag gcttccactc    120

ct                                                                  122
```

<210> SEQ ID NO 149
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 149
gcgtgacaac atacagggca tcacgaagcc cgccatccgt cgcttggccc gacgcggcgg 60
cgtgaaacgc atttcgggcc tcatttatga ggagacccgc ggtgttctta aggtgttcct 120
gg 122

<210> SEQ ID NO 150
<211> LENGTH: 122
<212> TYPE: DNA
<213> ORGANISM: Homo sapiens
<220> FEATURE:
<221> NAME/KEY: misc_feature
<222> LOCATION: (61)..(61)
<223> OTHER INFORMATION: /note="Nucleotide may be methylated to form 5-methylcytosine"

<400> SEQUENCE: 150
ggcttgtccg atttgcacgg tgacttgatt acactctctc attcatggtc acttccgaag 60
cgctttagtg ccttccgtcc ctaaaccgcc aacagccaga acggcttctc cccgcggttt 120
gt 122

<210> SEQ ID NO 151

<400> SEQUENCE: 151

000

<210> SEQ ID NO 152
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 152
ttggaggatt agtattygat tatgttgaa 29

<210> SEQ ID NO 153
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 153
cctcaactta aatacatctc ctcc 24

<210> SEQ ID NO 154
<211> LENGTH: 16
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 154

ggggtggggt ggattt                                              16


<210> SEQ ID NO 155
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155

cctcctccca aacccttct                                           19


<210> SEQ ID NO 156
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156

gtttagggtt ttagtggtgg t                                        21


<210> SEQ ID NO 157
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157

ggaaatyggg aggtttttgt gta                                      23


<210> SEQ ID NO 158
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158

atctctactt aaaaattaac caccc                                    25


<210> SEQ ID NO 159
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159

rccttaccaa attcctcaca a                                        21


<210> SEQ ID NO 160
```

<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 160
tttggttggt tgagttatag tttt 24

<210> SEQ ID NO 161
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 161
ggyggggtgg ggtgga 16

<210> SEQ ID NO 162
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 162
rttttcacta ctccaactcc c 21

<210> SEQ ID NO 163
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 163
tttggaaaag tygggaggga g 21

<210> SEQ ID NO 164
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 164
yggaatttat taaaagtgat ttataaaggt 30

<210> SEQ ID NO 165
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 165

```
cccaaaactt aatcaaaaac cct                                             23


<210> SEQ ID NO 166
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166

cctcctcrct ctcttataaa aacaaaact                                       29


<210> SEQ ID NO 167
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167

ggggaatttt ggaggatgta tt                                              22


<210> SEQ ID NO 168
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168

ggggattaag ggattgttta ttttg                                           25


<210> SEQ ID NO 169
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 169

gtttagtgty ggtgttaatg atagatg                                         27


<210> SEQ ID NO 170
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 170

aggtttagat ttgtggggtt ta                                              22


<210> SEQ ID NO 171
<211> LENGTH: 20
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic primer"

<400> SEQUENCE: 171
ttaaagatga gtgggggagg 20

<210> SEQ ID NO 172
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
aaagtaatta aggtygtagt gattggt 27

<210> SEQ ID NO 173
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
gggttatygg tttttagttt gggtg 25

<210> SEQ ID NO 174
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174
agtttggtta ggagttttga gt 22

<210> SEQ ID NO 175
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
cctacactcc cccacaaaa 19

<210> SEQ ID NO 176
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
ygggggaaaa tgtttttatt ga 22

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 177
cctcacaaaa acccccaaaa 20

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 178
tatttggygg gtggggagaa 20

<210> SEQ ID NO 179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 179
acctctaaca actaccccct 20

<210> SEQ ID NO 180
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 180
ccacccaaaa cccaacrtca aatta 25

<210> SEQ ID NO 181
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 181
gtttgtyggg gaggttggtt t 21

<210> SEQ ID NO 182
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 182
cctcttcctt ccttccaaat c 21

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 183
gggaaaggat aagggaaggg 20

<210> SEQ ID NO 184
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 184
agagttgttt ttgattgtaa ggga 24

<210> SEQ ID NO 185
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185
accactcacc crcacaaaca c 21

<210> SEQ ID NO 186
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 186
rtataaaaac aaaacacatc ctattaac 28

<210> SEQ ID NO 187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 187
ggggygggtt agggagtatt t 21

<210> SEQ ID NO 188
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 188
aaattgtagt ttgttaggtt gagt 24

<210> SEQ ID NO 189
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 189
aaaaataaaa attctcctca taactacaa 29

<210> SEQ ID NO 190
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 190
aaaaacttaa taccratact aataacaaat aaac 34

<210> SEQ ID NO 191
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 191
aactcccraa ccaccccc 18

<210> SEQ ID NO 192
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 192
ctctccrccc cctccccta 19

<210> SEQ ID NO 193
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 193
ctcaaaacta ctaaactcta cccta 25

```
<210> SEQ ID NO 194
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 194

gggaggyggg ttatggtttg g                                              21


<210> SEQ ID NO 195
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 195

tttgagaaat gtgaattagt tatttgt                                        27


<210> SEQ ID NO 196
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 196

ttggatgggt yggtgggatg                                                20


<210> SEQ ID NO 197
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 197

accacaacta actcttaata tcct                                           24


<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198

aactacccra aacccctcct                                                20


<210> SEQ ID NO 199
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 199
aaaatctaac ratccccaac tacc 24

<210> SEQ ID NO 200
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 200
gggggtattt agggtaggtt g 21

<210> SEQ ID NO 201
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 201
ygtttggaaa gaaatggagg ta 22

<210> SEQ ID NO 202
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 202
caaaaacctt cccacaccc 19

<210> SEQ ID NO 203
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 203
aaaacccaaa caccrcccaa aa 22

<210> SEQ ID NO 204
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 204
gggggttttg gttttgattt ag 22

<210> SEQ ID NO 205
<211> LENGTH: 22
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 205

aagattgagt tttgggtttg tt                                                22


<210> SEQ ID NO 206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206

gaaggggygg ggtttaggag                                                   20


<210> SEQ ID NO 207
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207

ttctcctcct acrcctacta cct                                               23


<210> SEQ ID NO 208
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208

gtaggttaat aaaaggaggg gag                                               23


<210> SEQ ID NO 209
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209

attatttatg gtgagttgyg agaatagt                                          28


<210> SEQ ID NO 210
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210

gggggttggt ggaatttg                                                     18
```

<210> SEQ ID NO 211
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 211
tctccaccct ccccct 16

<210> SEQ ID NO 212
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 212
agttagttat ggaagtaggg gt 22

<210> SEQ ID NO 213
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 213
gatattatta tttatggtga gttgygagaa ta 32

<210> SEQ ID NO 214
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 214
agtttyggtt gtggttttgg ga 22

<210> SEQ ID NO 215
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 215
ggatgatatt atttggtttt gtttagag 28

<210> SEQ ID NO 216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 216
ggggaggtta gggataggtt 20

<210> SEQ ID NO 217
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 217
caaccttcac tccaaccct 19

<210> SEQ ID NO 218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 218
ggggaaygtg gaaaggaggg 20

<210> SEQ ID NO 219
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 219
aaaaatacrc ctcaaaaacc aaataaaaac 30

<210> SEQ ID NO 220
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 220
gtgttgtata gtgtgaggga a 21

<210> SEQ ID NO 221
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 221
raaaaccaat aaactaccaa ctc 23

<210> SEQ ID NO 222
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 222

gtttttgtty gtgtgtttgg gtg                                              23


<210> SEQ ID NO 223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223

tggggttggg atttttaggt                                                  20


<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224

gagttttggt aggtgttggt                                                  20


<210> SEQ ID NO 225
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225

ctctacaaaa taaaatcaaa aacacca                                          27


<210> SEQ ID NO 226
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226

tctatactca ctttctccaa tactt                                            25


<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
```

```
aacaaacaaa aacccccaca                                                  20


<210> SEQ ID NO 228
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228

caactccaaa taccrttata cctacccta                                        29


<210> SEQ ID NO 229
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229

tggattgygg ttatagtttt tgttttagg                                        29


<210> SEQ ID NO 230
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230

ccctaactaa ctaaactaca actcc                                            25


<210> SEQ ID NO 231
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231

tctaaaaatt aactctaact tcccca                                           26


<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232

tgttgttgtt gtgtttgggg                                                  20


<210> SEQ ID NO 233
<211> LENGTH: 30
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic primer"

<400> SEQUENCE: 233
raaaacaaaa tcaattacta tttttcatct 30

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 234
ggggaggygg gtttagtgta g 21

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 235
ttaaagttgt tgagttttgt tttga 25

<210> SEQ ID NO 236
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 236
tcctaaccca aacctaaaca aa 22

<210> SEQ ID NO 237
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 237
tcaaaataaa aactcctcca cctat 25

<210> SEQ ID NO 238
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 238
tgtaggtatg gttygaggag gt 22

<210> SEQ ID NO 239

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 239
gtgagggaag agaggtgttt 20

<210> SEQ ID NO 240
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 240
tgtagttatt ttaggggaag taatagat 28

<210> SEQ ID NO 241
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 241
ggtaggggyg ggggtgg 17

<210> SEQ ID NO 242
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 242
rttcaacctc ctaaacaaaa acaa 24

<210> SEQ ID NO 243
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 243
acccatccta caaacataac tc 22

<210> SEQ ID NO 244
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 244
gaagatttyg gggaaggagt gg 22

<210> SEQ ID NO 245
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 245
acttcctttc tttataacca cctc 24

<210> SEQ ID NO 246
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 246
raaaaacaaa acaattcaaa tcaa 24

<210> SEQ ID NO 247
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 247
ggaagatgyg ttttaagaat taggtagaa 29

<210> SEQ ID NO 248
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 248
gggtyggggt attttagttt ttgt 24

<210> SEQ ID NO 249
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 249
gaggtttggg gattggttg 19

<210> SEQ ID NO 250
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 250
ccctcttccc tctcttaaca c 21

<210> SEQ ID NO 251
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 251
aaaactacta ccccaacaaa ac 22

<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 252
ggggaaggga gaygtgtgta 20

<210> SEQ ID NO 253
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 253
cccaccrcct attacaacca aaac 24

<210> SEQ ID NO 254
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 254
accttaaaat taaaatccct aaatacaac 29

<210> SEQ ID NO 255
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 255
rcttaaaatc actaaaaata taccaac 27

<210> SEQ ID NO 256
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 256
gtgtaagttt tygtagtgta gtggt 25

<210> SEQ ID NO 257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 257
tcccaaaatc ccacactaca 20

<210> SEQ ID NO 258
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 258
acttaattac actctctcat tcataatc 28

<210> SEQ ID NO 259
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 259
rcaacttcta ccttttatta caaac 25

<210> SEQ ID NO 260
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 260
aatttttatt tgattatgaa tagaggtaat tt 32

<210> SEQ ID NO 261
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 261
ggggattgag tgttagggg 19

<210> SEQ ID NO 262
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 262
ccaccctacr atccccatta ac 22

<210> SEQ ID NO 263
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 263
tctactctac ctacrccctc attaaa 26

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 264
craaatcctc cctcctacct c 21

<210> SEQ ID NO 265
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 265
cacaaaccca aaaacccca 19

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 266
gttaggagta ggtagggtgt 20

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 267
gtgaggttga tattagagag gat 23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 268
rcaaaaacta aatcccccaa aaa 23

<210> SEQ ID NO 269
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 269
ttgaggggga tgtatatttg tatt 24

<210> SEQ ID NO 270
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 270
ractctatcc accaccaa 18

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 271
aaccattata aattcacccc aac 23

<210> SEQ ID NO 272
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 272
ggtaaaggtt taggaaaggg ag 22

<210> SEQ ID NO 273
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 273
aaacctaatt crtttcaccc aaactatc 28

<210> SEQ ID NO 274
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 274
tccaccraat cctaaatata caataaaaa 29

<210> SEQ ID NO 275
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 275
ttaaggagag gggyggttag tt 22

<210> SEQ ID NO 276
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 276
acattttcat aacctcctac aataaa 26

<210> SEQ ID NO 277
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 277
ctacaaaacr aaaacaaaac acaaaataa 29

<210> SEQ ID NO 278
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 278
aaccaattcr ctaacctttc taacatc 27

<210> SEQ ID NO 279
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 279
ccttaaacta aaaactacac raactaaaat 30

<210> SEQ ID NO 280
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 280
agtgttgaat tgatgttgga aa 22

<210> SEQ ID NO 281
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 281
tctacacccc ctcccc 16

<210> SEQ ID NO 282
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 282
tttttgatta tttaggagtt tggttg 26

<210> SEQ ID NO 283
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 283
aaacacaaat acaaaactat acataact 28

<210> SEQ ID NO 284
<211> LENGTH: 18
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 284

ccccraaccc aaccaaca                                                18


<210> SEQ ID NO 285
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 285

ggatgtgtag tggagggg                                                18


<210> SEQ ID NO 286
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 286

gggggtagta ttgggggt                                                18


<210> SEQ ID NO 287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 287

cccaactaac accaaaacct t                                            21


<210> SEQ ID NO 288
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 288

tccaatcccc cacccc                                                  16


<210> SEQ ID NO 289
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 289

atcctaaacc taaacaacca aaaa                                         24
```

<210> SEQ ID NO 290
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 290
ccaaaacccc aaactccaa 19

<210> SEQ ID NO 291
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 291
rctctcacct aaaccccc 18

<210> SEQ ID NO 292
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 292
gttattgatg tgttttgaat gagtt 25

<210> SEQ ID NO 293
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 293
acaccccraa ccccaaaac 19

<210> SEQ ID NO 294
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 294
ccaacaccct aacraaacct aaac 24

<210> SEQ ID NO 295
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 295
gttagtttgt agttgygggg ttattta 27

<210> SEQ ID NO 296
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 296
acaatacatt crtatcatca cccacc 26

<210> SEQ ID NO 297
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 297
aaatctaccc caccctacc 19

<210> SEQ ID NO 298
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 298
gtttttatta tttggaaaag gaaggtt 27

<210> SEQ ID NO 299
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 299
ccaaaacaaa ctaatcttaa acctaaa 27

<210> SEQ ID NO 300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 300
ccctctttcc ccttcaatct t 21

<210> SEQ ID NO 301
<211> LENGTH: 33

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 301

atcatctttc cttataatcr caaatcttaa aaa                              33


<210> SEQ ID NO 302
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 302

acttctttaa tatcaaaatc cratcttcc                                   29


<210> SEQ ID NO 303
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 303

atactttcta acccctctcr aaaaata                                     27


<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 304

acccrcatct accctcacct                                             20


<210> SEQ ID NO 305
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 305

caataacrcc ccaacccccca c                                          21


<210> SEQ ID NO 306
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 306
```

ctaaaacaca aaaactacaa acact 25

<210> SEQ ID NO 307
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 307
yggggtgggt tgggg 15

<210> SEQ ID NO 308
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 308
agaggttatt gttttagttt aggttt 26

<210> SEQ ID NO 309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 309
actcctcccc ctatacaaac 20

<210> SEQ ID NO 310
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 310
aaaccctaca acccctcc 18

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 311
ggaaaggata agggaagggt 20

<210> SEQ ID NO 312
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
agtgagagaa agttttgtag tttt 24

<210> SEQ ID NO 313
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313
gggyggggtt ttgtttttgg t 21

<210> SEQ ID NO 314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314
acaatacccr ctcccccacc 20

<210> SEQ ID NO 315
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 315
ratcaacttc taaaaataac caaaaa 26

<210> SEQ ID NO 316
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 316
gtggttttat atagtttgtt ggttg 25

<210> SEQ ID NO 317
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 317
tctaaactta ttttcaactt atttaattca c 31

<210> SEQ ID NO 318

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 318

gatgaggttg gttaggtgtt                                              20


<210> SEQ ID NO 319
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 319

ccctcaactc craatccaaa ac                                           22


<210> SEQ ID NO 320
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 320

cttctatacc tacaaatact aaataacaaa                                   30


<210> SEQ ID NO 321
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 321

aaaccratat accctaaaaa cccc                                         24


<210> SEQ ID NO 322
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 322

racaaaccct cccaaca                                                 17


<210> SEQ ID NO 323
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 323
```

tgtttgagtg tttgtttgta gat 23

<210> SEQ ID NO 324
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 324
ggttgtagga tagggttatg ttg 23

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 325
ggagggggta gagttttagg 20

<210> SEQ ID NO 326
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 326
atgttgaggg tgttayggtt ttatt 25

<210> SEQ ID NO 327
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 327
gtttattgag gtgtatgtta ggtataat 28

<210> SEQ ID NO 328
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 328
aattcatttt acctttcata taataaaacc 30

<210> SEQ ID NO 329
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 329

gggttggggg tagyggaaaa t                                                21


<210> SEQ ID NO 330
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 330

gttgggttgg ggttgga                                                     17


<210> SEQ ID NO 331
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 331

cctccccact aacctcac                                                    18


<210> SEQ ID NO 332
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 332

tcccttccct accaaactc                                                   19


<210> SEQ ID NO 333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 333

ccctccacaa acctaccaaa                                                  20


<210> SEQ ID NO 334
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334

ccaatccrcc caccccaata ac                                               22
```

<210> SEQ ID NO 335
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 335
agtggagtag tgtattygtg ttattattta 30

<210> SEQ ID NO 336
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 336
gggatgggga aattatttga ttag 24

<210> SEQ ID NO 337
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 337
gatttttagg aggtttygaa ttatttagtt t 31

<210> SEQ ID NO 338
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 338
gtaggtatag tgggygggta gg 22

<210> SEQ ID NO 339
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 339
cccctttacr cacctccttc tt 22

<210> SEQ ID NO 340
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 340
aaccaatatc cractatact aaaaccta 28

<210> SEQ ID NO 341
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 341
ccaataataa ccatcaccrt acccaa 26

<210> SEQ ID NO 342
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 342
tttatttttg ygggggaata taaggag 27

<210> SEQ ID NO 343
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 343
caacaaaact caaaacattc cc 22

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 344
ggggatygtg ggatttggtt 20

<210> SEQ ID NO 345
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 345
gggaattggt aaagggtttt tag 23

<210> SEQ ID NO 346
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 346
ccatcaaaaa taacccacaa aaac 24

<210> SEQ ID NO 347
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 347
gggygttgag gagggtgg 18

<210> SEQ ID NO 348
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 348
atttgttata gtaatgggat gataaatg 28

<210> SEQ ID NO 349
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 349
agttatygat ttttgtaagg gatgtaga 28

<210> SEQ ID NO 350
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 350
aaggtygaga tttgggtttg ttag 24

<210> SEQ ID NO 351
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 351
tttgttgttt ttatttgygg tttggt 26

<210> SEQ ID NO 352
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 352
raactccaac accttaacc 19

<210> SEQ ID NO 353
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 353
ggtaggaaga agggygatgt tttt 24

<210> SEQ ID NO 354
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 354
actaaacaaa ccatcaaaac cc 22

<210> SEQ ID NO 355
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 355
ttttaagggt ttgttttaga gtttg 25

<210> SEQ ID NO 356
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 356
agttgggatt tgaggaaatt tag 23

<210> SEQ ID NO 357
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 357
aatcaattac tatttttcat ctttaacaaa a 31

<210> SEQ ID NO 358
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 358
acttcaaaaa tttactccaa aacct 25

<210> SEQ ID NO 359
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 359
aatacaacrc aaatacaacc aaccc 25

<210> SEQ ID NO 360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 360
gggtgtatag gtttaggggt 20

<210> SEQ ID NO 361
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 361
cctccccraa actccaacta t 21

<210> SEQ ID NO 362
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 362
tcttttattc ccaattcrac tttcttt 27

<210> SEQ ID NO 363
<211> LENGTH: 19
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 363
agtttttagg gagggggag 19

<210> SEQ ID NO 364
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 364
ygatgttttg tttgggtttg g 21

<210> SEQ ID NO 365
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 365
gttgggttgg gagaagttt 19

<210> SEQ ID NO 366
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 366
gggttttgty gtagtttagt tttagg 26

<210> SEQ ID NO 367
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 367
tttagggttt tagtggtggt t 21

<210> SEQ ID NO 368
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 368
ggagtyggag aaagggtgat t 21

<210> SEQ ID NO 369
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 369
catctcaacc ttccaaatac taaa 24

<210> SEQ ID NO 370
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 370
tggygtgttt ttgtttattg gagtatt 27

<210> SEQ ID NO 371
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 371
acaatccraa aacaacaact acact 25

<210> SEQ ID NO 372
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 372
atttaaaaca caaaacataa aaatatctac ta 32

<210> SEQ ID NO 373
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 373
ggaggtaggt ttygggaaag g 21

<210> SEQ ID NO 374
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 374
acccatcccc taacctaac 19

<210> SEQ ID NO 375
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 375
cccacaccca cccac 15

<210> SEQ ID NO 376
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 376
aaaatactac rtaacaacat acaaaacatc ac 32

<210> SEQ ID NO 377
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 377
tgtgttttgg gttattttgt gtt 23

<210> SEQ ID NO 378
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 378
aaaattctac taaaaatcat tctatctcc 29

<210> SEQ ID NO 379
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 379
ggatttaggg ttatgttggg ag 22

<210> SEQ ID NO 380
<211> LENGTH: 25

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 380
gttgtagaay gggagtaggg tatag 25

<210> SEQ ID NO 381
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 381
ggaggttttt gtygtgggga ata 23

<210> SEQ ID NO 382
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 382
cacaaaccra aaataaaaac tctaaacc 28

<210> SEQ ID NO 383
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 383
ctaacaaaac racccaacca aaaa 24

<210> SEQ ID NO 384
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 384
ttagayggta ttaggtagtt gaatttagt 29

<210> SEQ ID NO 385
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 385
ggttagtaag aatgttatag ttttattttg t 31

<210> SEQ ID NO 386
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 386
aacaatctat aaatactttc racacaact 29

<210> SEQ ID NO 387
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 387
aaaactaaaa attcctaaaa tcccttta 28

<210> SEQ ID NO 388
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 388
caacaaataa tccccraaca cca 23

<210> SEQ ID NO 389
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 389
rtttccctac acccaacac 19

<210> SEQ ID NO 390
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 390
gggttttygt ttggagggtt gt 22

<210> SEQ ID NO 391
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 391
ggggtgtggg tggtttt 17

<210> SEQ ID NO 392
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 392
racccctcca accttt 16

<210> SEQ ID NO 393
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 393
gggaagtggt aatttgtgga ta 22

<210> SEQ ID NO 394
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 394
tgtttggtgg tttgttygat ttgta 25

<210> SEQ ID NO 395
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 395
cttccctctc tccttccttt a 21

<210> SEQ ID NO 396
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 396
caaactacta ccccttcaac t 21

<210> SEQ ID NO 397

<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 397
tttttgataa agtaattaag gtygtagtga 30

<210> SEQ ID NO 398
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 398
atttcttaac cacccaaaaa ctta 24

<210> SEQ ID NO 399
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 399
attaaggttt taayggagaa ggtatgt 27

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 400
cccctaacrc catcccaacc 20

<210> SEQ ID NO 401
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 401
gaaaagatat tttgtggggg att 23

<210> SEQ ID NO 402
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 402
ygagggggtt ttagggt 17

<210> SEQ ID NO 403
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 403
accctaaacc taccacctaa c 21

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 404
tcctcctact cccaaaatct 20

<210> SEQ ID NO 405
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 405
aatccrctaa aactctaaaa taacaccc 28

<210> SEQ ID NO 406
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 406
ttgttggtat ttttgttttt ggg 23

<210> SEQ ID NO 407
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 407
ctcaaatctc aattactctc aaaataaa 28

<210> SEQ ID NO 408
<211> LENGTH: 24
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 408

tgttgatagg tgtaggtagg atag                                        24


<210> SEQ ID NO 409
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 409

ccaccaaatt attacataaa atctacaa                                    28


<210> SEQ ID NO 410
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 410

aaaacrcccc aaacaccaaa taaaa                                       25


<210> SEQ ID NO 411
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 411

ttttggattg ggttagggta tt                                          22


<210> SEQ ID NO 412
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 412

gattttyggg gtgggtggg                                              19


<210> SEQ ID NO 413
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 413

acaacrattt ccaaattcct actaac                                      26
```

<210> SEQ ID NO 414
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 414
rctcaaatct caattactct caaa 24

<210> SEQ ID NO 415
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 415
tgattgtaag ygtaggtttg ggt 23

<210> SEQ ID NO 416
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 416
caacaataca ctatacract cctacaa 27

<210> SEQ ID NO 417
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 417
acccctttcr ctcccttcct a 21

<210> SEQ ID NO 418
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 418
agagatggga agagaaagtg g 21

<210> SEQ ID NO 419
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 419
ttttattttt ygtgaaagta atgatatagt agaa 34

<210> SEQ ID NO 420
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 420
atcctaaccc taaaatccct aaat 24

<210> SEQ ID NO 421
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 421
ccttctcaat aaatacattt acccc 25

<210> SEQ ID NO 422
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 422
aataaccacc accrctcctc c 21

<210> SEQ ID NO 423
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 423
rccacctttc ttaaataact ct 22

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 424
ccccaaatca acccttttc 20

<210> SEQ ID NO 425
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 425
rcctatttat aataataatc aaaccca 27

<210> SEQ ID NO 426
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 426
ratcccacct actaatattc c 21

<210> SEQ ID NO 427
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 427
acctcracac caccaaaaat aaa 23

<210> SEQ ID NO 428
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 428
tgaggggaga tttgagggat 20

<210> SEQ ID NO 429
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 429
aattcccraa ccccctccc 19

<210> SEQ ID NO 430
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 430
ggaaaatttt tagtatttga gaatgga 27

<210> SEQ ID NO 431
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 431
tcraaatccc aaaaccacaa cc 22

<210> SEQ ID NO 432
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 432
tttttgggat tgtggtggag 20

<210> SEQ ID NO 433
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 433
gggtggatyg tgggttagtt tt 22

<210> SEQ ID NO 434
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 434
aaccaccact aaaaccctaa a 21

<210> SEQ ID NO 435
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 435
ggtgtgtgtg tgtaatataa taatttgt 28

<210> SEQ ID NO 436
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 436
acaaaccaac cacatttact tct 23

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 437
aaaaccacct tcctaactcc 20

<210> SEQ ID NO 438
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 438
atggaggttt aggtyggtgt aaa 23

<210> SEQ ID NO 439
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 439
ttatgggggy gggtgatgga 20

<210> SEQ ID NO 440
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 440
acttcccrcc caaccaactt c 21

<210> SEQ ID NO 441
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 441
acccatctcc ccraaaacta at 22

<210> SEQ ID NO 442
<211> LENGTH: 22
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 442
gaaatgagtt tggtaggtgg tt 22

<210> SEQ ID NO 443
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 443
ggtggaggag gtggtgatta 20

<210> SEQ ID NO 444
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 444
ygttgattat ggttggtttg tt 22

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 445
gaggggtttt gagggttgta 20

<210> SEQ ID NO 446
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 446
tgaattttat tgttatgtgg ggtatt 26

<210> SEQ ID NO 447
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 447
raaaatacac ctaaaacaaa aactat 26

<210> SEQ ID NO 448
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 448 acttttaac atctatttta ctaacctatt 30

<210> SEQ ID NO 449
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 449
ccctttcccr ctccactact c 21

<210> SEQ ID NO 450
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 450
gggtggtggt aatttggtt 19

<210> SEQ ID NO 451
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 451
tggttgggyg gtaagtatta tgttg 25

<210> SEQ ID NO 452
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 452
agggttagag tttttgggtt ag 22

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 453
ccctcccrac caaaaactca 20

<210> SEQ ID NO 454
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 454
acaacaaccr aataatcccc attc 24

<210> SEQ ID NO 455
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 455
ttatatttgt ttttgggagg agtg 24

<210> SEQ ID NO 456
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 456
tggttyggat tggggtagga t 21

<210> SEQ ID NO 457
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 457
cctcccracc ctcctccc 18

<210> SEQ ID NO 458
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 458
tcctaatttc ttacctcatt acact 25

<210> SEQ ID NO 459
<211> LENGTH: 30

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 459
acaaaataaa aactccraaa ataaaatccc 30

<210> SEQ ID NO 460
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 460
gtggtgtygg tttttaaggg tt 22

<210> SEQ ID NO 461
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 461
acccaaccct acttaactct c 21

<210> SEQ ID NO 462
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 462
acccracttc ctttatcccc a 21

<210> SEQ ID NO 463
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 463
actaaaaccc ctaaaccaac c 21

<210> SEQ ID NO 464
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 464
ggtgggtggg aagtaggat 19

<210> SEQ ID NO 465
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 465
raaataaatc taataaataa ttttcccc 28

<210> SEQ ID NO 466
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 466
racttccttt atccccaatc ta 22

<210> SEQ ID NO 467
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 467
tctctcctcc ccaaccrtct aaaa 24

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 468
atcaaattcc ccaaaaccct 20

<210> SEQ ID NO 469
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 469
ttaaaaatcc ccaccaacaa c 21

<210> SEQ ID NO 470
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 470
ggttagtagg ttgtttagga gg 22

<210> SEQ ID NO 471
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 471
rtaaaactaa actccaactc cc 22

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 472
ttgggagtyg gggtggttag 20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 473
caatccctat aaccccctcc 20

<210> SEQ ID NO 474
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 474
ygattttagg tttagggtga atttt 25

<210> SEQ ID NO 475
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 475
ccacccacct ctacctaat 19

<210> SEQ ID NO 476

<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 476
aaaactaatt cctacraatt cctccta 27

<210> SEQ ID NO 477
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 477
aacctcttta aaaccttccc taa 23

<210> SEQ ID NO 478
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 478
agaaatattt tagtgtgaat taaataagtt g 31

<210> SEQ ID NO 479
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 479
tgggggtagg gggagtt 17

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 480
gttgtgggyg ggtaggaggt 20

<210> SEQ ID NO 481
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 481
tgggagggat tygagttggt tg 22

<210> SEQ ID NO 482
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 482
ccaccaaacc crccaactac c 21

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 483
taggttgggt aaaggaagga 20

<210> SEQ ID NO 484
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 484
ggtttttatt tttygttttt atttgatgag tt 32

<210> SEQ ID NO 485
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 485
tcaatccaac tctactcacc at 22

<210> SEQ ID NO 486
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 486
ygtttgttta tagtgataat taggttta 28

<210> SEQ ID NO 487
<211> LENGTH: 29
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic primer"

<400> SEQUENCE: 487
cctaaccaaa aaccraattt aatttaacc 29

<210> SEQ ID NO 488
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 488
acctccccat actttaatcc t 21

<210> SEQ ID NO 489
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 489
aagtttggga gtaaggaggg 20

<210> SEQ ID NO 490
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 490
ttttggtttt yggtttggag gg 22

<210> SEQ ID NO 491
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 491
aaaaccraaa ctaaataaca aaataaactt c 31

<210> SEQ ID NO 492
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 492
caaaccaaaa cccaacatca c 21

<210> SEQ ID NO 493
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 493
aaccctacaa ttaaacacaa acat 24

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 494
rcaaacacct accaaaacca 20

<210> SEQ ID NO 495
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 495
gtagtattag ygagtttatt aggaaggag 29

<210> SEQ ID NO 496
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 496
gaggttgaat ggtaaagtag gtt 23

<210> SEQ ID NO 497
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 497
aaataaattt ccaaaaacca aacaaaa 27

<210> SEQ ID NO 498
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 498
tgagtataag tatgttgtat gggg 24

<210> SEQ ID NO 499
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 499
ygttttaggt ttaggaagtt gaatg 25

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 500
ctctccccct ccctaaaaat 20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 501
cacctcctcc craaaaccct 20

<210> SEQ ID NO 502
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 502
cctcctcttt cctcccaa 18

<210> SEQ ID NO 503
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 503
tttttaatat ttattttgtt gatttgtttg g 31

<210> SEQ ID NO 504
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 504
ttgggtgatt gggggtt 17

<210> SEQ ID NO 505
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 505
caaaaactac aaaaacatcr ctaaatatta cc 32

<210> SEQ ID NO 506
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 506
gtgggyggga attttaaggg g 21

<210> SEQ ID NO 507
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 507
gttggggagg gttggtt 17

<210> SEQ ID NO 508
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 508
gagataaygg ggtttttggg aag 23

<210> SEQ ID NO 509
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 509
ccaaataaaa ataataataa aatattccaa act 33

<210> SEQ ID NO 510
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 510
ggtttatatt taaggttagg aagaagg 27

<210> SEQ ID NO 511
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 511
agatgagggg agaggtgg 18

<210> SEQ ID NO 512
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 512
ggaaaggagg gttaygggta aag 23

<210> SEQ ID NO 513
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 513
cctcctaaac taaactaaaa cactaac 27

<210> SEQ ID NO 514
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 514
accctctcct cctctcc 17

<210> SEQ ID NO 515
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 515
ygggagaagt ttttgggtt 19

<210> SEQ ID NO 516
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 516
ttgttyggaa aaattgtttg ggttt 25

<210> SEQ ID NO 517
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 517
gggtgggata ggatagggt 19

<210> SEQ ID NO 518
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 518
gagtagagtg taggttygaa ggtat 25

<210> SEQ ID NO 519
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 519
ccaaaacaaa aatctaacta craaaatcc 29

<210> SEQ ID NO 520
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 520
aaccttaaaa cccaaaccaa c 21

<210> SEQ ID NO 521
<211> LENGTH: 26
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 521

gaaaatygat gagaggtagg gttaag                                        26


<210> SEQ ID NO 522
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 522

aaaaatccca aaccaaaaac taac                                          24


<210> SEQ ID NO 523
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 523

gtagtgtatt gtgtggtttt tgt                                           23


<210> SEQ ID NO 524
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 524

tttgggtaag ttttgaggaa ag                                            22


<210> SEQ ID NO 525
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 525

ctccaaaaac accttaaaaa cac                                           23


<210> SEQ ID NO 526
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 526

ggaagttagg taatttttga agttttt                                       27
```

<210> SEQ ID NO 527
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 527
yggaggtttt gagttatgga 20

<210> SEQ ID NO 528
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 528
raattaaaac caaaaaccaa aaat 24

<210> SEQ ID NO 529
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 529
tttggttttg gttgaygttg agt 23

<210> SEQ ID NO 530
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 530
ggtggtggtt tggggt 16

<210> SEQ ID NO 531
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 531
ggggtagttt tygtagagtg gag 23

<210> SEQ ID NO 532
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 532
ggttattatt ggggttttgg gtaa 24

<210> SEQ ID NO 533
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 533
acaacacaac aatttatcaa ctact 25

<210> SEQ ID NO 534
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 534
ggtttagtta ttagggttta gtggt 25

<210> SEQ ID NO 535
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 535
ctttcctctc tctctctctc t 21

<210> SEQ ID NO 536
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 536
ggattagtgg ttttgtttgg aaaa 24

<210> SEQ ID NO 537
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 537
gggtaygtta gagtgtgttt tattattag 29

<210> SEQ ID NO 538
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 538

ccttcctcct aaaaccctaa aat                                           23


<210> SEQ ID NO 539
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 539

aatcctcaaa aattctattc ttaaacc                                       27


<210> SEQ ID NO 540
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 540

atgttggggg tggaatttt                                                19


<210> SEQ ID NO 541
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 541

ggtggttagt gtattgygga gttg                                          24


<210> SEQ ID NO 542
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 542

gttaggagtt agaagttggt gt                                            22


<210> SEQ ID NO 543
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 543
```

```
ttttaggtga ttgygaggta atttgt                                          26


<210> SEQ ID NO 544
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 544

gttgtagttg ttttayggta ttgttga                                         27


<210> SEQ ID NO 545
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 545

aaaaccccaa taaatttcaa atcc                                            24


<210> SEQ ID NO 546
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 546

aatggggaty gtagggtggg                                                 20


<210> SEQ ID NO 547
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 547

ggatttttag ggattaagta aagaaattat                                      30


<210> SEQ ID NO 548
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 548

caaaccctcc acrcttctac aaaaa                                           25


<210> SEQ ID NO 549
<211> LENGTH: 23
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic primer"

<400> SEQUENCE: 549
tggtttagtt tgggyggaga gta 23

<210> SEQ ID NO 550
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 550
ggaaggggga taggggat 18

<210> SEQ ID NO 551
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 551
aaaacaataa cacaacaaaa acca 24

<210> SEQ ID NO 552
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 552
ggtttygtgt ggttggggg 19

<210> SEQ ID NO 553
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 553
tgaggtttgt agtgaagggt 20

<210> SEQ ID NO 554
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 554
tggtygtgga tttgattttt gtagt 25

<210> SEQ ID NO 555

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 555

agaggatatg taaattttta gaatgttg                                        28


<210> SEQ ID NO 556
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 556

gtgygatagg gatttttatt tttaggttta                                      30


<210> SEQ ID NO 557
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 557

gggaagyggg gttgtaggta                                                 20


<210> SEQ ID NO 558
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 558

ggagatgggg gatattttay gttagtt                                         27


<210> SEQ ID NO 559
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 559

ttgatgtttt gtagggatgg a                                               21


<210> SEQ ID NO 560
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 560
```

cctaccccct acttccca 18

<210> SEQ ID NO 561
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 561
caacactaac raatccacca aaaa 24

<210> SEQ ID NO 562
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 562
tgtatttgag gtagaagttg tgg 23

<210> SEQ ID NO 563
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 563
gtttaggtga ttttgatttt aggtttt 27

<210> SEQ ID NO 564
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 564
tccaaaactt tcaacaccat ac 22

<210> SEQ ID NO 565
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 565
aaccctaatc ccaaattccc 20

<210> SEQ ID NO 566
<211> LENGTH: 29
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 566
ctccacctcc rttcctaaaa ctataataa 29

<210> SEQ ID NO 567
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 567
agttttattt gtagtagtyg aatggtttt 29

<210> SEQ ID NO 568
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 568
yggaggtggg gagtagtt 18

<210> SEQ ID NO 569
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 569
ctaataaaat cttaactact ccaaatcaa 29

<210> SEQ ID NO 570
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 570
gtgagaagga gaggggag 18

<210> SEQ ID NO 571
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 571
tccaaatccc craaaccctc 20

<210> SEQ ID NO 572
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 572
gtttagygta gatggggtgg ga 22

<210> SEQ ID NO 573
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 573
ggtgatgagg ttgatgtagt gt 22

<210> SEQ ID NO 574
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 574
aattattttt aaagtggggg tagtat 26

<210> SEQ ID NO 575
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 575
ggagggatag gagygagagg g 21

<210> SEQ ID NO 576
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 576
acccaaaact caatcttact tct 23

<210> SEQ ID NO 577
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 577
ataaatctaa taaataattt tccccacc 28

<210> SEQ ID NO 578
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 578
ccccaaaccc aaaataaact tc 22

<210> SEQ ID NO 579
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 579
cacctaccaa atttacaaat ccc 23

<210> SEQ ID NO 580
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 580
cccraaaccc cacacatact t 21

<210> SEQ ID NO 581
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 581
tttgggtgga ggttatgga 19

<210> SEQ ID NO 582
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 582
aacaaccraa cccaccaaaa a 21

<210> SEQ ID NO 583
<211> LENGTH: 24
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 583

acactcraca cacttaaaac aaac                                             24


<210> SEQ ID NO 584
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 584

gaaggagagg ggttggg                                                     17


<210> SEQ ID NO 585
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 585

ggtttgtagt tttggttata gttgt                                            25


<210> SEQ ID NO 586
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 586

gaaggtagag aatttgggtt ttt                                              23


<210> SEQ ID NO 587
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 587

ttgagtgtgt taggygtttg ttg                                              23


<210> SEQ ID NO 588
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 588

rctccaataa cccaacctaa                                                  20
```

<210> SEQ ID NO 589
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 589
cctatttcta cccccaccc 19

<210> SEQ ID NO 590
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 590
cccttctcra tcaaaaacat cctac 25

<210> SEQ ID NO 591
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 591
aatcaacrac ttaaacattc aaattaaact 30

<210> SEQ ID NO 592
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 592
gttgygtttg ttagtgtagg aagtt 25

<210> SEQ ID NO 593
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 593
ggaaaattgg aggtagggg 19

<210> SEQ ID NO 594
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 594
ggagtgattt atgygttatt gttttgt 27

<210> SEQ ID NO 595
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 595
aaactacacc craaaacctc taaat 25

<210> SEQ ID NO 596
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 596
gaggttttta tagggtagga ttagt 25

<210> SEQ ID NO 597
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 597
aacaacaact aatccraact aataaaaac 29

<210> SEQ ID NO 598
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 598
aaaaccacct actaaaaccr aaaataa 27

<210> SEQ ID NO 599
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 599
gggtaaagaa gaggagaaga taaa 24

<210> SEQ ID NO 600
<211> LENGTH: 19
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 600
rccaaaccca aacaaaaaca 19

<210> SEQ ID NO 601
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 601
attcccaata acatattcat ttacaaaa 28

<210> SEQ ID NO 602
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 602
cataaatcaa accrcaaaaa tctccaata 29

<210> SEQ ID NO 603
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 603
cctcctcccr cataaaaata tcaaaataa 29

<210> SEQ ID NO 604
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 604
actacaacta ctctacraca ctacc 25

<210> SEQ ID NO 605
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 605
ggaggggtyg ttttaggggg 20

<210> SEQ ID NO 606
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 606
actaaaaccc rcacctaacc ca 22

<210> SEQ ID NO 607
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 607
gtttgggtga taatagggaa aatta 25

<210> SEQ ID NO 608
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 608
ctaaccataa ctaacctacc cc 22

<210> SEQ ID NO 609
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 609
ccttcaaaac caaatacaaa cttat 25

<210> SEQ ID NO 610
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 610
aaagaagaag aagaagaaga agattag 27

<210> SEQ ID NO 611
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 611
ygttgattat ggttggtttg t 21

<210> SEQ ID NO 612
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 612
gatagggatt tyggggatag gg 22

<210> SEQ ID NO 613
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 613
ctacaaataa aacttctttc caaataaac 29

<210> SEQ ID NO 614
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 614
gagtygggta ggtttttggg tt 22

<210> SEQ ID NO 615
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 615
gaagatgtta gggtagygag ttttg 25

<210> SEQ ID NO 616
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 616
caaaacaata atttctcaac ttttcc 26

<210> SEQ ID NO 617
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 617

aatacaacat aaaaactctt tcrctaacac                                    30


<210> SEQ ID NO 618
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 618

actccctccc ttctattttc a                                             21


<210> SEQ ID NO 619
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 619

aatacaaaca aaacaatccc tccac                                         25


<210> SEQ ID NO 620
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 620

acttttacta taaaaattat aactacaaaa catc                               34


<210> SEQ ID NO 621
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 621

atcaaactat ccctaaccra aattcta                                       27


<210> SEQ ID NO 622
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 622
```

tgaagtaatg agatgaaaag tataagag 28

<210> SEQ ID NO 623
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 623
raaaacttaa accaatccaa c 21

<210> SEQ ID NO 624
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 624
tggttgtgga ggagttgag 19

<210> SEQ ID NO 625
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 625
ttttgtgtgg gagttggtt 19

<210> SEQ ID NO 626
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 626
acatatttac tacatttccr acctaaac 28

<210> SEQ ID NO 627
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 627
ggtttttagg agttttgttt ttagat 26

<210> SEQ ID NO 628
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 628
ggaggagatg ttgtttttag tg 22

<210> SEQ ID NO 629
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 629
gttgttaaat aaaaagtygg ggtgag 26

<210> SEQ ID NO 630
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 630
actttttatc tcttacaaac rtctcctaaa c 31

<210> SEQ ID NO 631
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 631
gggtagtagt gtgtgtaggg 20

<210> SEQ ID NO 632
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 632
acctacaacc ctaactacaa cta 23

<210> SEQ ID NO 633
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 633
caactcctcr aaatacccaa taca 24

<210> SEQ ID NO 634

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 634
caaccccaaa accaacaaat 20

<210> SEQ ID NO 635
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 635
tttttagygg gatagggtgt tgg 23

<210> SEQ ID NO 636
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 636
gttaggaggg attygggagg t 21

<210> SEQ ID NO 637
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 637
aaacccttcc caaccct 17

<210> SEQ ID NO 638
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 638
actccatcaa cracatccta aaca 24

<210> SEQ ID NO 639
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 639
yggtgttagg ttgtgggt 18

<210> SEQ ID NO 640
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 640
ggaggggtgg gatagga 17

<210> SEQ ID NO 641
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 641
tggttgtaat aggyggtggg t 21

<210> SEQ ID NO 642
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 642
tgggtatgyg ggtgttttag ga 22

<210> SEQ ID NO 643
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 643
catccrctaa ccaataaact tccttaaa 28

<210> SEQ ID NO 644
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 644
ctcccacccc taaacaaac 19

<210> SEQ ID NO 645
<211> LENGTH: 17
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 645
gtgggtgtgg gaggttt 17

<210> SEQ ID NO 646
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 646
rataccaaac tataaacaaa ccc 23

<210> SEQ ID NO 647
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 647
cccctatacc tctatctcta cc 22

<210> SEQ ID NO 648
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 648
gtgttgtggg ggttttgg 18

<210> SEQ ID NO 649
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 649
gggtgttaag ataagatatg tttagt 26

<210> SEQ ID NO 650
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 650
accaaaccct aaaacaacaa at 22

```
<210> SEQ ID NO 651
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 651

gggttaaata gaagaaatgt ttttaatg                                        28


<210> SEQ ID NO 652
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 652

rctaattcct aacaactaaa ccaac                                           25


<210> SEQ ID NO 653
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 653

gtttttgggg agggggaa                                                   18


<210> SEQ ID NO 654
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 654

acccctatcc ccaaatctac                                                 20


<210> SEQ ID NO 655
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 655

tccctcract ttaaccaact ca                                              22


<210> SEQ ID NO 656
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 656

gtggaggaga ggggaag                                                17


<210> SEQ ID NO 657
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 657

ygtggggttg agttttagtt                                             20
```

METHODS OF DIAGNOSING BLADDER CANCER

CROSS REFERENCE TO RELATED APPLICATIONS

This application is a national phase application under 35 U.S.C. § 371 that claims priority to International Application No. PCT/GB2016/051903 filed Jun. 24, 2016, which claims priority to Great Britain Patent Application No. 1511152.9 filed Jun. 24, 2015, all of which are incorporated herein reference in their entirety.

FIELD OF THE INVENTION

The present invention relates to methods of diagnosing bladder cancer in a patient, involving determining the methylation status of Methylation Variable Positions (MVPs) in DNA from the patient and providing a diagnosis based on methylation status data. The invention also relates to methods of treating bladder cancer comprising providing a diagnosis of bladder cancer by the diagnostic methods defined herein followed by administering one or more anti-cancer agents to a patient. The invention also relates to methylation-discriminatory arrays comprising probes directed to the MVPs defined herein and kits comprising the arrays.

BACKGROUND TO THE INVENTION

Bladder cancer represents one of the most common malignancies in the western world, ranking as the 5th most common cancer in the United States and causing approximately 3% of all cancer-related deaths [1, 2]. The foremost clinical sign at presentation is hematuria, and bladder cancer is detected in about 10% of all such cases investigated [3]. Bladder cancer is more likely in older male patients, current or past smokers and patients exposed to industrial carcinogens [4]. Younger females with nonvisible hematuria are less likely to harbor bladder cancer and for these patients delay in detection of bladder cancer, following misdiagnosis of haematuria, is a frequent event [5]. Cystoscopy is the current gold standard for detecting bladder cancer and is an invasive, uncomfortable procedure requiring clinic or hospital attendance and posing a small but significant risk of infection [6-9].

Each year in the UK, approximately 10,300 people are diagnosed with bladder cancer and 5,000 die from the disease. However, more than 100,000 cases per year are referred from primary care to urology haematuria clinics for cystoscopy and imaging. Bladder cancer is detected in only 10% of patients referred.

Of those with confirmed disease, two thirds are non-muscle invasive bladder cancer (NMIBC) and of these, 70% will recur and 15% will progress to muscle invasive bladder cancer (MIBC). Surveillance by cystoscopy is necessary to detect recurrence and is performed as frequently as 3 monthly for 2 years then 6 monthly and annually thereafter for cases at high risk of recurrence. The investigation of haematuria and the subsequent surveillance for recurrence poses a significant health economic cost estimated as £55.39 million, ranking bladder as one of the most expensive cancers to manage [10, 11]. There is therefore a great need for improved assays which can better identify patients harbouring disease and reduce the need for unnecessary cystoscopy.

No urinary-based biomarker has FDA approval as a standalone test for the detection of bladder cancer, and consequently guidelines recommend cystoscopy of all patients with visible haematuria and persistent nonvisible haematuria [10, 11]. Urine cytology is frequently used as a diagnostic aid in conjunction with cystoscopy but has low sensitivity to detect cancer other than high grade disease and carcinoma in situ, and cannot replace cystoscopy [12, 13]. Similarly commercially available assays based on single targets or small panels of targets fail to detect bladder cancer with sufficient sensitivity and are approved for use only in conjunction with cystoscopy [14].

Several studies have now shown the potential utility of DNA methylation biomarkers in body fluids, including urine [15-23], plasma/serum [24-26], and sputum [27, 28], for the non-invasive detection of cancer. Changes in DNA methylation play a key role in malignant transformation, leading to the silencing of tumor-suppressor genes and overexpression of oncogenes [29]. The ontogenic plasticity and relative stability of DNA methylation makes epigenetic changes ideal biomarkers for diagnosis.

Detection assays involving the presence of specific proteins in voided urine have been developed and commercialised. In these cases the number of proteins detected per assay is low and specificities and sensitivities remain unsatisfactory [14]. Detected protein biomarkers include human complement factor H-related protein, carcinoembryonic antigen (CEA), bladder tumor cell-associated mucins and nuclear mitotic apparatus protein 22 (NMP22).

In terms of assays assessing the expression of certain proteins, WO2014042763 describes a nine-biomarker panel consisting of IL-8, MMP9, SDC1, CCL18, SERPINE1, CD44, VEGF-A, CA9, and ANG for detection of protein in urine samples; a further nine-biomarker panel consisting of CA9, CCL18, MMP12, TMEM45A, MMP9, SEMA3D, ERBB2, CRH, and MXRA8; as well as a three-biomarker panel consisting of CCL18, CD44, and VEGF-A.

To date, DNA methylation biomarker assays for the detection of bladder cancer have been centered on the analysis of only a small number of loci, in part due to technological limitations and derivation of targets with cancer specificity [11-19]. In general, reported sensitivities and specificities are high relative to established assays, but would fail to attain performance characteristics achieved by cystoscopy. Methylation markers for bladder cancer previously studied include DAPK, BCL2, TERT, TWIST1, NID2, RARbeta, E-cadherin and p16. International patent application publication WO2013/144362 describes a diagnostic assay for bladder cancer involving detecting methylation of the promoter of the ECRG4 and/or the ITIH5 gene. US patent application publication US2013224738 describes a diagnostic assay for bladder cancer involving assessing the methylation status of genes consisting of BCL2, CDKN2A and NID2.

Improved assays for the accurate diagnosis of bladder cancer are sought and would be of significant clinical and economic benefit, particularly assays which are non-invasive.

SUMMARY OF THE INVENTION

Diagnostic methods are provided which can detect bladder cancer from a biological sample, particularly a voided urine sample, with robust and high sensitivity and specificity, and which have the potential to reduce the need for cystoscopy in patients referred with haematuria and in patients undergoing surveillance for disease recurrence. Avoiding cystoscopy will reduce the cost of bladder cancer management and positively impact on patient wellbeing, reducing both the number of hospital visits and the inconvenience of an invasive investigation. Thus the invention provides the following:

The invention provides a method of diagnosing bladder cancer in an individual comprising:

(a) providing DNA from a sample from the individual;

(b) determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (c) diagnosing bladder cancer in the individual when at least 25 of the MVPs of the group of (b) are methylated.

In any such method the group of MVPs may comprises at least 40 of the MVPs identified in SEQ ID NOS 1 to 150 and denoted by [CG], and wherein bladder cancer is diagnosed when at least 25 of the MVPs identified in SEQ ID NOS 1 to 150 and denoted by [CG] are methylated.

The group of MVPs may comprise at least 50 of the MVPs identified in SEQ ID NOS 1 to 150 and denoted by [CG], or may comprise at least 100 of the MVPs identified in SEQ ID NOS 1 to 150 and denoted by [CG].

The group of MVPs may comprise all 150 of the MVPs identified in SEQ ID NOS 1 to 150 and denoted by [CG].

In methods described above, cancer may be diagnosed in the individual when at least 40 of the MVPs selected from the MVPs identified in SEQ ID NOS 1 to 150 and denoted by [CG] are methylated, or when at least 50 of the MVPs selected from the MVPs identified in SEQ ID NOS 1 to 150 and denoted by [CG] are methylated, or when at least 100 of the MVPs are methylated, or when all 150 MVPs are methylated.

In methods described above, the MVPs determined to be methylated may include the MVPs identified in SEQ ID NOS 1 to 3 and denoted by [CG], or may include the MVPs identified in SEQ ID NOS 1 to 5 and denoted by [CG], or may include the MVPs identified in SEQ ID NOS 1 to 10 and denoted by [CG], or may include the MVPs identified in SEQ ID NOS 1 to 40 and denoted by [CG].

In methods described above, the group of MVPs may comprise all 150 of the MVPs identified in SEQ ID NOS 1 to 150 and denoted by [CG], wherein bladder cancer is diagnosed in the individual when at least 40 of the MVPs selected from the MVPs identified in SEQ ID NOS 1 to 150 and denoted by [CG] are methylated, and wherein the MVPs determined to be methylated include the MVPs identified in SEQ ID NOS 1 to 10 and denoted by [CG].

In any of the methods described above, the step of determining whether each one the MVPs is methylated may comprise bisulphite converting the DNA.

In any of the methods described above, the step of determining whether each one the MVPs is methylated may comprise:

1) performing a sequencing step to determine the sequence of MVPs;

2) hybridising DNA to an array comprising probes capable of discriminating between methylated and non-methylated forms of MVPs and applying a detection system to the array to discriminate methylated and non-methylated forms of the MVPs; or 3) performing an amplification step using methylation-specific primers, wherein the status of an MVP as methylated or non-methylated is determined by the presence or absence of an amplified product.

Before the sequencing or hybridization steps, an amplification step may be performed, wherein loci comprising each MVP are amplified. Amplification may be performed by PCR.

A capturing step may be performed before the sequencing or hybridization steps. The capturing step may involve binding polynucleotides comprising the MVP loci to binding molecules specific to the MVP loci and collecting complexes comprising MVP loci and binding molecules; and wherein:

i. the capturing step occurs before the step of bisulphite converting the DNA;

ii. the capturing step occurs after the step of bisulphite converting the DNA but before the amplification or hybridization steps; or iii. the capturing step occurs after the step of bisulphite converting the DNA and after the amplification step.

The binding molecules may be oligonucleotides specific for each MVP, preferably DNA or RNA molecules each comprising a sequence which is complementary to the corresponding MVP.

The binding molecule may be coupled to a purification moiety.

The purification moiety may comprise a first purification moiety and the step of collecting complexes comprising MVP loci and binding molecules may comprise binding the first purification moiety to substrates comprising a second purification moiety, wherein first and second purification moieties form an interaction complex.

The first purification moiety may be biotin and the second purification moiety may be streptavidin; or the first purification moiety may be streptavidin and the second purification moiety may be biotin.

The step of amplifying loci comprising MVPs may comprise the use of primers which are independent of the methylation status of the MVP.

The step of amplifying loci comprising MVPs may be performed by microdroplet PCR amplification.

In any of the methods described above, the biological sample obtained from the individual may be a sample of urine, blood, serum, plasma or cell-free DNA.

In any of the methods described above, the method may achieve a ROC sensitivity of 95% or greater and a ROC specificity of 90% or greater; preferably a ROC sensitivity of 96% and a ROC specificity of 97%, preferably a ROC AUC of 95% or greater, preferably 98%.

In any of the methods described above, the method may achieve a negative predictive value (NPV) of 95% or greater, preferably 97%.

In any of the methods described above, the step of diagnosing bladder cancer in the individual may further comprise:

I. stratifying the grade of the tumor; and/or

II. determining the risk of recurrence of the tumor; and/or

III. determining the risk of progression of non-muscular invasive disease; and/or determining the likely response to treatment therapy.

The invention additionally provides a method of treating bladder cancer in an individual comprising:

(a) obtaining DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention additionally provides a method of treating bladder cancer in an individual comprising:

(a) providing DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention additionally provides a method of treating bladder cancer in an individual comprising:

(a) determining whether each one of a group of MVPs selected from a panel comprising the MVPs identified in SEQ ID NOS 1 to 150 and denoted by [CG] is methylated in DNA from a sample from the individual, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention additionally provides a method of treating bladder cancer in an individual comprising administering one or more bladder cancer treatments to the individual, wherein the individual has been diagnosed with bladder cancer by steps comprising:

(a) providing DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (b) diagnosing bladder cancer in the individual when at least 25 MVPs of the group of (a) are methylated.

The invention additionally provides a method of diagnosing bladder cancer in an individual comprising:

(a) obtaining data which identify whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (b) diagnosing bladder cancer in the individual when at least 25 MVPs of the group of (a) are methylated;

wherein the data were obtained by a method comprising:

i. obtaining DNA from the sample; and ii. determining whether MVPs are methylated in the DNA.

In any of the methods described above the cancer may be a non-muscle invasive bladder cancer (NMIBC). The cancer may be a muscle invasive bladder cancer (MIBC).

The invention additionally provides an array capable of discriminating between methylated and non-methylated forms of MVPs; the array comprising oligonucleotide probes specific for a methylated form of each MVP in a MVP panel and oligonucleotide probes specific for a non-methylated form of each MVP in the panel; wherein the panel consists of at least 25 MVPs selected from the MVPs identified in SEQ ID NOS 1 to 150.

In certain embodiments the array is not an Infinium HumanMethylation450 BeadChip array. In certain embodiments the number of MVP-specific oligonucleotide probes of the array is less than 482,421, preferably 482,000 or less, 480,000 or less, 450,000 or less, 440,000 or less, 430,000 or less, 420,000 or less, 410,000 or less, or 400,000 or less.

In an array as described above, the panel may consist of at least 40 MVPs selected from the MVPs identified in SEQ ID NOS 1 to 150; preferably at least 50 MVPs, at least 60 MVPs, at least 70 MVPs, at least 80 MVPs, at least 90 MVPs, at least 100 MVPs, at least 110 MVPs, at least 120 MVPs, at least 130 MVPs, at least 140 MVPs, at least 145 MVPs, or all 150 MVPs identified in SEQ ID NOS 1 to 150.

In an array as described above, the panel may include the MVPs defined by SEQ ID NOS 1 to 3, or the MVPs defined by SEQ ID NOS 1 to 5, or the MVPs defined by SEQ ID NOS 1 to 10, or the MVPs defined by SEQ ID NOS 1 to 20, or the MVPs defined by SEQ ID NOS 1 to 30, or the MVPs defined by SEQ ID NOS 1 to 40, or the MVPs defined by SEQ ID NOS 1 to 50, or the MVPs defined by SEQ ID NOS 1 to 60, or the MVPs defined by SEQ ID NOS 1 to 70, or the MVPs defined by SEQ ID NOS 1 to 80, or the MVPs defined by SEQ ID NOS 1 to 90, or the MVPs defined by SEQ ID NOS 1 to 100, or the MVPs defined by SEQ ID NOS 1 to 100, or the MVPs defined by SEQ ID NOS 1 to 120, or the MVPs defined by SEQ ID NOS 1 to 130, or the MVPs defined by SEQ ID NOS 1 to 140, or the MVPs defined by SEQ ID NOS 1 to 150.

The panel may include all MVPs defined by SEQ ID NOS 1 to 150.

In array as described above, the array may further comprise one or more oligonucleotides comprising a MVP selected from any of the MVPs defined in SEQ ID NOS 1 to 150, wherein the one or more oligonucleotides are hybridized to corresponding oligonucleotide probes of the array.

The one or more oligonucleotides may comprise at least 20 MVPs selected from the MVPs identified in SEQ ID NOS 1 to 150; preferably at least 50 MVPs, at least 60 MVPs, at least 70 MVPs, at least 80 MVPs, at least 90 MVPs, at least 100 MVPs, at least 110 MVPs, at least 120 MVPs, at least 130 MVPs, at least 140 MVPs, at least 145 MVPs, or all 150 MVPs identified in SEQ ID NOS 1 to 150.

The one or more oligonucleotides may comprise the MVPs defined by SEQ ID NOS 1 to 10, or the MVPs defined by SEQ ID NOS 1 to 20, or the MVPs defined by SEQ ID NOS 1 to 30, or the MVPs defined by SEQ ID NOS 1 to 40, or the MVPs defined by SEQ ID NOS 1 to 50, or the MVPs defined by SEQ ID NOS 1 to 60, or the MVPs defined by SEQ ID NOS 1 to 70, or the MVPs defined by SEQ ID NOS 1 to 80, or the MVPs defined by SEQ ID NOS 1 to 90, or the MVPs defined by SEQ ID NOS 1 to 100, or the MVPs defined by SEQ ID NOS 1 to 110, or the MVPs defined by SEQ ID NOS 1 to 120, or the MVPs defined by SEQ ID NOS 1 to 130, or the MVPs defined by SEQ ID NOS 1 to 140, or the MVPs defined by SEQ ID NOS 1 to 150.

The one or more oligonucleotides may comprise all MVPs defined by SEQ ID NOS 1 to 150.

Arrays as described above may be obtainable by hybridizing to an array as described above a group of oligonucleotides each comprising a different MVP selected from any of the MVPs defined in SEQ ID NOS 1 to 150, and wherein the group comprises at least 40 oligonucleotides.

In such a hybridized array, the group may comprise at least 50 oligonucleotides. The group may comprise at least 60, at least 70, at least 80, at least 90, at least 100, at least 110, at least 120, at least 130, at least 140, at least 145, or at least 150 oligonucleotides.

In a hybridized array, the group may comprise at least 40 oligonucleotides comprising the MVPs defined by SEQ ID NOS 1 to 20, or wherein the group may comprise at least 50 oligonucleotides comprising the MVPs defined by SEQ ID NOS 1 to 50, or wherein the group may comprise at least 60 oligonucleotides comprising the MVPs defined by SEQ ID NOS 1 to 60, or wherein the group may comprise at least 70 oligonucleotides comprising the MVPs defined by SEQ ID NOS 1 to 70, or wherein the group may comprise at least 80 oligonucleotides comprising the MVPs defined by SEQ ID NOS 1 to 80, or wherein the group may comprise at least 90 oligonucleotides comprising the MVPs defined by SEQ ID NOS 1 to 90, or wherein the group may comprise at least 100 oligonucleotides comprising the MVPs defined by SEQ ID NOS 1 to 100, or wherein the group may comprise at least 110 oligonucleotides comprising the MVPs defined by SEQ ID NOS 1 to 110, or wherein the group may comprise at least 120 oligonucleotides comprising the MVPs defined by SEQ ID NOS 1 to 120, or wherein the group may comprise at least 130 oligonucleotides comprising the MVPs defined by SEQ ID NOS 1 to 130, or wherein the group may comprise at least 140 oligonucleotides comprising the MVPs defined by SEQ ID NOS 1 to 140, or wherein the group may comprise at least 145 oligonucleotides comprising the MVPs defined by SEQ ID NOS 1 to 145, or wherein the group may comprise at least 150 oligonucleotides comprising the MVPs defined by SEQ ID NOS 1 to 150. The group may comprise at least the 150 oligonucleotides comprising the MVPs defined by SEQ ID NOS 1 to 150.

The invention also provides a process for making the hybridized array as defined above, comprising contacting an array as defined above with a group of oligonucleotides each comprising a different MVP selected from any of the MVPs defined in SEQ ID NOS 1 to 150, and wherein the group comprises at least 25 oligonucleotides.

The invention also provides a process for making a hybridized array as defined above, comprising contacting an array as defined above with a group of oligonucleotides as defined above.

The invention also provides a kit comprising any of the arrays described above.

The kit may further comprise a DNA modifying regent that is capable of modifying a non-methylated cytosine in a MVP dinucleotide but is not capable of modifying a methylated cytosine in a MVP dinucleotide, optionally wherein the dinucleotide is CpG. The DNA modifying regent may be a bisulphite reagent.

DETAILED DESCRIPTION OF THE INVENTION

Bladder Cancer

Figure 1:
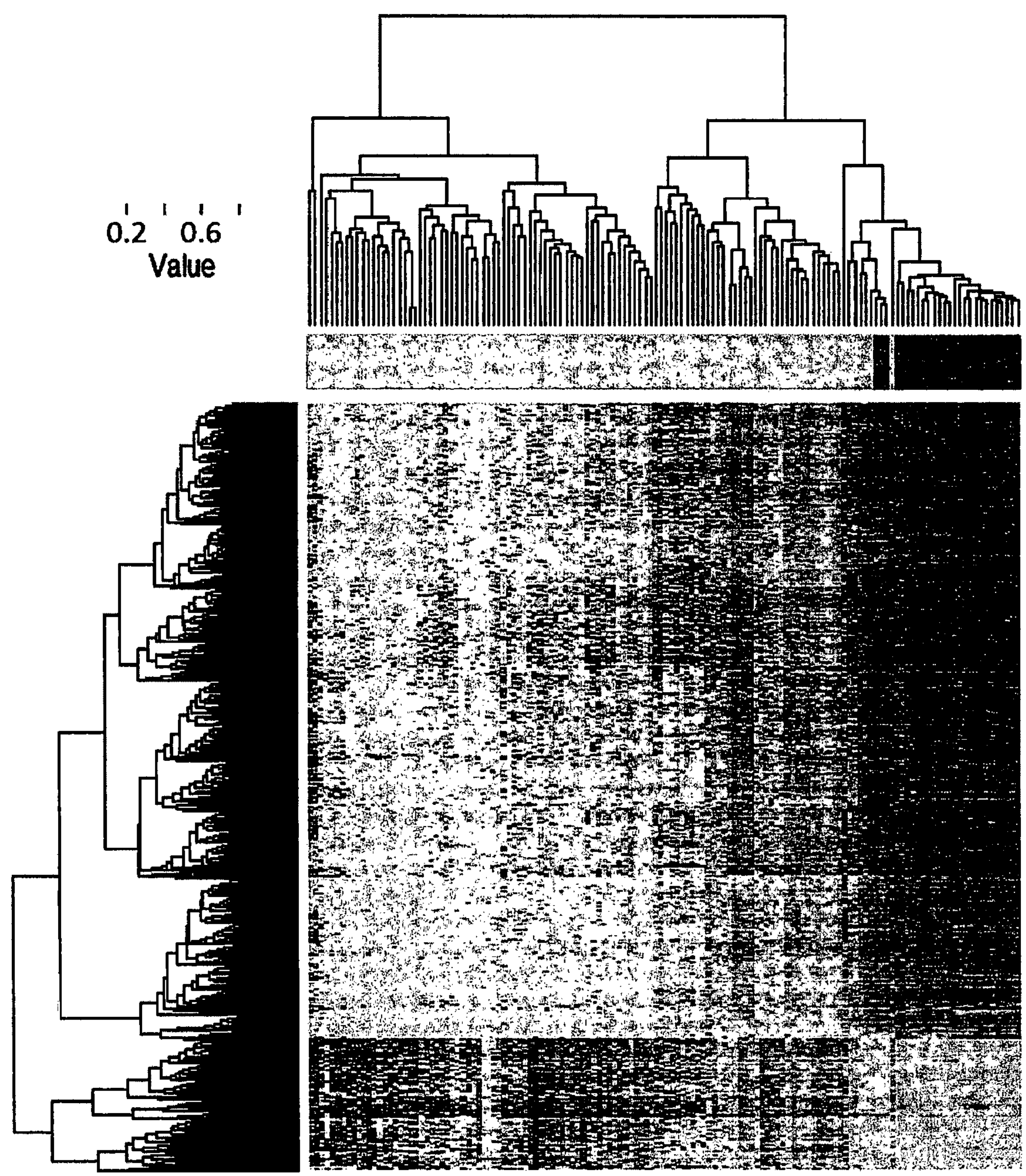
FIG. 1. Heatmap of 9786 MVPs (1746 hypermethylated MVPs, 8040 hypomethylated MVPs) between bladder cancer (red) and 30 normal urothelium (blue).

As discussed above, bladder cancers represent one of the most prevalent groups of cancers in the western world. Transitional cell carcinoma is the most common type, and accounts for approximately 90% of bladder cancers. Transitional cell carcinomas arise from the transitional epithelium, which is a tissue lining the inner surface of the bladder. The remaining 10% of bladder cancers are mainly comprised of squamous cell carcinoma, adenocarcinoma, sarcoma, and small cell carcinoma. Squamous cell carcinoma also arises from epithelial tissue, from squamous cells. These are thin, flat cells found in the most superficial epithelial layer. Adenocarcinomas form from epithelial cells having glandular characteristics and/or origin. Sarcomas derive from cells of mesenchymal origin, such as the cells of the fat and muscle layers of the bladder. Small cell carcinomas have a rapid doubling time and are capable of earlier metastases, making them particularly aggressive.

Bladder cancers may also be classified as non-muscle invasive bladder cancer (NMIBC) and muscle invasive bladder cancer (MIBC).

The diagnostic and treatment methods described herein are capable of positively identifying malignant cells of all classifications of bladder cancer. Thus, any of the methods described herein may be used to diagnose transitional cell carcinoma of the bladder, squamous cell carcinoma of the bladder, adenocarcinoma of the bladder, sarcoma of the bladder, small cell carcinoma of the bladder, metastatic bladder cancer, leiomyosarcoma (a tumor arising from smooth muscle), lymphoma (a tumor that usually arises in the lymph nodes), malignant melanoma (a tumor that usually arises from the skin) and large cell neuroendocrine carcinoma. Primary forms and recurrent forms of bladder cancer are included. The cancer to be diagnosed or treated as described herein may be a urothelial cell cancer. Thus, the cancer may be cancer of the ureter, urethra or renal pelvis.

The most preferred patient type to which the diagnostic assays described herein are applicable are humans. The diagnostic assays described herein may also be used to identify bladder cancer in a non-human animal. For example, non-human animals may contain tissue derived from humans, e.g. xenografts. Thus, diagnostic assays may be used to diagnose human bladder cancer in an animal model of human bladder cancer. Typical non-human animals to which the diagnostic assays described herein are applicable are rodents such as rats or mice.

Methylation Variable Positions (MVPs)

Methylation of DNA is a recognised form of epigenetic modification which has the capability of altering the expression of genes and other elements such as microRNAs [51]. In cancer development and progression, methylation may have the effect of e.g. silencing tumor suppressor genes and/or increasing the expression of oncogenes. Other forms of dysregulation may occur as a result of methylation. Methylation of DNA occurs at discrete loci which are predominately dinucleotide consisting of a CpG motif, but may also occur at CHH motifs (where H is A, C, or T). During methylation, a methyl group is added to the fifth carbon of cytosine bases to create methylcytosine.

Methylation can occur throughout the genome and is not limited to regions with respect to an expressed sequence such as a gene. Methylation typically, but not always, occurs in a promoter or other regulatory region of an expressed sequence.

A Methylation Variable Position (MVP) as defined herein is any dinucleotide locus which may show a variation in its methylation status between phenotypes, i.e. between tumour and normal tissue. An MVP is preferably a CpG or a CHH dinucleotide motif. An MPV as defined herein is not limited to the position of the locus with respect to a corresponding expressed sequence.

Typically, an assessment of DNA methylation status involves analysing the presence or absence of methyl groups in DNA, for example methyl groups on the $5^{th}$ position of one or more cytosine nucleotides. Preferably, the methylation status of one or more cytosine nucleotides present as a CpG dinucleotide (where C stands for Cytosine, G for Guanine and p for the phosphate group linking the two) is assessed.

By assessing the methylation status of an MVP or determining whether an MVP is methylated it is meant that a determination is made as to whether an MVP was methylated or unmethylated in the starting sample of DNA obtained from the individual prior to subsequent processing.

An MVP is herein defined as methylated if one or more alleles of that MVP in a sample of genomic DNA from the patient is determined to possess one or more methylated CpG dinucleotide loci.

In any of the methods described herein, the MVPs determined to be methylated are methylated relative to normal urothelium control and/or whole blood control.

Specific MVPs useful for diagnostic purposes are set forth in Table 1 and are identified by SEQ ID number, as well as Illumina ID number (Ilmn ID). Exemplary primers for amplifying the defined MVPs are set forth in Table 2 and are also identified by SEQ ID number.

Identification and Assessment of Methylation Variable Position (MVP) Status

A variety of techniques are available for the identification and assessment of Methylation Variable Positions (MVPs), as will be outlined briefly below. The diagnostic methods described herein encompass any suitable technique for the determination of MVP status.

Methyl groups are lost from a starting DNA molecule during conventional in vitro handling steps such as PCR. To avoid this, techniques for the detection of methyl groups commonly involve the preliminary treatment of DNA prior to subsequent processing, in a way that preserves the methylation status information of the original DNA molecule. Such preliminary techniques involve three main categories of processing, i.e. bisulphite modification, restriction enzyme digestion and affinity-based analysis. Products of these techniques can then be coupled with sequencing or array-based platforms for subsequent identification or qualitative assessment of MVP methylation status.

Techniques involving bisulphite modification of DNA have become the most common methods for detection and assessment of methylation status of CpG dinucleotide. Treatment of DNA with bisulphite, e.g. sodium bisulphite, converts cytosine bases to uracil bases, but has no effect on 5-methylcytosines. Thus, the presence of a cytosine in bisulphite-treated DNA is indicative of the presence of a cytosine base which was previously methylated in the starting DNA molecule. Such cytosine bases can be detected by a variety of techniques. For example, primers specific for unmethylated versus methylated DNA can be generated and used for PCR-based identification of methylated CpG dinucleotides. A separation/capture step may be performed, e.g. using binding molecules such as complementary oligonucleotide sequences. Standard and next-generation DNA sequencing protocols can also be used.

In other approaches, methylation-sensitive enzymes can be employed which digest or cut only in the presence of methylated DNA. Analysis of resulting fragments is commonly carried out using microarrays.

Affinity-based techniques exploit binding interactions to capture fragments of methylated DNA for the purposes of enrichment. Binding molecules such as anti-5-methylcytosine antibodies are commonly employed prior to subsequent processing steps such as PCR and sequencing.

Olkhov-Mitsel and Bapat (2012) [51] provide a comprehensive review of techniques available for the identification and assessment of MVP-based biomarkers involving methylcytosine.

For the purposes of assessing the methylation status of the MVP-based biomarkers characterised and described herein, any suitable method can be employed.

Preferred methods involve bisulphite treatment of DNA, including amplification of the identified MVP loci for methylation specific PCR and/or sequencing and/or assessment of the methylation status of target loci using methylation-discriminatory microarrays.

Amplification of MVP loci can be achieved by a variety of approaches. Preferably, MVP loci are amplified using PCR. MVP may also be amplified by other techniques such as multiplex ligation-dependent probe amplification (MLPA). A variety of PCR-based approaches may be used. For example, methylation-specific primers may be hybridized to DNA containing the MVP sequence of interest. Such primers may be designed to anneal to a sequence derived from either a methylated or non-methylated MVP locus. Following annealing, a PCR reaction is performed and the presence of a subsequent PCR product indicates the presence of an annealed MVP of identifiable sequence. In such methods, DNA is bisulphite converted prior to amplification. Such techniques are commonly referred to as methylation specific PCR (MSP) [53].

In other techniques, PCR primers may anneal to the MVP sequence of interest independently of the methylation status, and further processing steps may be used to determine the status of the MVP. Assays are designed so that the MVP site(s) are located between primer annealing sites. This method scheme is used in techniques such as bisulphite genomic sequencing [54], COBRA [55], Ms-SNuPE [56]. In such methods, DNA can be bisulphite converted before or after amplification.

Preferably, small-scale PCR approaches are used. Such approaches commonly involve mass partitioning of samples (e.g. digital PCR). These techniques offer robust accuracy and sensitivity in the context of a highly miniaturised system (pico-liter sized droplets), ideal for the subsequent handling of small quantities of DNA obtainable from the potentially small volume of cellular material present in biological samples, particularly urine samples. A variety of such small-scale PCR techniques are widely available. For example, microdroplet-based PCR instruments are available from a variety of suppliers, including RainDance Technologies, Inc. (Billerica, Mass.; see the RainDance Technologies, Inc. website on the world wide web) and Bio-Rad, Inc. (see the Bio-Rad Inc. website on the world wide web). Microarray platforms may also be used to carry out small-scale PCR. Such platforms may include microfluidic network-based arrays e.g. available from Fluidigm Corp. (see the Fluidigm Corp. website on the world wide web).

Following amplification of MVP loci, amplified PCR products may be coupled to subsequent analytical platforms in order to determine the methylation status of the MVPs of interest. For example, the PCR products may be directly sequenced to determine the presence or absence of a methylcytosine at the target MVP or analysed by array-based techniques.

Any suitable sequencing techniques may be employed to determine the sequence of target DNA. In the methods of the present invention the use of high-throughput, so-called "second generation", "third generation" and "next generation" techniques to sequence bisulphite-treated DNA are preferred.

In second generation techniques, large numbers of DNA molecules are sequenced in parallel. Typically, tens of thousands of molecules are anchored to a given location at high density and sequences are determined in a process dependent upon DNA synthesis. Reactions generally consist of successive reagent delivery and washing steps, e.g. to allow the incorporation of reversible labelled terminator bases, and scanning steps to determine the order of base incorporation. Array-based systems of this type are available commercially e.g. from Illumina, Inc. (San Diego, Calif.; see the Illumina, Inc. website on the world wide web).

Third generation techniques are typically defined by the absence of a requirement to halt the sequencing process between detection steps and can therefore be viewed as real-time systems. For example, the base-specific release of hydrogen ions, which occurs during the incorporation process, can be detected in the context of microwell systems (e.g. see the Ion Torrent system available from Life Technologies; see the Life Technologies website on the world wide web). Similarly, in pyrosequencing the base-specific release of pyrophosphate (PPi) is detected and analysed. In nanopore technologies, DNA molecules are passed through or positioned next to nanopores, and the identities of individual bases are determined following movement of the DNA molecule relative to the nanopore. Systems of this type are available commercially e.g. from Oxford Nanopore (see the Oxford Nanopore website on the world wide web). In an alternative method, a DNA polymerase enzyme is confined in a "zero-mode waveguide" and the identity of incorporated bases are determined with florescence detection of gamma-labeled phosphonucleotides (see e.g. Pacific Biosciences; see the Pacific Biosciences website on the world wide web).

In other methods in accordance with the invention sequencing steps may be omitted. For example, amplified PCR products may be applied directly to hybridization arrays based on the principle of the annealing of two complementary nucleic acid strands to form a double-stranded molecule. Hybridization arrays may be designed to include probes which are able to hybridize to amplification products of an MVP and allow discrimination between methylated and non-methylated loci. For example, probes may be designed which are able to selectively hybridize to an MVP locus containing thymine, indicating the generation of uracil following bisulphite conversion of an unmethylated cytosine in the starting template DNA. Conversely, probes may be designed which are able to selectively hybridize to an MVP locus containing cytosine, indicating the absence of uracil conversion following bisulphite treatment. This corresponds with a methylated MVP locus in the starting template DNA.

Following the application of a suitable detection system to the array, computer-based analytical techniques can be used to determine the methylation status of an MVP. Detection systems may include, e.g. the addition of fluorescent molecules following a methylation status-specific probe extension reaction. Such techniques allow MVP status determination without the specific need for the sequencing of MVP amplification products. Such array-based discriminatory probes may be termed methylation-specific probes.

Any suitable methylation-discriminatory microarrays may be employed to assess the methylation status of the MVPs described herein. A preferred methylation-discriminatory microarray system is provided by Illumina, Inc. (San Diego, Calif.; see the Illumina, Inc. website on the world wide web). In particular, the Infinium HumanMethylation450 BeadChip array system may be used to assess the methylation status of diagnostic MVPs for bladder cancer as described herein. Such a system exploits the chemical modifications made to DNA following bisulphite treatment of the starting DNA molecule. Briefly, the array comprises beads to which are coupled oligonucleotide probes specific for DNA sequences corresponding to the unmethylated form of an MVP, as well as separate beads to which are coupled oligonucleotide probes specific for DNA sequences corresponding to the methylated form of an MVP. Candidate DNA molecules are applied to the array and selectively hybridize, under appropriate conditions, to the oligonucleotide probe corresponding to the relevant epigenetic form. Thus, a DNA molecule derived from an MVP which was methylated in the corresponding genomic DNA will selectively attach to the bead comprising the methylation-specific oligonucleotide probe, but will fail to attach to the bead comprising the non-methylation-specific oligonucleotide probe. Single-base extension of only the hybridized probes incorporates a labeled ddNTP, which is subsequently stained with a fluorescence reagent and imaged. The methylation status of the MVP may be determined by calculating the ratio of the fluorescent signal derived from the methylated and unmethylated sites.

Because the bladder cancer-specific diagnostic MVP biomarkers defined herein were initially identified using the Illumina Infinium HumanMethylation450 BeadChip array system, the same chip system can be used to interrogate those same MVPs in the diagnostic assays described herein. Alternative or customised arrays could, however, be employed to interrogate the bladder cancer-specific diagnostic MVP biomarkers defined herein, provided that they comprise means for interrogating all MVPs for a given method, as defined herein.

Techniques involving combinations of the above-described methods may also be used. For example, DNA containing MVP sequences of interest may be hybridized to microarrays and then subjected to DNA sequencing to determine the status of the MVP as described above.

In the methods described above, sequences corresponding to MVP loci may also be subjected to an enrichment process. DNA containing MVP sequences of interest may be captured by binding molecules such as oligonucleotide probes complementary to the MVP target sequence of interest. Sequences corresponding to MVP loci may be captured before or after bisulphite conversion or before or after amplification. Probes may be designed to be complementary to bisulphite converted DNA. Captured DNA may then be subjected to further processing steps to determine the status of the MVP, such as DNA sequencing steps.

Capture/separation steps may be custom designed. Alternatively a variety of such techniques are available commercially, e.g. the SureSelect target enrichment system available from Agilent Technologies (see the Agilent Technologies website on the world wide web). In this system biotinylated "bait" or "probe" sequences (e.g. RNA) complementary to the DNA containing MVP sequences of interest are hybridized to sample nucleic acids. Streptavidin-coated magnetic beads are then used to capture sequences of interest hybridized to bait sequences. Unbound fractions are discarded. Bait sequences are then removed (e.g. by digestion of RNA) thus providing an enriched pool of MVP target sequences separated from non-MVP sequences. In a preferred method of the invention, template DNA is subjected to bisulphite conversion and target loci are then amplified by small-scale PCR such as microdroplet PCR using primers which are independent of the methylation status of the MVP. Following amplification, samples are subjected to a capture step to enrich for PCR products containing the target MVP, e.g. captured and purified using magnetic beads, as described above. Following capture, a standard PCR reaction is carried out to incorporate DNA sequencing barcodes into MVP-containing amplicons. PCR products are again purified and then subjected to DNA sequencing and analysis to determine the presence or absence of a methylcytosine at the target genomic MVP [31].

The MVP biomarker loci defined herein are identified e.g. by Illumina® identifiers (IlmnID) These MVP loci identifiers refer to individual MVP sites used in the commercially available Illumina® Infinium Human Methylation450 BeadChip kit. The identity of each MVP site represented by each MVP loci identifier is publicly available from the Illumina, Inc. website under reference to the MVP sites used in the Infinium Human Methylation450 BeadChip kit.

Further information regarding MVP loci identification used in Illumina, Inc products is found in the technical note entitled "Technical Note: Epigenetics. CpG Loci Identification. A guide to Illumina's method for unambiguous CpG loci identification and tracking for the Golden Gate® and Infinium® Assay for Methylation" published in 2010 and found at the Illumina, Inc. website on the world wide web.

Further information regarding the Illumina® Infinium Human Methylation450 BeadChip system can be found at:

the Illumina, Inc. website on the world wide web;

To complement evolving public databases to provide accurate MVP/CpG loci identifiers and strand orientation, Illumina® has developed a method to consistently designate MVP/CpG loci based on the actual or contextual sequence of each individual MVP/CpG locus. To unambiguously refer to MVP/CpG loci in any species, Illumina® has developed a consistent and deterministic MVP loci database to ensure uniformity in the reporting of methylation data. The Illumina® method takes advantage of sequences flanking a MVP locus to generate a unique MVP locus cluster ID. This number is based on sequence information only and is unaffected by genome version. Illumina's standardized nomenclature also parallels the TOP/BOT strand nomenclature (which indicates the strand orientation) commonly used for single nucleotide polymorphism (SNP) designation.

Illumina® Identifiers for the Infinium Human Methylation450 BeadChip system are also available from public repositories such as Gene Expression Omnibus (GEO) (see the GEO webpage on the National Center for Biotechnology Information website on the world wide web).

An MVP as defined herein thus refers to the CG dinucleotide motif identified in relation to each SEQ ID NO. and Illumina Identifier (Ilmn ID) as listed in Table 1, wherein the cytosine base of the dinucleotide (noted in bold and square brackets in the sequences listed at Table 1) may (or may not) be modified. Thus by determining the methylation status of a CpG defined by or identified in a given SEQ ID NO., or determining whether such a CpG is methylated, it is meant that a determination is made as to whether the cytosine of the CG dinucleotide motif identified in bold and in square brackets in a sequence shown in Table 1 is methylated or not at one or more loci in the sample of DNA from the individual, accepting that variation in the sequence upstream and downstream of any given CpG may exist due to sequencing errors or variation between individuals.

The invention provides a method of diagnosing bladder cancer in an individual comprising:

(a) providing DNA from a sample from the individual;

(b) determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (c) diagnosing bladder cancer in the individual when at least 25 of the MVPs of the group of (b) are methylated.

In any such method described herein, the group of MVPs (i.e. those MVPs the methylation status of which are to be determined) may comprise 26 or more of the MVPs identified in SEQ ID NOS 1 to 150 and denoted by [CG]; or the group may comprise 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, 61 or more, 62 or more, 63 or more, 64 or more, 65 or more, 66 or more, 67 or more, 68 or more, 69 or more, 70 or more, 71 or more, 72 or more, 73 or more, 74 or more, 75 or more, 76 or more, 77 or more, 78 or more, 79 or more, 80 or more, 81 or more, 82 or more, 83 or more, 84 or more, 85 or more, 86 or more, 87 or more, 88 or more, 89 or more, 90 or more, 91 or more, 92 or more, 93 or more, 94 or more, 95 or more, 96 or more, 97 or more, 98 or more, 99 or more, 100 or more, 101 or more, 102 or more, 103 or more, 104 or more, 105 or more, 106 or more, 107 or more, 108 or more, 109 or more, 110 or more, 111 or more, 112 or more, 113 or more, 114 or more, 115 or more, 116 or more, 117 or more, 118 or more, 119 or more, 120 or more, 121 or more, 122 or more, 123 or more, 124 or more, 125 or more, 126 or more, 127 or more, 128 or more, 129 or more, 130 or more, 131 or more, 132 or more, 133 or more, 134 or more, 135 or more, 136 or more, 137 or more, 138 or more, 139 or more, 140 or more, 141 or more, 142 or more, 143 or more, 144 or more, 145 or more, 146 or more, 147 or more or 148 or more of the MVPs identified in SEQ ID NOS 1 to 150 and denoted by [CG]. The group may comprise 149 or 150 of the MVPs identified in SEQ ID NOS 1 to 150 and denoted by [CG].

In any of the methods described above, bladder cancer may be diagnosed when at least 25 of the MVPs identified in SEQ ID NOS 1 to 150 and denoted by [CG] are methylated. Bladder cancer may be diagnosed when 26 or more of the MVPs identified in SEQ ID NOS 1 to 150 and denoted by [CG] are methylated; or when 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, 61 or more, 62 or more, 63 or more, 64 or more, 65 or more, 66 or more, 67 or more, 68 or more, 69 or more, 70 or more, 71 or more, 72 or more, 73 or more, 74 or more, 75 or more, 76 or more, 77 or more, 78 or more, 79 or more, 80 or more, 81 or more, 82 or more, 83 or more, 84 or more, 85 or more, 86 or more, 87 or more, 88 or more, 89 or more, 90 or more, 91 or more, 92 or more, 93 or more, 94 or more, 95 or more, 96 or more, 97 or more, 98 or more, 99 or more, 100 or more, 101 or more, 102 or more, 103 or more, 104 or more, 105 or more, 106 or more, 107 or more, 108 or more, 109 or more, 110 or more, 111 or more, 112 or more, 113 or more, 114 or more, 115 or more, 116 or more, 117 or more, 118 or more, 119 or more, 120 or more, 121 or more, 122 or more, 123 or more, 124 or more, 125 or more, 126 or more, 127 or more, 128 or more, 129 or more, 130 or more, 131 or more, 132 or more, 133 or more, 134 or more, 135 or more, 136 or more, 137 or more, 138 or more, 139 or more, 140 or more, 141 or more, 142 or more, 143 or more, 144 or more, 145 or more, 146 or more, 147 or more, or 148 or more of the MVPs identified in SEQ ID NOS 1 to 150 and denoted by [CG] are methylated. Bladder cancer may be diagnosed when 149 or 150 of the MVPs identified in SEQ ID NOS 1 to 150 and denoted by [CG] are methylated.

Preferably, bladder cancer may be diagnosed when 40 or more of the MVPs identified in SEQ ID NOS 1 to 150 and denoted by [CG] are methylated.

Bladder cancer may also be diagnosed when 50 or more, 60 or more, 70 or more or 80 or more, 90 or more or 100 or more of the MVPs identified in SEQ ID NOS 1 to 150 and denoted by [CG] are methylated.

In any of the methods described above the MVPs determined to be methylated may include the MVPs identified in SEQ ID NOS 1 to 3 and denoted by [CG], or may include the MVPs identified in SEQ ID NOS 1 to 5 and denoted by [CG], or may include the MVPs identified in SEQ ID NOS 1 to 10 and denoted by [CG], or may include the MVPs identified in SEQ ID NOS 1 to 20 and denoted by [CG], or may include the MVPs identified in SEQ ID NOS 1 to 30 and denoted by [CG], or may include the MVPs identified in SEQ ID NOS 1 to 40 and denoted by [CG], or may include the MVPs identified in SEQ ID NOS 1 to 50 and denoted by [CG], or may include the MVPs identified in SEQ ID NOS 1 to 60 and denoted by [CG], or may include the MVPs identified in SEQ ID NOS 1 to 70 and denoted by [CG], or may include the MVPs identified in SEQ ID NOS 1 to 80 and denoted by [CG], or may include the MVPs identified in SEQ ID NOS 1 to 90 and denoted by [CG], or may include the MVPs identified in SEQ ID NOS 1 to 100 and denoted by [CG].

In one embodiment, the group of MVPs (i.e. those MVPs the methylation status of which are to be determined) may comprises all 150 of the MVPs identified in SEQ ID NOS 1 to 150 and denoted by [CG], and in this method bladder cancer is diagnosed in the individual when at least 40 of the MVPs selected from the MVPs identified in SEQ ID NOS 1 to 150 and denoted by [CG] are methylated, and in this method the MVPs determined to be methylated include the MVPs identified in SEQ ID NOS 1 to 10 and denoted by [CG].

Bioinformatic Tools and Statistical Metrics

Software programs which aid in the in silico analysis of bisulphite converted DNA sequences and in primer design for the purposes of methylation-specific analyses are generally available and have been described previously [57, 58, 59].

Sensitivity and specificity metrics for bladder cancer diagnosis based on the MVP methylation status assays described herein may be defined using standard receiver operating characteristic (ROC) statistical analysis [52]. In ROC analysis 100% sensitivity corresponds to a finding of no false negatives, and 100% specificity corresponds to a finding of no false positives.

Based on analyses conducted using a panel of 150 MVP biomarkers, a bladder cancer diagnostic assay in accordance with the invention described herein can achieve a ROC sensitivity of 90% or greater, 91% or greater, 92% or greater, 93% or greater, 94% or greater, 95% or greater, 96% or greater, 97% or greater, 98% or greater or 99%. The ROC sensitivity may be 100%.

Diagnostic assays in accordance with the invention can achieve a ROC specificity of 90% or greater, 91% or greater, 92% or greater, 93% or greater, 94% or greater, 95% or greater, 96% or greater, 97% or greater, 98% or greater or 99%. The ROC specificity may be 100%.

Diagnostic assays in accordance with the invention may have an associated combination of ROC sensitivity and ROC specificity values wherein the combination is any one of the above-listed sensitivity values and any one of the above-listed specificity values, provided that the sensitivity value is equal to or less than the specificity value.

Thus, the ROC specificity may be 100% and the ROC sensitivity may be 90% or greater, 91% or greater, 92% or greater, 93% or greater, 94% or greater, 95% or greater, 96% or greater, 97% or greater, 98% or greater, 99% or 100%.

The ROC specificity may be 99% and the ROC sensitivity may be 90% or greater, 91% or greater, 92% or greater, 93% or greater, 94% or greater, 95% or greater, 96% or greater, 97% or greater, 98% or 99%.

The ROC specificity may be 98% and the ROC sensitivity may be 90% or greater, 91% or greater, 92% or greater, 93% or greater, 94% or greater, 95% or greater, 96% or greater, 97% or 98%.

The ROC specificity may be 97% and the ROC sensitivity may be 90% or greater, 91% or greater, 92% or greater, 93% or greater, 94% or greater, 95% or greater, 96% or 97%.

The ROC specificity may be 96% and the ROC sensitivity may be 90% or greater, 91% or greater, 92% or greater, 93% or greater, 94% or greater, 95% or 96%.

The ROC specificity may be 95% and the ROC sensitivity may be 90% or greater, 91% or greater, 92% or greater, 93% or greater, 94% or 95%.

The ROC specificity may be 94% and the ROC sensitivity may be 90% or greater, 91% or greater, 92% or greater, 93% or 94%.

The ROC specificity may be 93% and the ROC sensitivity may be 90% or greater, 91% or greater, 92% or 93%.

The ROC specificity may be 92% and the ROC sensitivity may be 90% or greater, 91% or 92%.

The ROC specificity may be 91% and the ROC sensitivity may be 90% or 91%.

The ROC specificity may be 90% and the ROC sensitivity may be 90%. Preferably, the assay may achieve a ROC sensitivity of 95% or greater and a ROC specificity of 90% or greater; preferably a ROC sensitivity of 96% and a ROC specificity of 97%.

Figure 5:
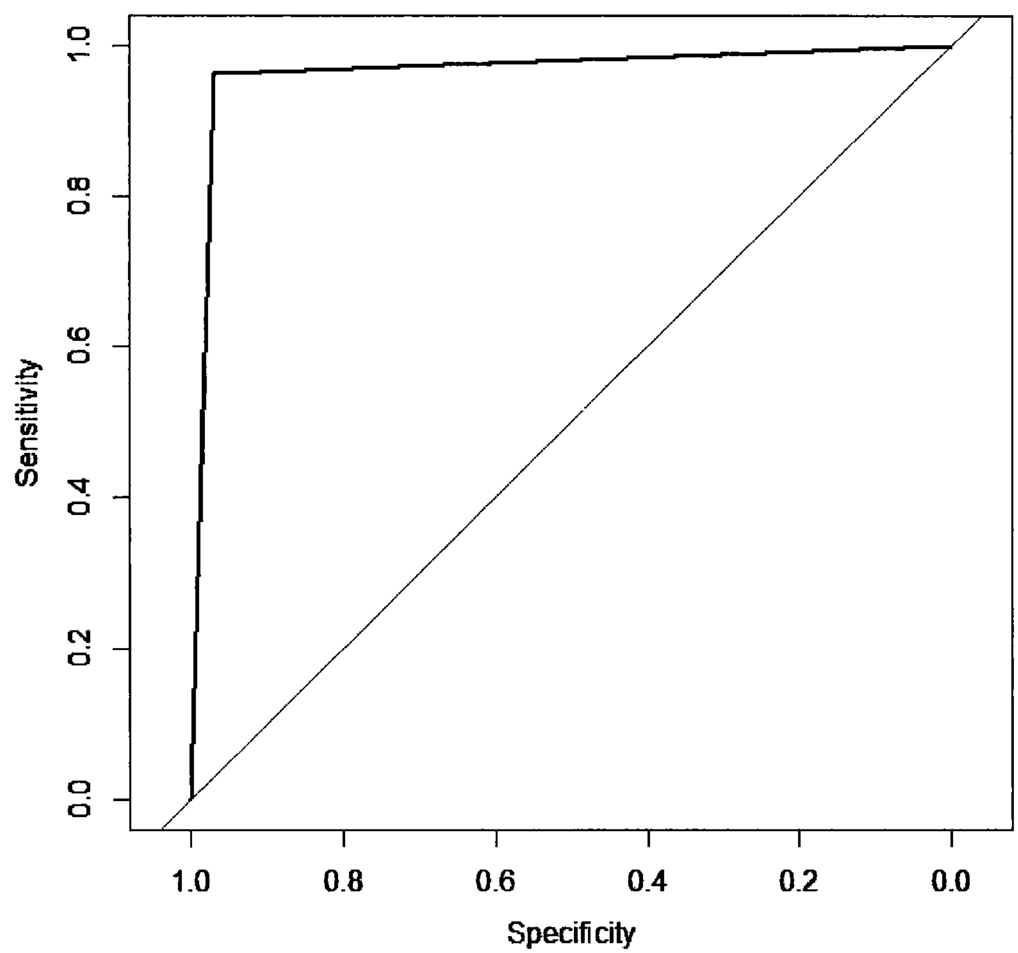
FIG. 5. ROC plot for UroMark model for the detection of bladder cancer in urine.
Figure 7:
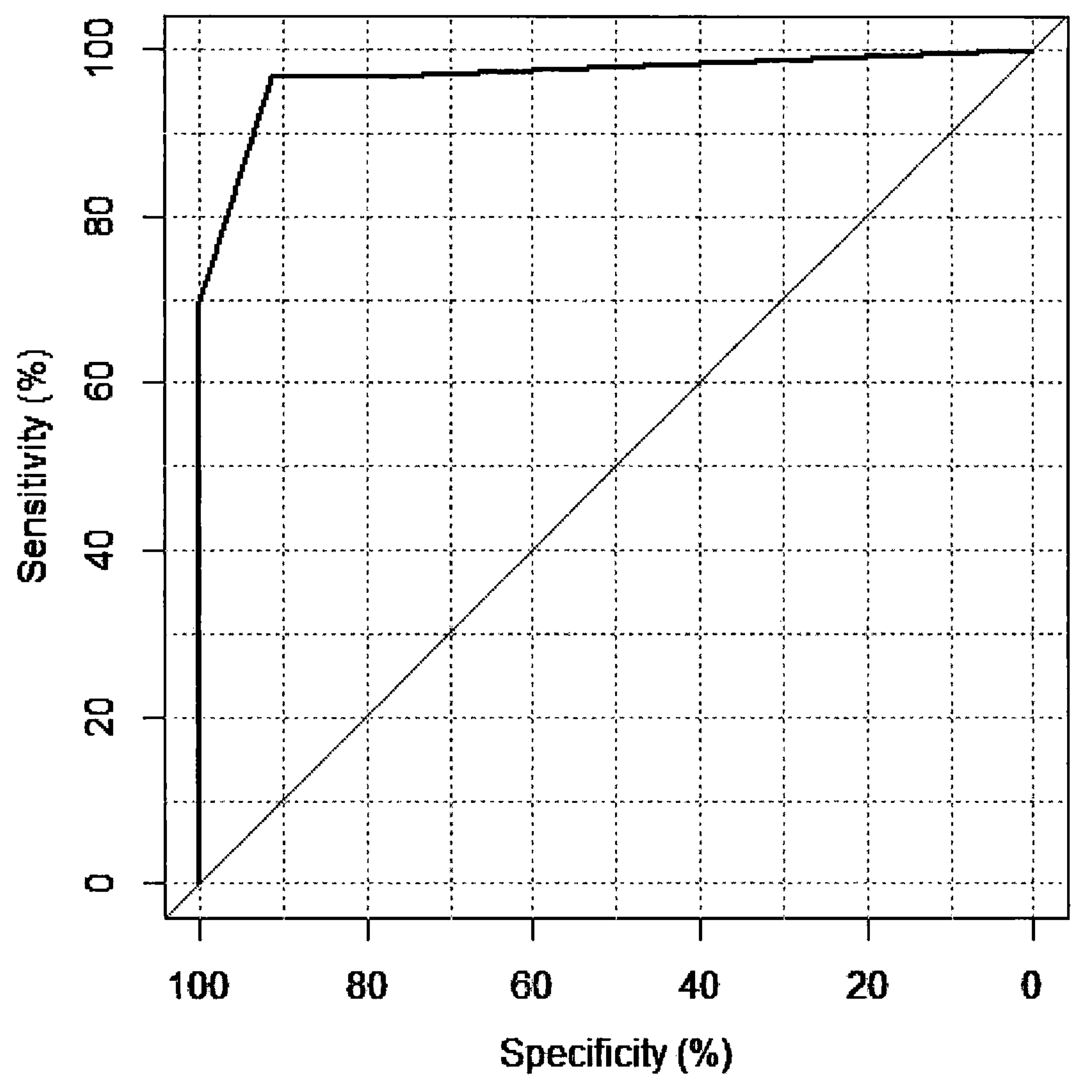
FIG. 7. ROC plot for UroMark model for the detection of bladder cancer from 176 unique urine samples (98 non-cancer urines and 78 cancer urines).

ROC plots corresponding to example methods representative of the diagnostic methods defined herein are presented at FIGS. 5 and 7, demonstrating the exquisite sensitivity and selectivity of the MVP-based assays. This contrasts with assays conducted with smaller panels of biomarkers, which have been described previously. Thus, comparative data demonstrate the superior predictive power of the assays defined herein.

A further metric which can be employed to classify the accuracy of the MVP-based assays is ROC AUC. In ROC analysis, the area under the curve of a ROC plot (AUC) is a metric for binary classification. In a random binary classifier the number of true positives and false positives will be approximately equal. In this situation the AUC score for the ROC plot will be 0.5. In a perfect binary classifier the number of true positives will be 100% and the number of false positives will be 0%. In this situation the AUC score for the ROC plot will be 1.

Based on analyses conducted using biomarkers described herein, a bladder cancer diagnostic assay in accordance with the invention can achieve a ROC AUC of 0.90 or greater, 0.91 or greater, 0.92 or greater, 0.93 or greater, 0.94 or greater, 0.95 or greater, 0.96 or greater, 0.97 or greater, 0.98 or greater, 0.99 or 1. Preferably the diagnostic assay can achieve a ROC AUC of 0.98 or greater.

Bladder cancer diagnostic tests based on the MVP methylation status assays described herein may also be characterised using a Negative Predictive Value (NPV) metric. The NPV is a measure of the proportion of negative results that are true negative results.

Based on analyses conducted using a panel of 150 MVP biomarkers, a bladder cancer diagnostic assay in accordance with the invention described herein can achieve an NPV of 90% or greater, 91% or greater, 92% or greater, 93% or greater, 94% or greater, 95% or greater, 96% or greater, 97% or greater, 98% or greater or 99% or 100%.

Biological Samples

The bladder cancer diagnostic assays described herein may be performed on any suitable biological material obtained from the patient. Preferred biological material is urine. However, samples of bladder tissue, e.g. obtained via biopsy or aspirates, or obtained from preserved samples (e.g. cryopreserved material, tissue sections etc.) may be used. Samples of biological material may also include solid tissue samples, aspirates, samples of biological fluids, blood, serum, plasma, ascitic fluid, lymph, peripheral blood, cerebrospinal fluid, fine needle aspirate, saliva, sputum, bone marrow, skin, epithelial samples (including buccal, cervical or vaginal epithelia) or other tissue derived from the ectoderm, vaginal fluid, semen etc. Tissue scrapes may include biological material from e.g. buccal, oesophageal, bladder, vaginal, urethral or cervical scrapes. The cells of the sample may comprise inflammatory cells, such as lymphocytes.

Any of the assays and methods described herein may involve providing a biological sample from the patient as the source of patient DNA for methylation analysis.

Any of the assays and methods described herein may involve obtaining patient DNA from a biological sample which has previously been obtained from the patient.

Any of the assays and methods described herein may involve obtaining a biological sample from the patient as the source of patient DNA for methylation analysis. Procedures for obtaining a biological sample from the patient may be non-invasive, such as collecting cells from urine. Alternatively, invasive procedures such as biopsies may be used.

In the methods described herein the level of detection is such that 2 tumor cells may be detected in a sample comprising 150,000 cells or more. In such methods the sample may comprise 160,000 cells or more, 170,000 cells or more, 180,000 cells or more, 190,000 cells or more, 200,000 cells or more, 210,000 cells or more, 220,000 cells or more, 230,000 cells or more, 240,000 cells or more, 250,000 cells or more, 260,000 cells or more, 270,000 cells or more, 280,000 cells or more, 280,000 cells or more, or 300,000 cells or more.

In any such method, the number of tumor cells that can be detected is 10 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, 1000 or more, 2000 or more, 3000 or more, 4000 or more, 5000 or more, 6000 or more, 7000 or more, 8000 or more, 9000 or more, 10000 or more, 20000 or more, 30000 or more, 40000 or more, 50000 or more, 60000 or more, 70000 or more, 80000 or more, 90000 or more or 100000 or more.

Methods of Treatment

The invention also encompasses the performance of one or more treatment steps following a positive diagnosis of bladder cancer by the diagnostic methods described herein.

Thus the invention also encompasses a method of treating bladder cancer in an individual comprising:

(a) obtaining DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention also encompasses a method of treating bladder cancer in an individual comprising:

(a) providing DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention also encompasses a method of treating bladder cancer in an individual comprising:

(a) determining whether each one of a group of MVPs selected from a panel comprising the MVPs identified in SEQ ID NOS 1 to 150 and denoted by [CG] is methylated in DNA from a sample from the individual, wherein the group comprises at least 25 of the MVPs identified in SEQ ID NOS 1 to 150 and denoted by [CG];

(b) diagnosing bladder cancer in the individual when at least 25 MVPs of the group of (a) are methylated; and (c) administering one or more bladder cancer treatments to the individual.

The invention also encompasses a method of treating bladder cancer in an individual comprising administering one or more bladder cancer treatments to the individual, wherein the individual has been diagnosed with bladder cancer by steps comprising:

(a) providing DNA from a sample from the individual and determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (b) diagnosing bladder cancer in the individual when at least 25 MVPs of the group of (a) are methylated.

In any of the above-described methods of treating bladder cancer, the group of MVPs which are selected from a panel comprising the MVPs identified in SEQ ID NOS 1 to 150 and denoted by [CG] (i.e. the group of MVPs whose methylation status is to be determined) may comprise any number of MVPs as described and defined herein, provided that the group comprises at least 25 of the MVPs identified in SEQ ID NOS 1 to 150 and denoted by [CG]. In any of these methods, bladder cancer may be diagnosed in the individual when the number of MVPs of the group which are determined to be methylated is any number of MVPs as described and defined herein, provided that at least 25 of the MVPs identified in SEQ ID NOS 1 to 150 and denoted by [CG] are determined to be methylated.

Thus, the invention encompasses administration of one or more surgical procedures, one or more chemotherapeutic agents, one or more immunotherapeutic agents, one or more radiotherapeutic agents, one or more hormonal therapeutic agents or any combination of the above following a positive diagnosis of bladder cancer.

Surgical procedures include transurethral resection of bladder tumor (TURBT), cystectomy, open radical cystectomy (ORC), laparoscopic radical cystectomy (LRC) and robot-assisted radical cystectomy (RARC).

Chemotherapeutic agents include the following. Alkylating agents, which include the nitrogen mustards, nitrosoureas, tetrazines, aziridines, cisplatin and platinum based derivatives, as well as the non-classical alkylating agents. Antimetabolites, which include the anti-folates, fluoropyrimidines, deoxynucleoside analogues and thiopurines. Microtubule disrupting agents, which include the vinca alkaloids and taxanes, as well as dolastatin 10 and derivatives thereof. Topoisomerase inhibitors, which include camptothecin, irinotecan and topotecan. Topoisomerase II poisons, which include etoposide, doxorubicin, mitoxantrone and teniposide. Topoisomerase II catalytic inhibitors, which include novobiocin, merbarone, and aclarubicin. Cytotoxic antibiotics, which include anthracyclines, actinomycin, bleomycin, plicamycin, and mitomycin.

Combinations of agents include but are not limited to MVAC (Methotrexate, Vinblastine, Vinblastine and Vinblastine), Gem-Cis (GC) (Gemcitabine and Cisplatin), Lapatinib and gemcitabine.

Immunotherapeutics include bacilli Calmette-Guérin (BCG) immunotherapy as well as monoclonal antibodies and antibody-drug conjugates. Antibody-drug conjugates include antibodies conjugated to microtubule disrupting agents and DNA modifying agents as described above.

Combination therapies include intravesical, sequential BCG, followed by electromotive administration (EMDA) of MMC (EMDA-MMC) as well as microwave-induced bladder wall hyperthermia (HT) and intravesical MMC.

Cancer therapeutic agents are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". Effective amounts for a given purpose will depend on the severity of the disease as well as the weight and general state of the subject. As used herein, the term "subject" includes any human.

Arrays

The invention also encompasses arrays capable of discriminating between methylated and non-methylated forms of MVPs as defined herein; the arrays may comprise oligonucleotide probes specific for methylated forms of MVPs as defined herein and oligonucleotide probes specific for non-methylated forms of MVPs as defined herein.

By "specific" it is meant that the probes comprise sequences which are complementary to those of the oligonucleotides comprising the MVP such they may hybridize, particularly under stringent conditions.

In some embodiments the array is not an Illumina Infinium HumanMethylation450 BeadChip array (Infinium HumanMethylation450 BeadChip array).

Separately or additionally, in some embodiments the number of MVP-specific oligonucleotide probes of the array is less than 482,421, preferably 482,000 or less, 480,000 or less, 450,000 or less, 440,000 or less, 430,000 or less, 420,000 or less, 410,000 or less, or 400,000 or less, 375,000 or less, 350,000 or less, 325,000 or less, 300,000 or less, 275,000 or less, 250,000 or less, 225,000 or less, 200,000 or less, 175,000 or less, 150,000 or less, 125,000 or less, 100,000 or less, 75,000 or less, 50,000 or less, 45,000 or less, 40,000 or less, 35,000 or less, 30,000 or less, 25,000 or less, 20,000 or less, 15,000 or less, 10,000 or less, 5,000 or less, 4,000 or less, 3,000 or less or 2,000 or less.

The invention further encompasses the use of any of the arrays as defined herein in any of the methods which require determining the methylation status of MVPs for the purposes of diagnosing bladder cancer cells in an individual.

Kits

Any of the arrays as defined herein may be comprised in a kit.

The kit may comprise any array as defined herein.

The kit may comprise any array as defined herein together with instructions for use.

The kit may additionally comprise a DNA modifying regent, such as a bisulphite reagent.

The kit may additionally comprise reagents for amplifying DNA, such as primers directed to any of the MVPs as defined herein as identified in SEQ ID NOS 1 to 150 (see Table 2).

Methods of Determining a Methylation Profile of a Sample

The invention further encompasses a method of determining a methylation profile of a sample from an individual, the method comprising:

i. providing DNA from a sample from the individual;

ii. determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and iii. based on the methylation status of the MVPs of the group, determining a methylation profile of the sample.

In any of the above-described methods of determining a methylation profile of a sample, the group of MVPs which are selected from a panel comprising the MVPs identified in SEQ ID NOS 1 to 150 and denoted by [CG] (i.e. the group of MVPs whose methylation status is to be determined) may comprise any number of MVPs as described and defined herein, provided that the group comprises at least 25 of the MVPs identified in SEQ ID NOS 1 to 150 and denoted by [CG].

Furthermore, in any such methods, the methylation status of MVPs may be determined using any of the arrays described herein.

Further Methods

In any of the diagnostic methods described herein, the step of diagnosing bladder cancer in the individual may further comprise:

I. stratifying the grade of the tumor; and/or

II. determining the risk of recurrence of the tumor; and/or

III. determining the risk of progression of non-muscular invasive disease; and/or IV. determining the likely response to treatment therapy.

The invention also encompasses a method of determining the risk of the development of bladder cancer in an individual, the method comprising:

(a) providing DNA from a sample from the individual;

(b) determining whether each one of a group of MVPs selected from a panel comprising the MVPs identified in SEQ ID NOS 1 to 150 and denoted by [CG] is methylated, wherein the group comprises at least 25 of the MVPs identified in SEQ ID NOS 1 to 150 and denoted by [CG]; and (c) based on the methylation status of the MVPs of the group, determining the risk of the development of bladder cancer in the individual.

In any such method of determining the risk of the development of bladder cancer in an individual, the group of MVPs which are selected from a panel comprising the MVPs identified in SEQ ID NOS 1 to 150 and denoted by [CG] (i.e. the group of MVPs whose methylation status is to be determined) may comprise any number of MVPs as described and defined herein, provided that the group comprises at least 25 of the MVPs identified in SEQ ID NOS 1 to 150 and denoted by [CG].

Furthermore, in any such methods, the methylation status of MVPs may be determined using any of the arrays described herein.

Further Uses

The invention also encompasses the use of a group of MVPs in the diagnosis of bladder cancer in an individual or in determining the risk of the development of bladder cancer in an individual.

In any such use, the group of MVPs are selected from a panel comprising the MVPs identified in SEQ ID NOS 1 to 150 and denoted by [CG].

In any such use, the group of MVPs may comprise any number of MVPs as described and defined herein, provided that the group comprises at least 25 of the MVPs identified in SEQ ID NOS 1 to 150 and denoted by [CG].

In any of the above-described uses, the diagnosis of bladder cancer in an individual or the determination of the risk of the development of bladder cancer in an individual may be performed by any of the respective methods described and defined herein. Furthermore, in any such methods, the methylation status of MVPs may be determined using any of the arrays described herein.

The invention is illustrated by the following Examples:

EXAMPLES

Materials and Methods

Introduction

Emerging techniques that utilize next-generation DNA sequencing platforms hold particular promise for the development of highly sensitive epigenetic biomarker panels. For example, the microdroplet-based PCR amplification of bisulphite converted DNA, followed by next-generation sequencing of the amplified target loci developed by RainDance Technologies [30] enables the sensitive, specific and simultaneous amplification of up to 20,000 bisulfite-converted target loci. Highly parallel microdroplet-based PCR amplification of bisulphite-converted DNA has shown utility in the validation of epigenetic alterations in a range of tissues [31-33]. However, as yet it has not been applied to the development of non-invasive diagnostic biomarkers for the detection of bladder cancer.

To derive a sensitive assay for the detection of bladder cancer, the inventors have performed one of the largest independent studies of genome-wide methylation in bladder cancer to date. From this, a panel of bladder-specific epigenetic biomarkers have been defined and the sensitivity and specificity of a 150 loci panel using RainDrop-BS [31] on urinary DNA have been validated for the detection of bladder cancer with a high degree of diagnostic precision.

Study Population

Genome-wide DNA methylation profiling was performed on DNA from 81 bladder cancers and 30 age-matched normal urothelium samples collected from UCLH (London) Department of Urology and CIEMAT (Madrid). The cohort included 35 low-grade non-muscle-invasive cancers. Pathological review of representative H&E sections was conducted to include specimens with tumor cellularity >80%. Blood methylome data was download from the MARMAL-aid database ([34]; see the Marmal-aid website on the world wide web).

Independent validation data were obtained from the Cancer Genome Atlas Project (see The Cancer Genome Atlas Project at the National Cancer Institute website on the world wide web), consisting of MIBC bladder cancer and 20 normal urothelium samples.

For validation studies sequential urine samples were collected from patients attending UCLH one-stop haematuria and surveillance cystoscopy clinics (n=86 bladder cancer, n=96 non-cancer controls).

Urine Collection

Urine samples were obtained from patients attending haematuria clinics or undergoing cystoscopy for recurrent bladder cancer at University College Hospital. For comparison of clinic versus home urine samples, patients were asked to supply three samples: a clinic sample and two home samples, one of which should be a first void. 40-100 ml were obtained per sample. The home urine kit for one sample comprised up to four 25 ml sterile tubes, mailing tubes with absorbent pads and a pre-addressed padded envelope, designed to fit through a Royal Mail post box.

DNA Extraction and Quantification

Urinary DNA was extracted using a DNeasy blood and tissue kit (Qiagen, UK) in accordance with the manufacturer's instructions. DNA was quantified by spectrophotometry (Nanodrop 1000) and fluorometry (Qubit ds DNA HS assay, Invitrogen, UK).

RainDance Microdroplet PCR

For microdroplet PCR, 7.20 μl of bisulfite-treated (and optionally, whole-genome amplified) DNA were added to 4.70 μl of 10× High-Fidelity Buffer (Invitrogen), 1.80 μl of 50 mM $MgSO_4$ (Invitrogen), 1.62 μl of 10 mM dNTP solution mix (NEB), 3.60 μl of 4 M betaine solution (Sigma-Aldrich), 3.60 μl of droplet stabilizer (RainDance Technologies), 1.80 μl of 100% dimethyl sulfoxide (Sigma-Aldrich) and 0.72 μl of 5 U/μl Platinum Taq Polymerase High-Fidelity (Invitrogen), to a total volume of 25 μl. The sample plate was sealed using an ALPS 50V microplate heat sealer (Thermo Scientific).

The bisulfite-treated genomic DNA template mix was then applied to a fully automated ThunderStorm system (RainDance Technologies) following the manufacturer's instructions. In brief, primer panel droplets (MethylSeq Solution, RainDance Technologies) were dispensed to a microfluidic chip. The DNA template mix was converted into droplets within the microfluidic chip. The primer pair droplets and template droplets were then paired together in a 1:1 ratio. Paired droplets passed through an electric field inducing the discrete droplets to coalesce into a single PCR droplet (26 pl); approximately 1 million PCR droplets are collected per sample.

PCR droplets were processed in a PTC-225 thermocycler (MJ Research) as follows: 94° C. for 2 min; 55 cycles of 94° C. for 30 s, 54° C. for 45 s, 68° C. for 80 s; followed by 68° C. for 10 min; 4° C. until further processing. The ramp rate was set to 1° C. per second. Following PCR amplification, 70 μl of droplet destabilizer (RainDance Technologies) were added to each sample to break the PCR droplet emulsion and release the amplicons contained within the droplets. The solution was mixed well and incubated for 15 min at RT. Samples were purified using Agencourt AMPure XP magnetic beads (Beckman Coulter) following the manufacturer's protocol. For each sample, 234 μl of beads were used. Samples were eluted from magnetic beads in 40 μl of Buffer. The integrity and concentration (fragment range: 120-300 bp) of purified amplicon DNA were assessed using a High Sensitivity DNA Kit (Agilent Technologies) on a 2100 Bioanalyzer (Agilent Technologies).

Methylation Array 500 ng of DNA was bisulphite converted and hybridised to the Infinium 450K Human Methylation array and processed in accordance with the manufacturer's recommendations. DNA bisulphite conversion was carried out using the EZ DNA Methylation kit (Zymo Research) as per the manufacturer's instructions. Samples were processed in a single batch. R statistical software (version 2.14.0 [35]) was used for the subsequent data analysis. The ChAMP pipeline was used to extract and analyze data from iDat files, samples were normalised using BMIQ [36, 37]. Raw β values (methylation value) were subjected to a stringent quality control analysis as follows: samples showing reduced coverage were removed and only probes with detection levels above background across all samples were retained (detection P<0.01). DMRs (Differentially Methylated Regions) were determined using Lasso [38, 39].

High-Throughput DNA Sequencing

The pooled sequencing library (12 pM) and custom sequencing primers (0.5 μM) were applied to a MiSeq-cycle PE consumable cartridge (Illumina) according to the manufacturer's protocol. The DNA sequences of the custom sequencing primers are provided in Table 2 below. Sequencing was performed on a MiSeq DNA sequencer (Illumina) using 75-bp paired-end reads.

The RainDance ThunderStorm®. System was also used for the sequencing of nucleic acids (see the RainDance ThunderStorm System website on the world wide web).

Data and Statistical Analyses

Sequencing adapters were trimmed from the raw sequencing reads using the fastq-mcf tool of ea-utils v1.1.2-537 [60]. Trimmed sequencing data were mapped to an in silico bisulfite-converted human reference genome (GRCh37) using Bismark v0.7.12 [40, 61]. Methylation information was extracted using the methylation_extractor tool of Bismark v0.7.12 [61]. Targeted DNA sequencing analyses were performed using the R package TEQC v3.2.0.25.

Example 1: Methylation Profiling of Low and High Trade Bladder Cancer

The epigenetic alterations associated with bladder cancer were initially defined by performing genome-wide DNA methylation profiling on DNA from 81 high-grade and 30 normal urothelium.

Supervised analysis, using a Wilcoxon rank-sum test to assign directionality, was used to identify MVPs (Methylation Variable Positions) between bladder cancer and normal tissue. MVPs were selected on the basis of statistical significance (Wilcoxon P-value>0.001). An additional filter of Δβ>0.30(+/−) was applied to compensate for not taking into account the absolute difference in methylation between the groups. The cut-off is empirically defined to result in a false discovery rate (FDR) of <2% and reduced candidate loci to those with largest methylation differences and therefore greatest potential for a discriminatory effect. A total of 9786 MVPs met these requirements (1746 hypermethylated MVPs, 8040 hypomethylated MVPs) (FIG. 1).

Example 2: Bladder Cancer Specific Urinary Biomarkers

To define a DNA methylation biomarker panel, those loci which were determined to be methylated (β>50%) in at least 50% of cancers and unmethylated in normal urothelium (β<10%) were identified. By "methylated (β>50%)", as discussed herein in relation to the development of this initial DNA methylation biomarker panel, it is meant that for any given locus, >50% of cells in a patient sample are determined to be methylated with respect to that MVP. In order to remove potential false positive biomarkers and better define alterations which are bladder cancer specific, whole blood and urine from 10 patients attending hematuria clinics and who had a confirmed non-cancer diagnosis was also profiled. Subsequently, any loci which showed any methylation (β>10%) in DNA from these non-cancer control urine and bloods were removed. A maximum of 432 loci were identified which are unmethylated in non-cancers and methylated (β>50%) in the majority of cancer tissue.

Figure 2:
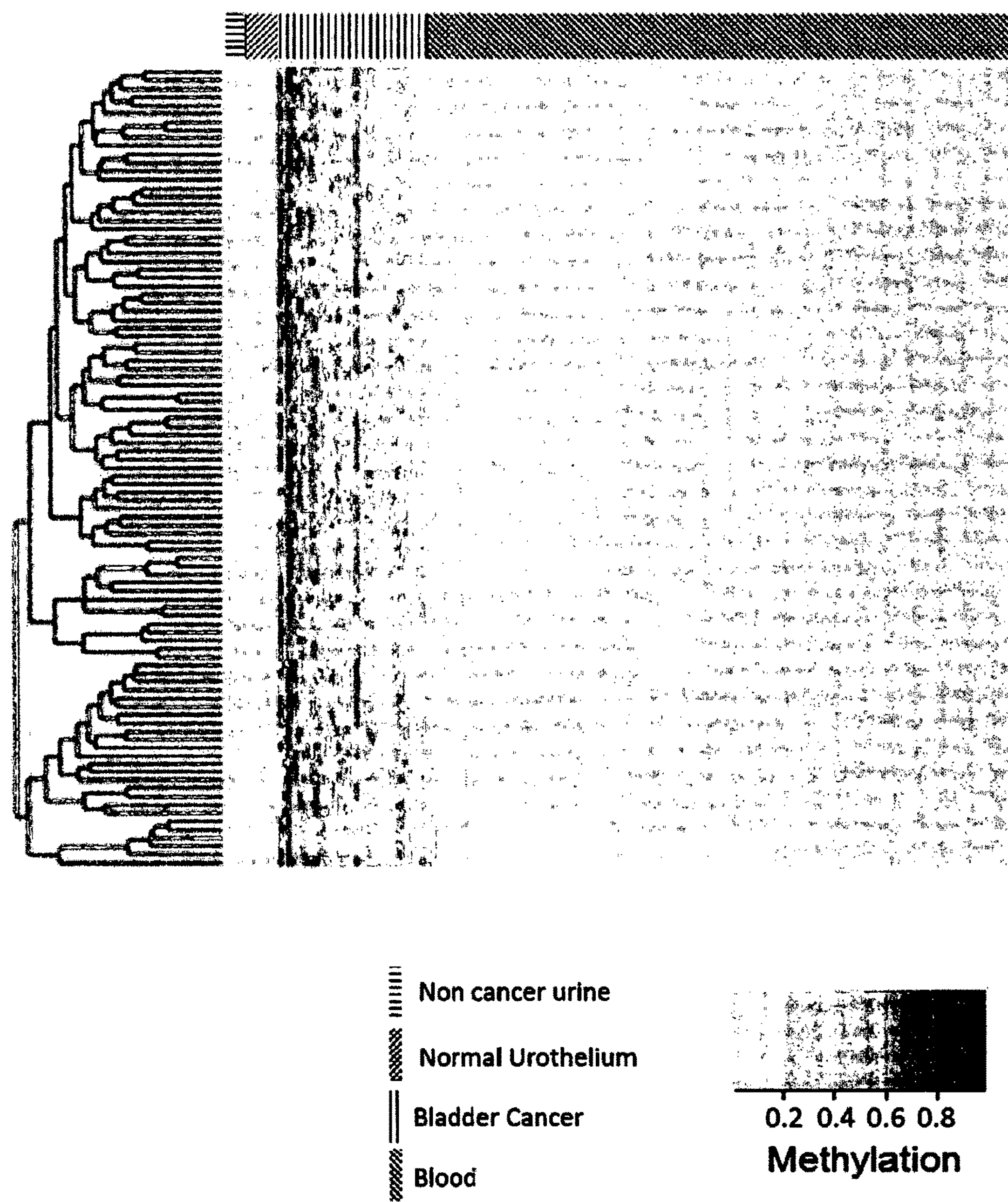
FIG. 2. Heatmap of the 150 UroMark loci for non-cancer urine (n=10), normal urothelium (n=30), bladder cancer (n=81) and blood (n=489).
Figure 3:
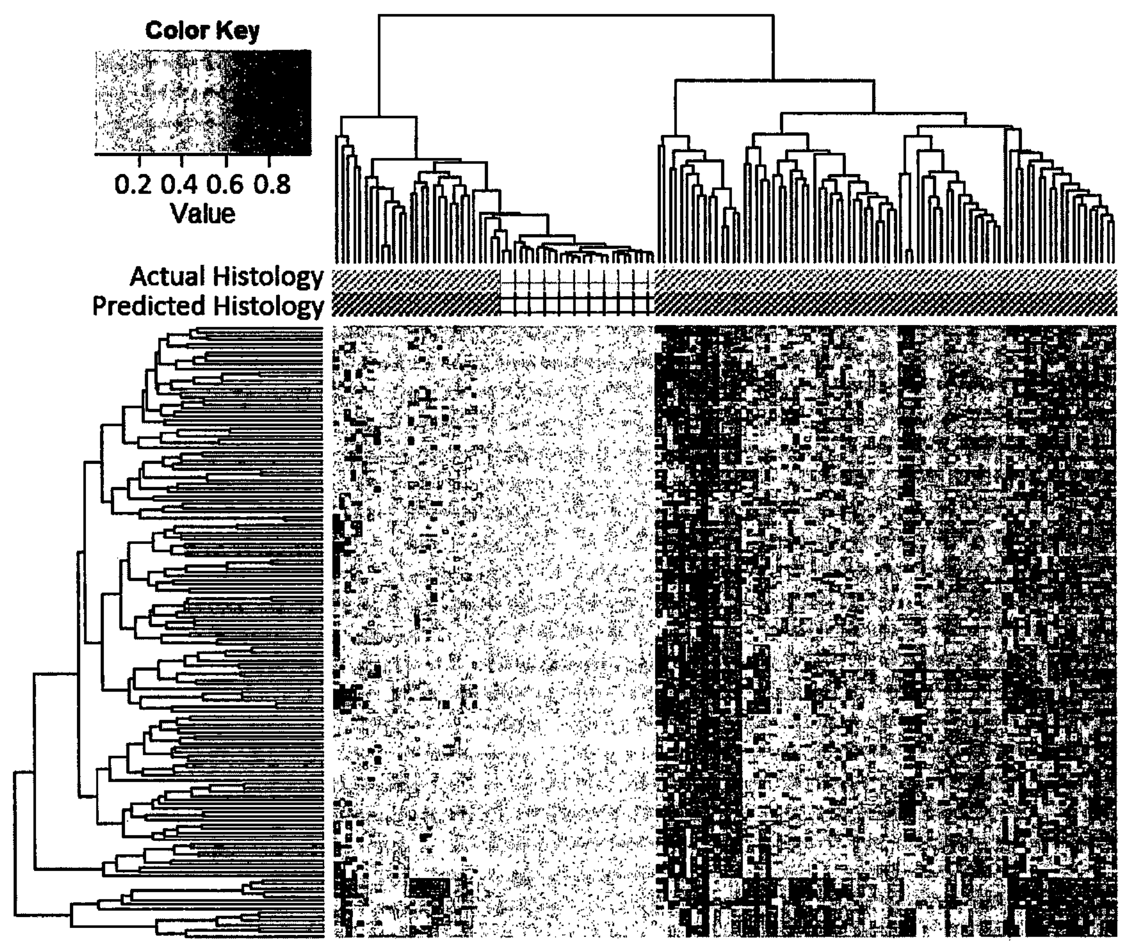
FIG. 3. Heat map of the 150 loci involved in the UroMark assay for normal urothelium (Blue) bladder cancer (Red) compared with the predicted (Light blue/light red) and actual (Blue/Red) status of bladder cancer.
Figure 4:
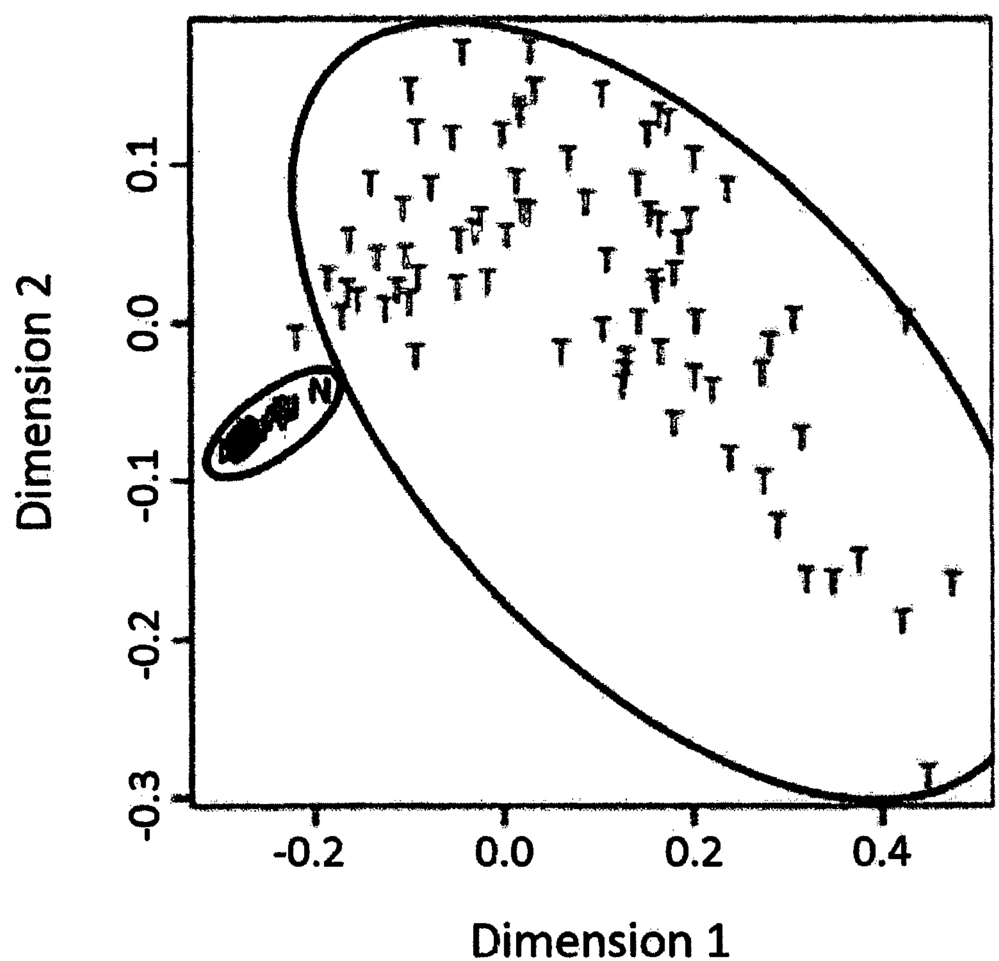
FIG. 4. MDS plots for bladder tumour and normal urothelium based on the methylation state of 150 loci in bladder cancer samples from UCL and TCGA Bladder Cancer. The MDS (Multidimensional scaling) plot represents the dissimilarly of phenotypes based on the methylation state of the 150 loci with the panel, and clearly shows that the 150 marker can accurately separate tumour from normal bladder. Axis represent the Euclidean distance between samples.
Figure 4:
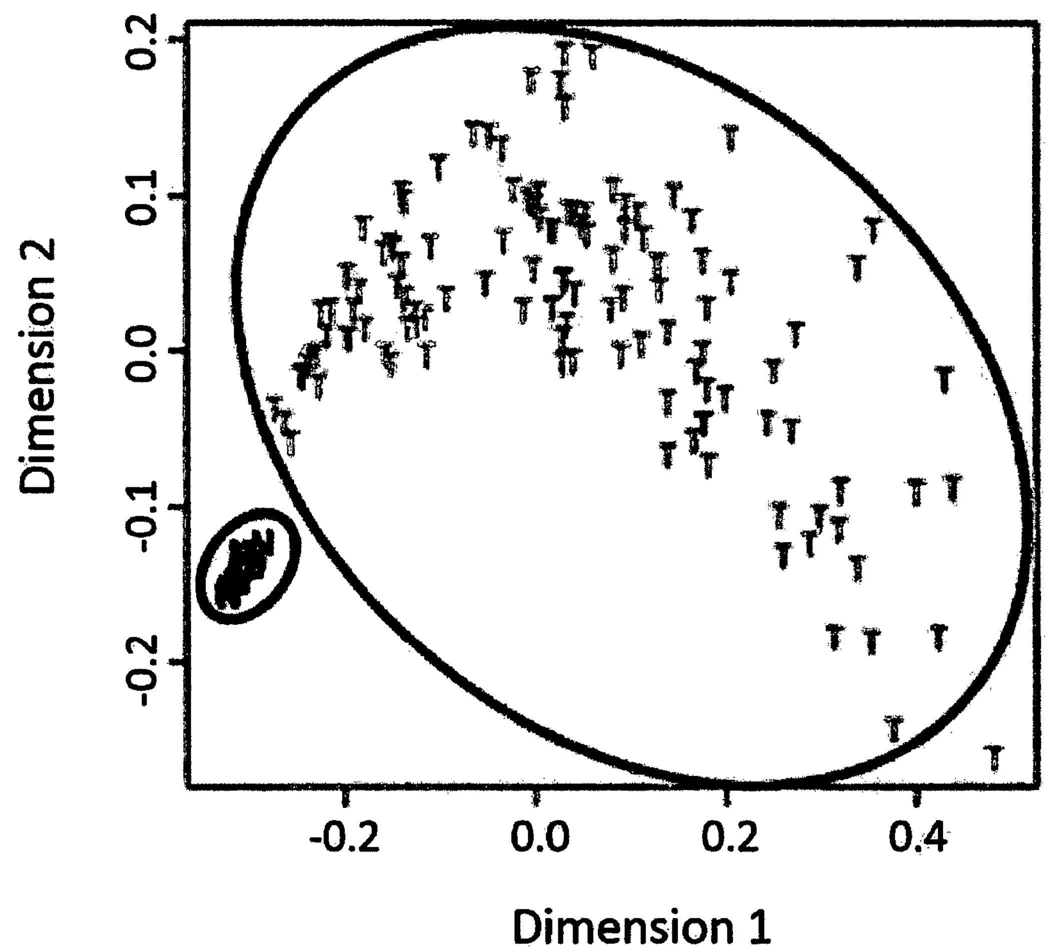

To derive a bladder cancer DNA methylation signature for detection we used the Random Forest framework, which resulted in a classification signature consisting of 150 CpG loci (FIG. 2, see Table 1 below). Using this core set of 150 markers we performed an internal cross validation of the classifier with predicted likelihood values i.e. likelihood of a sample being cancer or not for each sample independent of its relationship to the group of samples. This resulted in a cross validated sensitivity of 100% and specificity of 100% for the detection of cancer, showing that 150 epigenetic loci can clearly stratify normal urothelium from bladder cancer (FIG. 3, FIG. 4).

To determine sensitivity of the 150 CpG (MVP) marker panel for detection of bladder cancer using the classification algorithm, we assessed the methylation profiles of a further 179 bladder cancers (144 muscle invasive and 35 non-muscle invasive) and 20 normal cases. The panel correctly classified all bladder cancers, with a resulting sensitivity and specificity of 1.

Example 3: Validation of Detection Panel

To test the 150 loci panel (epi-signature) for the detection of bladder cancer in urine samples, DNA from urinary sediment cells was obtained from a cohort (n=86) including 52 patients with bladder cancer (low-grade=27, intermediate/high-grade=25) and 34 non-cancer patient controls. Applying the epi-signature to this validation cohort of give a sensitivity of 95% and specificity of 96% and an AUC of 97% for the detection of bladder cancer in this independent validation cohort (FIG. 5).

The large marker panel was also compared to the best performing single markers from the training cohort, this includes CpG loci from regions previously published as potential urinary biomarkers in genes including OTX1, COD1 and MEIS1. For each CpG a methylation threshold was defined, based on the highest β-value obtained from non-bladder cancer controls in the training cohort. This value was then used to predict the likely presence of bladder cancer in the validation cohort. The best performing single markers were combined and a predictive classifier developed to explore the potential for an "oligo panel" based on 3, 5 or 10 markers. Although sensitivities improve over single markers (best single marker 72%, best combined marker 70%), they still do not reach the required level to replace cystoscopy.

Figure 6:
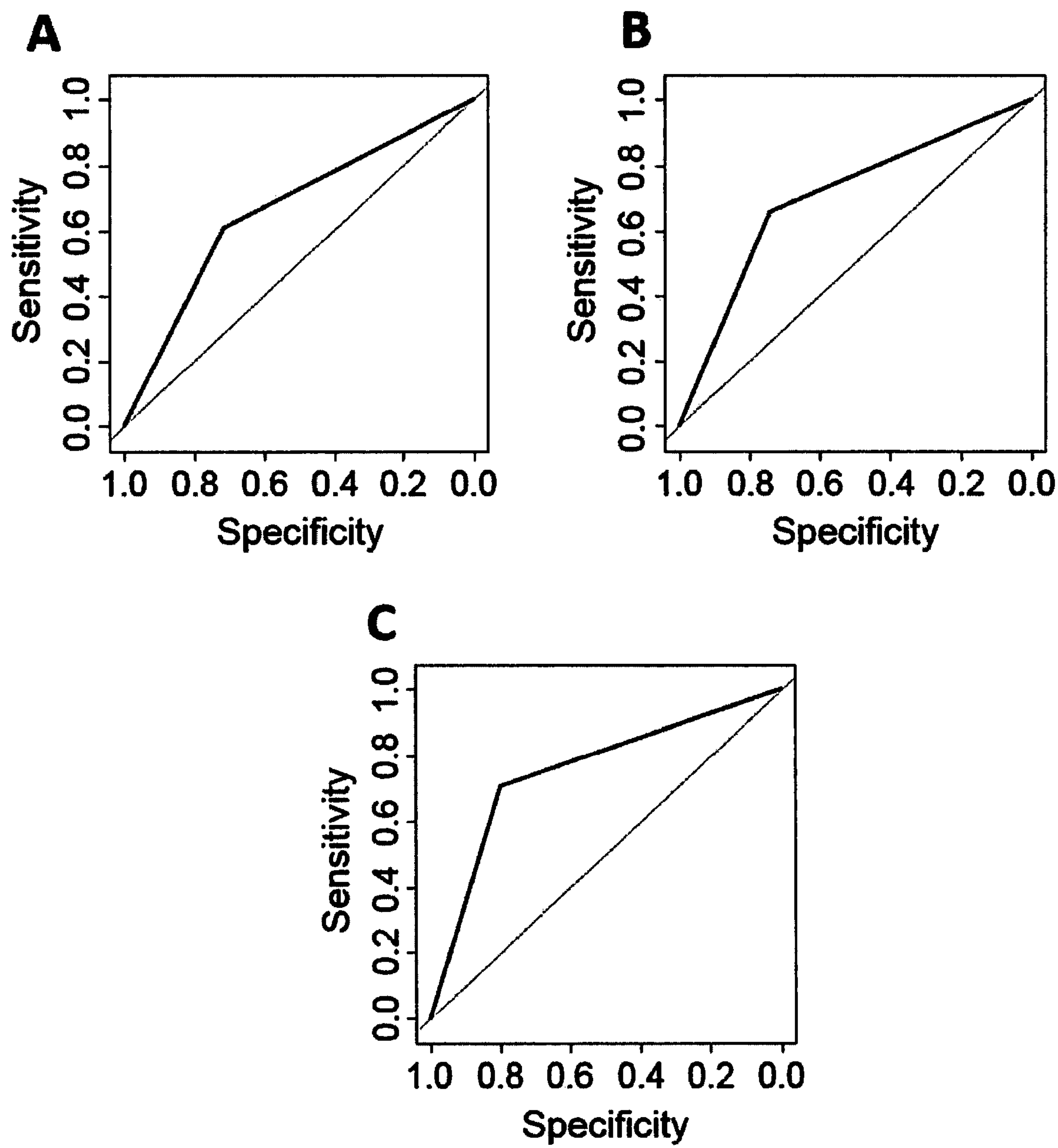
FIG. 6. ROC plots for top performing (A) 3, (B) 5 and (C) 10 marker panels. Top 3 MVPs are listed as SEQ ID NOs: 1 to 3, Top 5 MVPs are listed as SEQ ID NOs: 1 to 5, Top 10 MVPs are listed as SEQ ID NOs: 1 to 10, all in rank order (see Table 1).

These data show that although single markers perform reasonably well alone or in combination (FIGS. 4-6, Table 1), the sensitivity to detect cancer using single loci or an oligo panel approach is limited and below a detection level desirable for clinical utility. Use of a large panel of markers out performs that of a single marker panel and Table 3 shows the sensitivity, specificity, AUC, PPV and NPV for the top 10 best performing markers and the combined 150 loci signature.

Example 4: Validation of Detection Panel Using High Throughput Technology

RainDrop BS-seq [31], allows large scale targeted bisulphite sequencing of a large number of regions (up to 20,00 unique amplicons) in parallel. This technology has been validated previously and shown to be highly correlated with the 450K methylation array, and its utility with low template input has also been validated [31, 32]. A bisulphite converted sequencing primer panel was designed to measure the methylation state of the 150 selected genomic loci (see Table 2 below). Primers were designed to interrogate both Watson and Crick strands independently where possible. Validation of the urinary epi-signature was conducted using RainDrop BS-seq in a second independent cohort of 96 cases. DNA from urinary sediment cells was obtained from 26 patients with bladder cancer and 64 non-cancer patient controls. Methylation score for each of the 150 loci was generated using the Bismark algorithm, using this data the urinary epi-signature predicted the likely presence of bladder cancer with a sensitivity of 96%, specificity of 97% and an AUC of 0.96.

Combining the methylation data from all validation samples allows an increase in the number of samples tested. Combining samples allowed assessment of 176 unique urine samples, 98 non-cancer urines and 78 cancer urines. The urinary epi-signature predicted the presence of bladder cancer with an AUC=0.98, independent of profiling technology (FIG. 7).

Conclusion

Biomarker-driven early non-invasive detection of bladder cancer has the potential to radically improve the management of this disease. Highly sensitive and specific assays have the potential utility in both the detection of de novo disease in patients attending haematuria clinic and also in the screening for recurrence in existing bladder cancer populations.

Several non-invasive tests are commercially available, and are based on cytology, FISH 311 analysis, and detection of mutations. Despite being FDA approved, the tests have reported sensitivities of 54% to 86% and specificities of 61% to 90% [12, 13, 41]. Performance characteristics are not sufficient to replace cystoscopy and therefore have not been taken up into clinical practice. There is therefore significant room for improvement and development of novel biomarkers, combinations of biomarker panels and the use of novel technologies may be most helpful for this purpose.

DNA methylation patterns are highly cell-specific and the ontogenic stability of these epigenetic events make DNA methylation an ideal biomarker for the detection and diagnosis of disease. Changes in global DNA methylation patterns are a common feature of neoplastic transformation and is a frequent event in bladder cancer. Previous studies have shown that methylation changes between bladder cancer, both non-muscle invasive bladder cancer (NMIBC) and muscle invasive bladder cancer (MIBC) and normal urothelium are reflected in urinary sediment cells from bladder cancer patients, and as such could be a useful diagnostic marker. Several studies now have shown the utility of urinary epigenetic markers in the diagnosis of bladder cancer. However, although these studies have shown good sensitivities and specificities, they have failed to be taken up in clinical practice, predominately because they still do not command the performance characteristics to replace cystoscopy. DNA methylation biomarker assays (along with other DNA based markers, e.g. mutations) have been limited by the low resolution of primary analysis in identifying putative biomarkers, using either a candidate approach or a low-resolution microarray based platforms, and also by the limitations in the technology available for analysing candidate markers in urine. This has resulted in single/small biomarker panels being interrogated in the final biomarker panel [15-23]. However, in order for small biomarker panels to show the sensitivity and specificity to match those of cystoscopy they rely heavily on a low intra and inter tumour heterogeneity across a wide spectrum of disease states [42].

Novel technologies, such as next generation bisulphite sequencing and large scale multiplex PCR, now allow for larger panels of epigenetic biomarkers to be utilised [31, 32]. In order to define the epigenetic alterations involved in bladder cancer development and define a biomarker panel one of the largest unbiased genome wide DNA methylation screens of bladder cancer to date was carried out. Besides allowing an insight into the epigenetic alterations driving bladder cancer development, from these data a panel of the epigenetic biomarkers which has high sensitivity and specificity for detection of bladder cancer was also identified.

A biomarker panel of 150 single CpG loci was defined, which are predictive of bladder cancer. Although only a relatively small cohort, these data show the utility of a using a large panel of epigenetic markers, compared to single marker and small panel biomarker panels. With a sensitivity of 96% and a specificity of 97%, the negative predictive value (NPV) of this test is 97%. This is 1.2 to 8.7 times superior to what can be achieved by PSA (prostate-specific antigen) testing (PPV=30%-43%), mammography (PPV=9%-19%), or fecal occult blood screening (PPV=6%-11%; [43-48]) and similarly to that of cystoscopy (PPV=66.7%-98%) [49].

The inventors have shown that by applying a large scale highly multiplexed next generation assay, which is both highly sensitive and quantitative, the presence of bladder cancer in urine can be detected with a higher sensitivity and specificity than previously published methylation assays, and has a PPV comparable to cystoscopy.

The invention demonstrates that the combination of novel technologies, which allow the interrogation of larger panels, and bladder cancer-specific epigenetic biomarkers can be utilized to detect bladder cancer, allowing a reduction in the number of cystoscopies and consequently improve the quality of life for the patients as well as decrease health care expenditure. Furthermore, the utility of large panel assays allows for the potential of multiple clinical parameters to be evaluated from within the same data. For example, the stratification of tumour grade, recurrence or progression of non-muscular invasive disease, the likely response to therapy for muscular invasive disease or the differential diagnosis of multiple conditions.

Example 5: Optimisation of DNA Sample Handling and Processing

Figure 8:
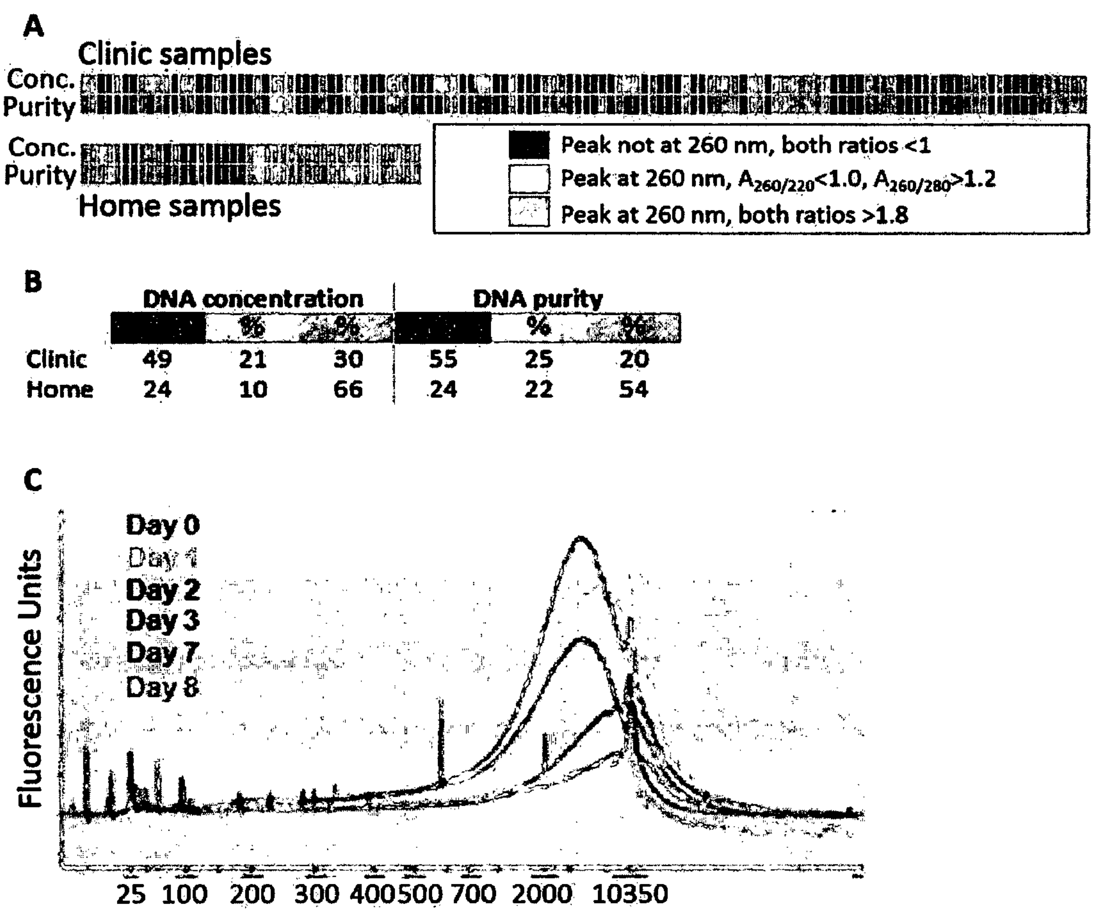
FIG. 8. Comparison of DNA quality (concentration, purity and integrity) from patients' urine. A) Concentration and purity of samples collected in clinic (n=123) compared with samples collected at home (n=41) where red indicates low yield or purity, amber indicates moderate yield and intermediate purity and green is high yield and purity. B) Percentage of samples exhibiting low, intermediate or high yield and purity. C) Representative Bioanalyzer electropherogram demonstrating recovery of high molecular weight of DNA in samples with concentrations quantifiable by spectrophotometry. D) Increased median yield and improved purity of urinary DNA using an extended digest step at 21° C. compared with the manufacturer's standard protocol of 56° C. for 1 hour. E) Comparison of two urine preservation methods: UCL established standard operating procedure versus Norgen urine preservation tubes. The number of bacteria were quantified by qPCR for the rpoB gene and expressed as copies rpoB per copy of human YWHAZ. Data are the mean+/− standard deviation.
Figure 8:
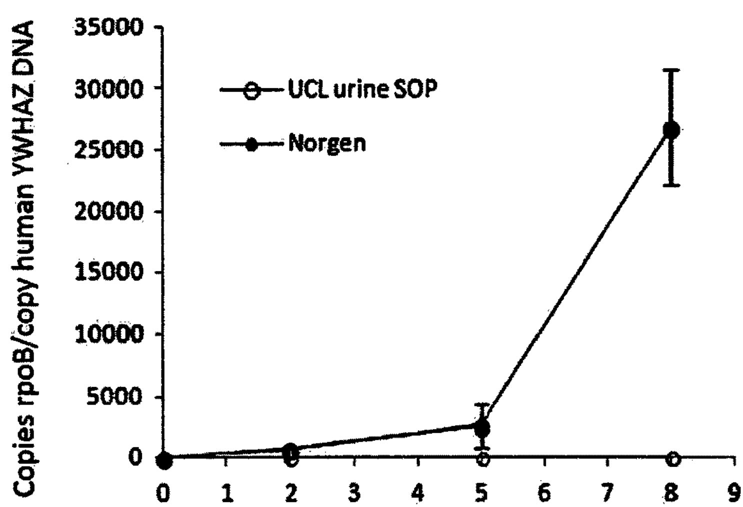

Optimisation studies were performed in order to maximise DNA yield from samples of patient urine. DNA was incubated with proteinase K for either 1 hr at 56° C. or for 48 hours at 21° C. Incubation was performed in the presence of RNAse A, 100 mg/mL. An increase in both amount and purity of the DNA was observed with the extended incubation protocol (FIG. 8D).

The UCL home urine collection kit was compared with a commercially available kit (Norgen, Cat #18124, see the Norgen Biotek Corp. website on the world wide web). The standard UCL urine collection tubes contain 70 mg/ml of Stabilur.TM. urinary preservative. This study was performed on urine from healthy volunteers; half of each sample was treated with the UCL standard method and the other half with Norgen preservative.

Little difference was observed in integrity of DNA from urine preserved with the two methods. No difference in DNA purity or yield was observed between first void samples and samples voided at other times (for concentration vs. time $c^1_{(1)}$=0.255, p=0.614 and for purity vs. time $c^1_{(1)}$=1.046, p=0.306).

However, an apparent increase was noted in DNA yield over 8 days in urine treated with Norgen preservative, whereas DNA from urine treated with the UCL standard protocol was of similar amount irrespective of time.

An apparent increase in urine DNA yield with the Norgen system was found to be attributable to bacterial growth over time whereas growth was effectively inhibited using the UCL established protocol (FIG. 8E).

Figure 9:
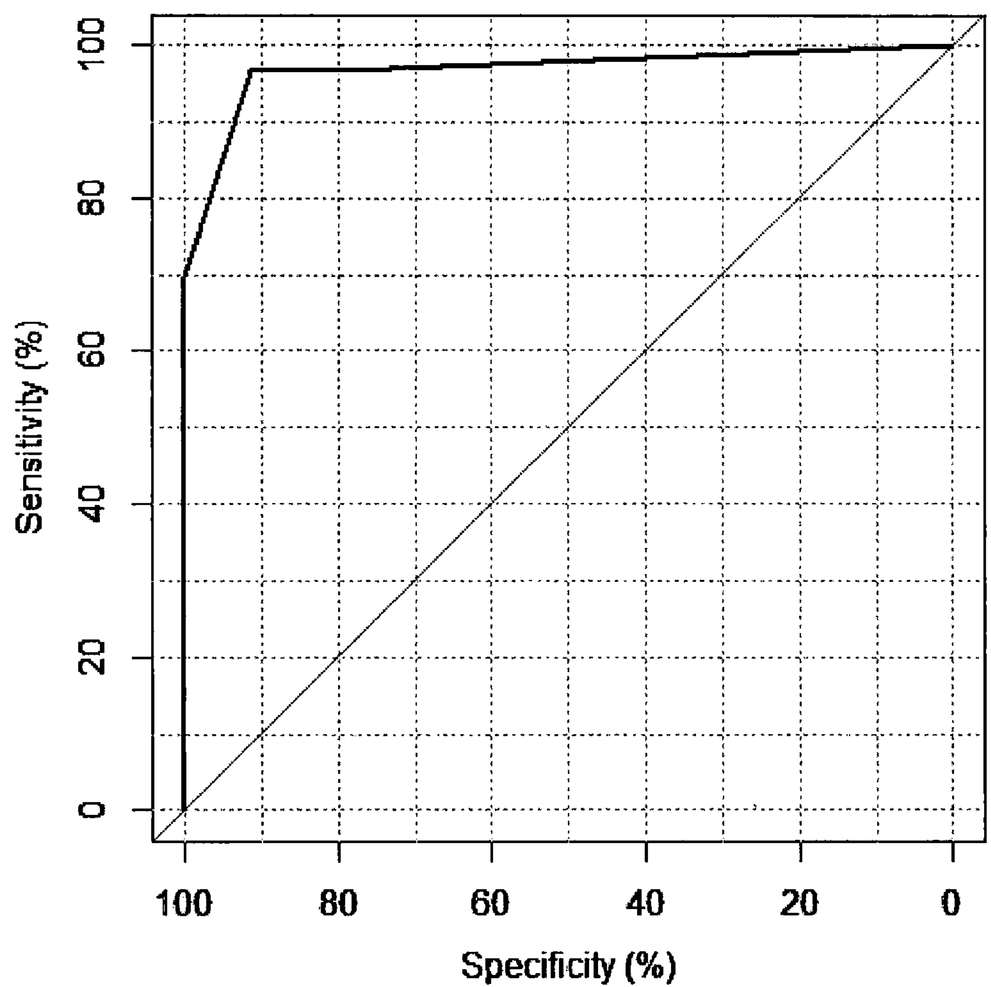
FIG. 9. ROC plot for UroMark model for the detection of bladder cancer from Validation Cohort 2-96 unique urine samples (64 non-cancer urines and 32 cancer urines).

Example 6: Additional Validation of Detection Panel Using High Throughput Technology 96 urine samples from 32 confirmed bladder cancer cases and 64 non-cancer cases (Validation Cohort 2) were analysed as described above. Sequencing of the 150 UroMark loci described above was performed following bisulphite conversion using the RainDance ThunderStorm® System. Statistical analysis was performed as described above, and the resulting ROC plot is shown in FIG. 9 (AUC=0.96, Sensitivity=0.97, Specificity=0.97, NVP=0.98).

Figure 10:
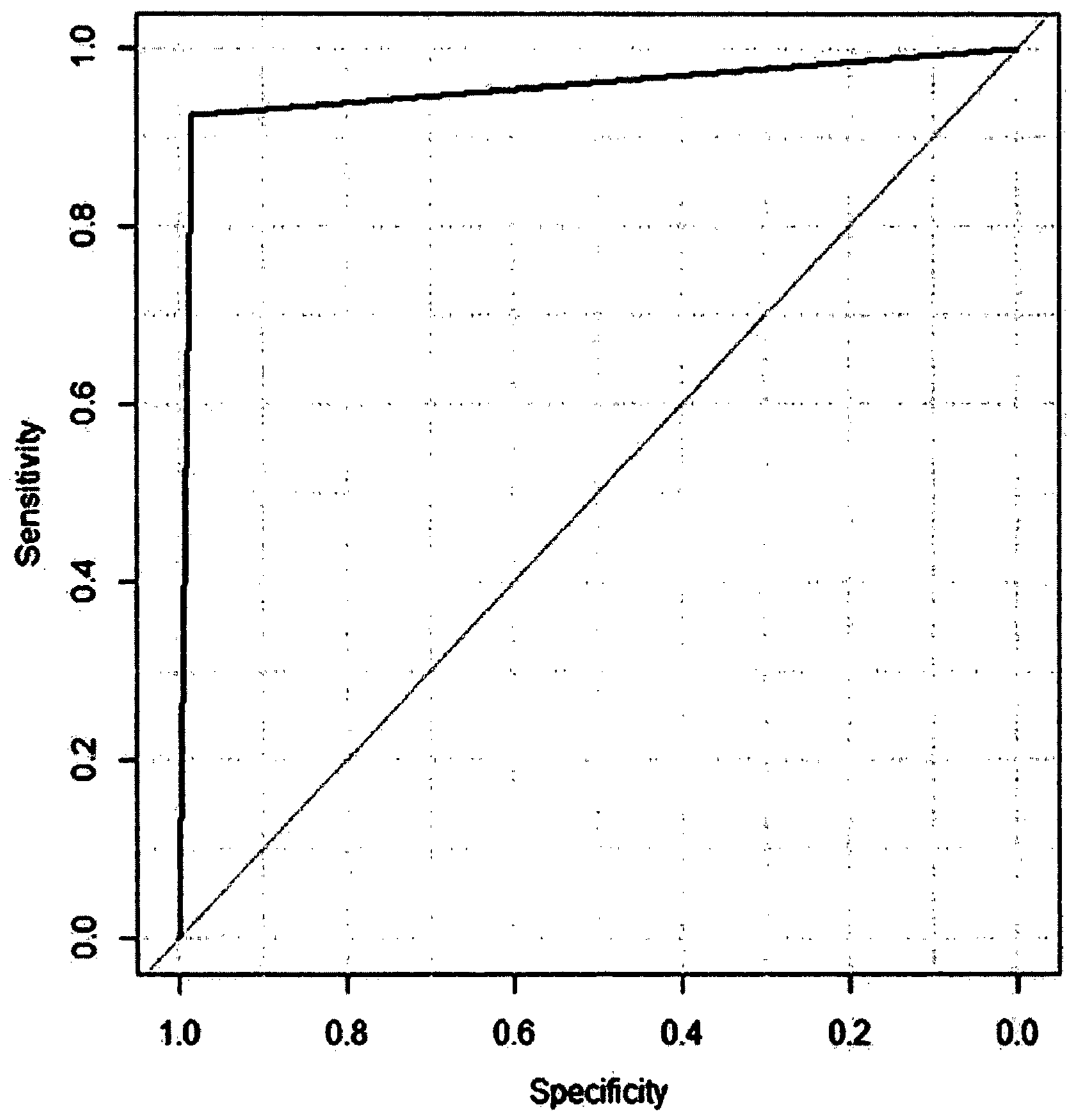
FIG. 10. ROC plot for UroMark model for the detection of bladder cancer from Validation Cohort 3-92 urine samples (65 non-cancer urines and 27 cancer urines).

In a yet further study, 92 urine samples from a cohort of haematuria and known cancer samples (Validation Cohort 2) were analysed as described above. This cohort consisted of 27 confirmed cancer cases and 65 non-cancer cases. Again, sequencing of the 150 UroMark loci described above was performed following bisulphite conversion using the RainDance ThunderStorm® System. Statistical analysis was performed as described above, and the resulting ROC plot is shown in FIG. 10 (AUC=0.955, Sensitivity=0.98, Specificity=0.97, NPV=0.97).

TABLE 1

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 1 | cg25622366 | 2 | 63281139 | OTX1 | TTGCGAAGGCCGAGATCTGGGCCTGCCAGGGGCCTGCCCGAGTCCTCTATCGCGGGTCCA[**CG**]<br>TGGCCACCAATGACCCGCGGCGCCCCCGCGTGTCCCCGCAGCCACTCCGCGGAAGCAGCG | 1 |
| 2 | cg20302133 | 1 | 111217194 | KCNA3 | CCTGCTCGCCCGEGGCCGGCAGTGAGGGCGGCAGCGGCTCGTAGCGGTCGCAGCCGCCGC[**CG**]<br>CCACAGCCGCCTTGAGGCGGGGCCCCTCCACCATCGGCCACCTCCGGCTCCAGCAGGTGG | 2 |
| 3 | cg13046832 | 14 | 29254680 | C14orf23 | CCGGGACCCCGTCCTTCTTTCCCCTTCAGTCTTCAGGGAGGGGGAGGCGCTCCGCATTAG[**CG**]<br>GGGCAGTTCAGCAACCCCGACCCCACCCGCGTGGCTCCAGGCCCAGGGGTCCGTTCACTT | 3 |
| 4 | cg17945976 | 2 | 66667433 | MEIS1 | GTGGAGAGCTCACTCTGCAGAATAAAATCAAGAACACCACGGTTGTAGCTGCTGTGGACT[**CG**]<br>GCGGTCTGAGCAGCCTCCCCGAGAGCCGTAGTTGCTAGTAGAAGTAAGATTGAGCTCTGG | 4 |
| 5 | cg21472506 | 2 | 63283967 | OTX1 | CTCCAAATCAAAACCACTAAGAGTTCCTCCCGCGCAGACTGCTGCCCCTTCAGCTGCCCT[**CG**]<br>ATTTTGCTCCACGCCTGCCGGCCAGAGCCTCCCGGCGTTTCTTCCGCCCCAGCGGAGTGC | 5 |
| 6 | cg26492446 | 20 | 61638574 | BHLHE23 | GGAGCGCTAGTACTTGCTTCTCGACTCCCCGGCCGCCGCCTCCGGCCGCCCCGGGGATTC[**CG**]<br>CCACCAAACGCACGCGTCCCAGGTGGGCACCCGCCTCGGTCCGTCTTTGAGTCTGACCCT | 6 |
| 7 | cg11142705 | 3 | 42306974 | CCK | GCCTCTCTTGACGCAGCTGTAAAATGCGGATGACACCATCTGGTTTTGCTCAGAGGAATC[**CG**]<br>GTTTGGGAAAGGGATGTGTTTTCTTCCCGGGCCAAGTTACCACCACCCGCGGCGCCCACT | 7 |
| 8 | cg26970841 | 16 | 85932666 | IRF8 | TGGCTGCCGGGGGCGGGAAAGTGATTTCTCGGAAAGCAGAGCACTTCGAAGAAGGCCGGC[**CG**]<br>CGCGAGCCAAGCTGACGCTATTGGTCGGTGTGGCCGTCGCTCTGCGCACCGCCCGTCCCC | 8 |
| 9 | cg23497016 | 2 | 66666684 | MEIS1 | GCAGTGGAGGGGACGAGGGCTTGTCGGGTGGGAAACTTAATTCAAAATGGCTGCTGGAAA[**CG**]<br>CTTGGGTTTTATTCGTAGCAAATGTTGCCAATTTCTCCGGCCAGATACGCTAAACCGATC | 9 |
| 10 | cg19178853 | 4 | 174450408 | NBLA00301;<br>HAND2 | GGCGGCGGCGGCAGCTGCGGCGGCGGCGGCGGCAAACGGGTAGCCCTCGTGGTGCACCAC[**CG**]<br>GGTGGTGGGGAAAACCACCTACCAGACTCATTTCGCCCTCCGCGCCCCTCCACGCGCCCC | 10 |
| 11 | cg14428146 | 8 | 23563925 | NKX2-6 | TCTCCAAGACTGCCTCACAGGGACCCCCAGGAGGCTCCGAACCATCCAGCTTTCTGTCAC[**CG**]<br>CCGCCGCCACCAGCGTTGTGAACCTCTGACCCTCGCGGCTCTGCGTCCATTCTCAGGTAC | 11 |
| 12 | cg16887264 | 4 | 147561775 | POU4F2 | TCCCACCGCGAGAAGCTCACCAAGCCTGAACTCTTCAATGGCGCGGAGAAGAAGCGCAAG[**CG**]<br>CACGTCCATCGCTGCGCCAGAGAAGCGCTCGCTCGAAGCCTACTTTGCCATTCAGCCTCG | 12 |
| 13 | cg06392169 | 6 | 391936 | IRF4 | CCAGAGGTTCGACCTCCAGGGCAGCGCAGGGTACCCCGGCTTCGGAGCGGGAAGGGAGCG[**CG**]<br>CCCCGTCCTGGAGCTCCGACTCCCACCCCATCTGCGCTGAGCCGGAGGCGCTGGTTTGGG | 13 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFG ENE_NAME | FORWARD SEQUENCE | SEQ ID NO. |
|---|---|---|---|---|---|---|
| 14 | cg11433622 | 2 | 66667549 | MEIS1 | CTCTGGGCTTGTTTTCAGCTTATTTAATTCACACTGAAATGTTTCTGCGCGGGACGAACT[**CG**]GTGTCACCGGGTCCCTCCCGGAGGGTTACTTCCTGCCCCCGACAGTGTAATGAGGCAAGA | 14 |
| 15 | cg01791874 | 5 | 16180055 | Mar-11 | CGGGGGTGACGGGGCGCGGGCGCGGGGTGGGCTGGGGGCGCGGATCAGTGGGACGGAGTT[**CG**]GGGTTCGGCTCCGAGCGGGCGGGCTGGAAGTGGGGGATCCCTCAGCCGCCTCCACGGGCC | 15 |
| 16 | cg23180938 | 5 | 115152485 | CDO1 | GGAGGACGAGGCGGAGAGCCACCCAAGAAAGGTGGCGGAGCCCGGGAGACCCTGCGCGCA[**CG**]GCTCACCCGCACATCCCCGGCTTCCCCGGGCTCCGCGCCTTCCCAAGAGCCCCGTTGTCT | 16 |
| 17 | cg26990102 | 2 | 119606746 | EN1 | ACTTGTCTCCGGATTCGTTTTGGAGGACCAGTATCCGACTATGCTGAAGCCTGCGGTGGC[**CG**]AGAAACGCCTCAGCAAACGACGCCTTCGGGGGTGTCATCTTACAGCTCCAGCGGACCTCC | 17 |
| 18 | cg11595545 | 1 | 111217497 | KCNA3; KCNA3 | GGGGAAGAGGCGGCAGCGGTGAGGCCAGGTCGCTCCTCCTCGCGCTCCCCGCCCTTTCGC[**CG**]CCTCCGCCCCCGAGCCGAGCCCACCGCCTGTTGCAGCCAAAGCCGCGATGCTCTGTCTGG | 18 |
| 19 | cg00986824 | 12 | 75601465 | KCNC2; KCNC2; KCNC2 | GTGCGGTAGTAATTGACCACATAGGCGAAGACGCCCGGGTGCCGGTCGAAGAAGAACTCG[**CG**]GCCGCCACCGGGATCGTCGCTGGCCCTGCCGCCGCGGGAACTGCAGTTGCCCGCGCCGCC | 19 |
| 20 | cg09462924 | 2 | 66666470 | MEIS1 | GGCTCTCCGAGGGCCTTGGGGTTGGGATCCCTAGGTGCAGCCCGTTGACAGTCGGCCCCA[**CG**]GCCATGGACGTCCTTTCCCCAAGTTAGCTGAGCGCCTGCCACCGAGATCCCCCGAGCCTG | 20 |
| 21 | cg07790615 | 1 | 237205174 | RYR2 | AGATTAGCCACCCCGTGCGCCCAGGTGAAAGATATCATTCTTCCGTGCGATCCGAAGTGC[**CG**]TGGAAGTTAGTGCCCTAGCCCAGTCCAGGAGGAAGGGCCGTCGTGCCGGCGGTTTTAAGC | 21 |
| 22 | cg06785999 | 14 | 60975964 | SIX6; SIX6 | GCCGACCCCGAACCCCAAGCCGCGGAGCCAGCACCTCCTCCAGTCGGGGTCGTCCGCTCC[**CG**]GCCGTTGAGCCACCGCCGCCACCCGGTAGTGTGTCCCGCTGCCCCAATCCGCCTCATCAA | 22 |
| 23 | cg04550737 | 1 | 119530600 | TBX15 | GAGACTGCGGCTCGCGGGTCTCTCCACCCTCCCCCCGCGTCCTCCTCCGCCCTCCTCTGC[**CG**]GATCCGACCTGCGCCCCTACGCTGCCCCAGCTGCTAGGAACTAGCGCCCCGAGCGCCGCC | 23 |
| 24 | cg19978181 | 5 | 76923988 | | TTACTTGGGAGGTCCCGGGTATCTGAAGCGGATCCCGGGTCTGGGGACATGAAGGGGCGC[**CG**]TGGCCTTAGGGAAGGCCCCAAAGAGGCCTAGGCCCCGGAGGAGGCAAGAGCCGCGGCCTA | 24 |
| 25 | cg23065934 | 5 | 16180266 | Mar-11 | GGGGAGACGCCGCGGCTCCAGAAACCGTTACTGGATCGGCCGGTGGGATGTGGCGCGGGC[**CG**]GGTGGGGCGCGACAGTCTGAGCCGAGACCCGCGTGGGCTTAAGGGTGCGCGAGGCGGGTG | 25 |
| 26 | cg14470895 | 5 | 115152431 | CDO1 | CGGGCCCCTTTTAAGCGCTTGGAGTCACTAGGAATGTACCAACGGCCCTCGGAGGGAGGA[**CG**]AGGCGGAGAGCCACCCAAGAAAGGTGGCGGAGGCGGGGAGACCCTGCGGGCACGGCTCAC | 26 |
| 27 | cg11036833 | 5 | 115152494 | CDO1 | GGCGGAGAGCCACCCAAGAAAGGTGGCGGAGGCGGGGAGACCCTGCGGGCACGGCTCACG[**CG**]CACATCCCCGGCTTCCCCGGGCTCCGCGCCTTCCCAAGAGCCCCGTTGTCTCCGGCGTCC | 27 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 28 | cg23727983 | 11 | 125774082 | DDX25; PUS3 | ACACGGGGCGTAAAGCGCGGCGGGGAGTCCGGGGGGCTCCCGCCTGGAGGGCTGTGTGAG[**CG**]GCGGGCCGCGGGGCGGCGCGGGGGGCGCTCTCCACTCTGCGGAAGCTGCCCCCTCTGCCC | 28 |
| 29 | cg16732616 | 1 | 50886782 | DMRTA2 | CGGCGCACACTGAACCGAAGACCTCGTAGGCGGGCCTCGGGGGGATGATGCCGTTGCCGG[**CG**]GCCAGCGCCAGCCCCTCCGCAGTGCCGTAGAGCAGCTCCAGCTCGCGCGCCTCGTTCTCC | 29 |
| 30 | cg16422098 | 10 | 15761881 | ITGA8 | CCCTGCGGGGCAAGGGGGGCTGGTGGAATCTGGCGGTCCCCAGCTCCCCGTGTCCCGGGT[**CG**]GTCCGCTCGGCGCACCCGTGGTCACAGTGCCCGGCGTCTGCTCCCACCCGCCCGCCCGCC | 30 |
| 31 | cg13620034 | 8 | 72755052 | MSC | AAAAAGAACGTGAGATATTAGAGAGAAACGATTGTCTCAAACCGAAACAGCTCTCCTACG[**CG**]AACCCCAGATATTCCTGACTTGGAGTAGCTAAGATTTTATCAGCATTCTGGGAATTTGCA | 31 |
| 32 | cg09424526 | 2 | 223163809 | PAX3; PAX3; PAX3; CCDC140; PAX3; PAX3; PAX3; PAX3; PAX3 | CTTTTACCCAAAGCTTGGTCAGGAGCCCTGAGCTGCGATTGGCCGACGGGTAGACCGTCC[**CG**]GGTGGCGGAGACACGCGCTGATTGGGCAACAGCGACCACTTTCTCTTCCCATCTCTGGTG | 32 |
| 33 | cg09813525 | 13 | 53420386 | PCDH8; PCDH8 | GGCGTGTCCCATTGCAGCACCGACCCGGACACCCCGAGCCGAGAGCCAGGCGGGCGGCAA[**CG**]CTCCGGGCTTCCTGCACTGGCAGGCGCAGCCGGCCCACGCCCGCCCCCTGCTGTTACCAC | 33 |
| 34 | cg18082337 | 3 | 147113726 | ZIC4; ZIC4; ZIC4 | GATTTTCTGATCTAGCAAAGACCTTCCCACACCCCGGGAAAGGACAAGGGAAGGGCTTCT[**CG**]CCCGTGTGCACGCGGATGTGATTTACAAGTTTGTATTTGGCTTTGAAGGGCTTTCCCTGG | 34 |
| 35 | cg27655158 | 4 | 1396593 | | GTGAAGTTCCGCAAAGTGCTTCGCAGCGGGCCGAGCCCGCGGGAGCCACCTGCCCGGCCC[**CG**]ACGCGCATGGTCATTTATAAATTTAAAACTCTTCCGTAGCAACCGGTTATGTACAGAGTC | 35 |
| 36 | cg26802289 | 7 | 20817859 | | GTGGCGCTCGCTGTCCGTGCAGCGGGCGGAGGCGGCCGCGGTGCCTTTGTGTGCGGTGGG[**CG**]CGGCGATGGGCTGCTCCGGCCCGCAGCCCGAGGGGAGCGGCGGGCCCGGGCCGGGGCCAG | 36 |
| 37 | cg18074954 | 18 | 44787492 | | CCTGTCCGCGCCGCCCGCGCGGTCTCCGGCCCCCTDCGCGAGGTCCTCCCTCCTGCCTCG[**CG**]CTCCACGGCTCCTCCGCGCTCTGCCTCCCGCGGCGCCTGCCGCCTCCCCTGCGCGGATCA | 37 |
| 38 | cg25947619 | 15 | 86233220 | AKAP13; AKAP13; AKAP13 | TTACGATTTCACTAATCGCAGCTCAAAGCTGCTGAGCTCTGCCCTGACGGCATGCGCCCC[**CG**]CTTCTGTGAGAGCACGCTTCCTGGCATGGGGGTCGAATCATGTCCATAAAATGGGCTCGG | 38 |
| 39 | cg15384598 | 14 | 24045549 | JPH4; JPH4 | TGCCTCCCTCGTCGCCCGGCAAGGGCAGGGGCGGGGGTGGCGTCGGGGGGTCGCTGTGGC[**CG**]GAATCCAGGGAGGTGCGGCGGGGCGAGCGCAGCAGCGCCGCCTGATGGTAGGGCACACTC | 39 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFG ENE_NAME | FORWARD SEQUENCE | SEQ ID NO. |
|---|---|---|---|---|---|---|
| 40 | cg16178603 | 2 | 66667101 | MEIS1 | CGAGCCGGGGGTGGCGGGCGGGGACGTCTGCTCGTCAGAGTCATTCAATGAAGATATAGC[**CG**]TGTTCGCCAAACAGGTCAGCAAAATAGATGTTAAAAAGTAAAAGAAACAAAAAGAGAGCC | 40 |
| 41 | cg23241781 | 14 | 70653964 | SLC8A3; SLC8A3; SLC8A3; SLC8A3 | TTTAATTCTTCTGCCCGGGAGACCTAACCGCCGAATGCGTTCGGAGGTATGTTTTTTAAT[**CG**]CCAGGAAAGGGGGAGAGAGAGAGAAAGAGAGAGAGAGAGAGAGGAAAGGAGGAGAGAA | 41 |
| 42 | cg01419831 | 2 | 162283705 | | AGGAGGAGCACGTGCGGTCGGTGGGGCGCAGGGCCGGGGAGCCAGGGGGGTGCCGGGGCT[**CG**]AGGCCGCGGGGCCGCGGGGGCCGCGCTCTGCTCTCCGCCCAGGCTGGGCCACTGGAGCGC | 42 |
| 43 | cg17039236 | 18 | 77548049 | | AGGCGAAGGCCGCCCCGGGAGAGCGGGGTCCCGGGAGAGCGGGGTCCCGGCTGTGGGGGA[**CG**]CGGGCCGAGGCTGTCGCGAAGCCGCTGACGGCCGAGGCGCTCCCGGTTTTCGCGGCGCAC | 43 |
| 44 | cg21901718 | 5 | 16180076 | Mar-11 | GCGGGGTGGGCTGGGGGCGCGGATCAGTGGGACGGAGTTCGGGGTTCGGCTCCGAGCGGG[**CG**]GGCTGGAAGTGGGGGATCCCTCAGCCGCCTCCACGGGCCGGCCCCGCGCTCACGTCGGTT | 44 |
| 45 | cg25191628 | 1 | 50886949 | DMRTA2 | CGCTGGCGCTCCGCGATGAGCGTGCACTTGGCGCACAGGCAGTCCTTCCAGCGACAGTAG[**CG**]TTTGTGGCCCTTGAGGGCCGACACCACGCCATGGTTGCGACAGCGCGCGCACTTGGGGGT | 45 |
| 46 | cg27277463 | 12 | 62585031 | FAM19A2 | CCGCGGTCCTGCAGTTGCCGCTCCGGTCCCCAGCGCTGGCCGGCGACCCGAGGCGCGGCT[**CG**]CACCTACCTGCAGCCCCGCTTCCCGGTGGCGGCAACACCTAGCGATGCTCCTGCAGCTTT | 46 |
| 47 | cg05311410 | 7 | 27225523 | HOXA11AS; HOXA11 | CTGGTGGCTTGTCCGATTTGCACGGTGACTTGATTACACTCTCTCATTCATGGTCACTTC[**CG**]AAGCGCTTTAGTGCCTTCCGTCCCTAAACCGCCAACAGCCAGAACGGCTTCTCCCCGCGG | 47 |
| 48 | cg23229261 | 2 | 63284066 | OTX1 | TTTCTTCCGCCCCAGCGGAGTGCGCTGGGGCGCGCCAGGGCTAGGCCCGCCGGAGGAGCG[**CG**]TCCCCAGCCTTCCGCGCACAGAGCCGCATCCCGCCCCGCCCTGCGCTGGACTGGTTCAAG | 48 |
| 49 | cg10397440 | 8 | 57359258 | PENK; PENK; PENK | CCCGGGGCTTAACGGCTGCTGGAGCCACTTTATAATTAGCCCCAAACCGAAGGAGGCGCG[**CG**]CGCCCCAATCGCCGGCGGGCTGCAGCTGACGCAGGCCCTACGCCAGCCCCGCGCCGACGC | 49 |
| 50 | c018326021 | 10 | 106401479 | SORCS3 | GGCGAGCGGCGGGGCCGGGGCATCCCAGCTCCTGCCAAGCTTGGCGGCGCGAGGAGGAGT[**CG**]CCGGGCGCAGCCCCCAATCACCCAGGAACGCGGGGACGCCTGGGCCACTGCTCCGGCCGA | 50 |
| 51 | cg06533244 | 6 | 27258460 | | CACAGGTTTCCGTGGTGTAGTGGTTATCACATTCGCCTTACACGCGAAAGGTCCTCGGGT[**CG**]AAACCGAGCGGAAACAACTTGCAATTTTTCGGGGTGTTTCTGTTTTCCAAGATTCCCTTA | 51 |
| 52 | c003078363 | 12 | 54408664 | | GTAAAAACCCGTTTTATGGGGGAACGTAATTGTGAGCGGGATGCGCTCTCTTTAGAATCG[**CG**]TCCTCCCAAATGCTCCCGCCGTCCCATTACCGGAATGGGGACCATTCGGCTGCTGCAGAT | 52 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFG ENE_NAME | FORWARD SEQUENCE | SEQ ID NO. |
|---|---|---|---|---|---|---|
| 53 | c001796166 | 14 | 95239586 | | GGCCCCGCATCGCCTGGCGCAATTGGAATAACAAATGCGACGCACGCAAATTGTCCACCT[**CG**] TGTTGCTAAGCGATTGTTTGTCGGCCCCGCACGCACAGCTCAGCATGGGAGGACCGCGAG | 53 |
| 54 | cg00339556 | 5 | 16180048 | Mar-11 | GGCGCGGCGGGGGTGACGGGGCGCGGGCGCGGGGTGGGCTGGGGGCGCGGATCAGTGGGA[**CG**] GAGTTCGGGGTTCGGCTCCGAGCGGGCGGGCTGGAAGTGGGGGATCCCTCAGCCGCCTCC | 54 |
| 55 | cg03978375 | 16 | 85932668 | IRF8 | GCTGCCGGGGGCGGGAAAGTGATTTCTCGGAAAGCAGAGCACTTCGAAGAAGGCGGGCCG[**CG**] CGAGCCAAGCTGACGCTATTGGTCGGTGTGGCCGTCGCTCTGCGCACCGCCCGTCCCCCC | 55 |
| 56 | cg26013553 | 1 | 111217406 | KCNA3 | CTGCTCGCTGGGCGCTGAGGAGGGTGGGCGCGGTGGCGGGCTGAGGGCGGCGGCGGCGAG[**CG**] CAGAAGGCTGAGGCGCTCGTCCATGCGGCGGGGAAGAGGCGGCAGCGGTGAGGCCAGGTC | 56 |
| 57 | cg09734791 | 8 | 72756155 | MSC | ACTGCTTGCACTCTGCGGCTGAGCCCTTGGCCGGGAGGGGCTTCTTGCCACCACCGCCCG[**CG**] CTACCACCTGCGCCGCCGCCCCCAGCCACACGGGGCCGCTTCCTCTTGCAGCCTTCCGCG | 57 |
| 58 | cg12040830 | 11 | 112833773 | NCAM1; NCAM1; NCAM1 | GGCGGGCCAGGGAGCACCCAGTGCGCCCCCTCCGCGGGCGGCACAAGAGCAGCGCTCGGC[**CG**] CGCCTCCAGCCAACTCGGGTCCCTCCCACGGCGACCAATCAGTGCGAAGCTGGCTGGGC | 58 |
| 59 | cg18617005 | 5 | 140787504 | PCDHGA4; PCDHGA6; PCDHGA9; PCDHGA1; PCDHG58; PCDHGA5; PCDHGB1; PCDHGB6; PCDHGB4; PCDRGA3; PCDHGA2; PCDHGA7; PCDHG82; PCDHGB6; PCDHGB5; PCDHGB3 | ATTTCGGAGACCGAATTCAAAATGAAAAACCGGGCTGCTGTCCCGCACGGAGCCTCTGGG[**CG**] CCGCTGTCGGCCAGTGCAGAGCAAGCGCTGACGCCGGGGATCCGTCAGCCTCTGGCCTGG | 59 |
| 60 | cg19597382 | 4 | 147559423 | POU4F2 | ACCTCCGCTCGTATTGGGCTGGGAGTTCAGAGCCGCGCGCAGAACCCGGGTTGGCCGCAA[**CG**] TCTGTGTTCTCAGCGGTGGCCGGGAACCTGGGATCAGGGTCACCTGAGCTGACGGGGTGG | 60 |
| 61 | cg05134015 | 14 | 36973365 | SFTA3 | CCGGAGGTTCGATGGCCGCCGGGCCAGTGCGGGCTCAGAGGAAGACCCTGCAAAAAAGAG[**CG**] CTCGCCCCCACCCCTGGAGCCGACCCTGCGCAGTAGGGCCGCAGCCGGTCCCCGCGGGCA | 61 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 62 | cg02700891 | 3 | 129693586 | TRH, TRH | GGCGCAGATATAAGCGGCGGCCCATCTGAAGAGGGCTCGGCAGGCGCCCGGGGTCCTCAG[**CG**] CTGCAGACTCCTGACCTGCCGACTGCGGATCCCGAGTCCCCGGATCCCGGACCCATCCTG | 62 |
| 63 | cg13476854 | 1 | 119549263 | | GTCGGATCTCTAAATTATCTAATCTGGCGGCTGCGTACGACTCAGGGAAAGCCCTGGCCG[**CG**] AGCTTTTTCACCAGGCTTGAGCTCAGCAGCCGGGCCCGCAGTGTTGCCGCCAGTGGGGAG | 63 |
| 64 | cg00017221 | 1 | 149719536 | | GTCTCTCCACCCGCTGCCGCCTAGCAAAGGCGCATCTTTAGGTCGGTAGTGAGGTGCCGC[**CG**] GGACGCTGCAACTCGCTCCGGGACTTGTAAACCTGGCAGGTGTTCGAAGAGGGCCACTGG | 64 |
| 65 | cg05310764 | 6 | 27513479 | | CACTCAACCATTATAAGTTCACCCCAGCCGTCAGCGATGGCGTAGGTAGGTAGTCGTGGC[**CG**] AGTGGTTAAGGCGATGGACTTGAAATCCATTGGGGTTTCCCCGCGCAGGTTCGAATCCTG | 65 |
| 66 | cg04495995 | 7 | 19147157 | | GTGTAGAGAACAACAGTCGCTCCTTAGATATTACTCCAGGACGGAAACCTGATTGCAAAC[**CG**] CTGTTCCTTCGAAACTTGCAAAACCCGGAACAGAAAACTCCCGCCCAGCCAATTTTAGCT | 66 |
| 67 | cg01642521 | 11 | 20618250 | | ATTCAGACCGAATGGCTGCGCGGTGATGGATGCGGATTTACGGCCTCCTTGGCTGCGGCG[**CG**] CTGGGCCTGATTATCACTATAAACAGGCGTCCGCGGAGGGCGGGGGCGGAGGCCCGCGTC | 67 |
| 68 | cg24504927 | 12 | 85667353 | | TTAACCACAGAGTTGTTCTTGATTGTAAGGGACTTCGCCCACTTGGTTGAAGTGGAGAGC[**CG**] GTCCTCATTCCAGACGTCCCGCACGGCAGTCGCTCATGGCTCCCTCCAGGCCGGGAGCCA | 68 |
| 69 | cg03276408 | 13 | 112712475 | | GCAGGGACCCGGCTGGCCGCCTCCCCTTGCAGGAAACAGGTGTTTGAACGCGATAGCGGC[**CG**] CCAGTCAACTAAGGCATTAAAAGCTCGCTTTATAACATCGATTTCCTGGAGTGCGGTGGG | 69 |
| 70 | cg27501878 | 20 | 61638588 | BHLHE23 | TGCTTCTCGACTCCCCGGCCGCCGCCTCCGGCCGCCCCGGGGATTCCGCCACCAAACGCA[**CG**] CGTCCCAGGTGGGCACCCGCCTCGGTCCGTCTTTGAGTCTGACCCTAGCGCAAGAGTCCC | 70 |
| 71 | cg07495363 | 2 | 198651076 | BOLL; BOLL | GGACTCCGAGCCGGGGCGTCTCAGGGGCAGAGCGCACGGCACAGCGGGGCGGGCGTGGGG[**CG**] TGCGGAGCGAGGGCTCGGTTCTGGGACCCCTCTCGCCTTCTCTCAGACGGCTGGGGAGGA | 71 |
| 72 | cg06750832 | 1 | 111217691 | KCNA3 | CTGCGGGGCGCGCGCCCGCCTCCGCGTCCCCTTAGGATTCCCGCCCACCGCGCGGGCGCG[**CG**] TCCCGCTCTCGGGGGCAGCCGCCGGGCCTGCATTTCTTGCAGCCCTCAAGGCCCCTCGGT | 72 |
| 73 | cg22474464 | 20 | 21492914 | NKX2-2 | GGAACCAGATCTTGACCTGCGTGGGCGTGAGGCGGATGAGGCTGGCCAGGTGTTCGCGCT[**CG**] GGCGCCGACAGGTACCGCTGCTGCCGAAAGCGCCGCTCCAGCTCGTAGGTCTGCGCCTTG | 73 |
| 74 | cg20146541 | 1 | 248020697 | TRIM58 | ACTGCGGCCACAGCTTCTGCCTCAGGTGCATCTCCGAGTTCTGCGAGAAGTCGGACGGCG[**CG**] CAGGGCGGCGTCTACGCCTGTCCGCAGTGCCGGGGCCCCTTCCGGCCCTCGGGCTTTCGC | 74 |
| 75 | cg02864844 | 7 | 149917263 | | GGATGCAGACGCACCAGCGGCTGCTCACACTCCCTCCACAAACCTGCCGGAGTCTCCACT[**CG**] CCCGCCAACTGTAGCCTCCATCTGCGCCCCACGCCCCCGCACAAGCCCCCTCCGTCGCGG | 75 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 76 | cg12323723 | X | 136656581 | | GGCGCAAAAGGGGCCGCCCCCGTGCCGGGAACAGACTTTGAAGTGGGTTTTTAGCGCGCA[**CG**]TGTGAGAGCCGGGCCAGGGCCGGAGCGGGGACCCGCTGGGAGGAAAGAGGAGGCTCCGGC | 76 |
| 77 | cg14996220 | 12 | 85673270 | ALX1 | CTCCCACCCATCGCCACCGCGTCCACACTCCGCCGCATTCCAGAGAAAAAGAAAAGGCCA[**CG**]GCCTCGTAAAGCTCCCAGCTGGCCCGGACCCCGAGCTCCTCCCGGTTAGAAGCCGAAGCG | 77 |
| 78 | cg23151000 | 2 | 38302892 | CYP1B1 | GATTTCCTTTAAAGTACCTACCAGGCCACCCGCTACCTGTAATAATCCATCTGAAGAGGT[**CG**]CCGGGGAGCGCCTCGGCAGACAGACTGACCTGCGGGGAGGTGCGGTTTCCAGTGGCGCGG | 78 |
| 79 | cg00963169 | 1 | 50513927 | ELAVL4 | CGGCGCAGGCCCCGCACCCCCGACTCTGCCCGCCCTCTGTTACGGACACCCGCTGGGCCA[**CG**]TGGTCGCGACTGGCTTCTCCCAGCGGCCAGCCTGGCCACCCCGACTCCCAGGGAGGGGGA | 79 |
| 80 | cg13320291 | 10 | 118030970 | GFRA1; GFRA1; GFRA1 | TCGGCCCTCCGCCCCGGGGCATCCTGGCCTGAGCAACGACCCGGGCTCCCGGGCCACCCC[**CG**]GCTCCAGCCACCCGCTCCGCCCGGCTGAAACTCAGGCGCTTTCCGAGGAGAAGTGCGGCG | 80 |
| 81 | cg13352750 | 7 | 27225123 | HOXA11AS; HOXA11 | TTCTCACCGAAAGCACGTAATCGCCGGTGTAACTCATGTTGGCTGGGGGGCCTCCCGGCG[**CG**]CGCGGAGAGGCTGGGGTGCGCCCCCATGCAGCATGCTTGTGCTCAATTGCAGGGTCCTCG | 81 |
| 82 | cg26521404 | 7 | 27204981 | HOXA9 | GCTGAAGTCGGGGTGCTCGGCCAGCGTCGCCGCCTGCCGGGGAGGCTGGCCCAGGGTCCC[**CG**]GCGCATAGCGGCCAACGCTCAGCTCATCCGCGGCGTCGGCGCCCAGCAGGAACGAGTCCA | 82 |
| 83 | cg07573209 | 15 | 76630095 | ISL2 | GGGTTGGGTTGGGGCTGGAGTAGCCGAGGCCGGCCTGGGTCCGGGCAGTCAGGCCTGACG[**CG**]GCCCCGCGCCCTTCCCCGGCAGAGAAGCCCGGGACGGCCATGTGCGTGGGCTGCGGGAGT | 83 |
| 84 | cg10835584 | 18 | 55108852 | ONECUT2 | GCGCTTCCGGCGATCCGCCTGGGCGGCTGGGTCCGCGAAGCCAATGCGCTGAACGGTGCC[**CG**]AGTCTTCCTAACTATCCTGTGCTTGGCCGTTGCCACTGGGCCCTGGTGACTAAGCCCAAG | 84 |
| 85 | cg09474331 | 19 | 54926805 | TTYH1; TTYH1 | TACCGGCCCTCAGCTTGGGTGCATCTCCTCCACCAGCTGCCCCGCGCCGACTTCCAGCTC[**CG**]CCCGGTGCCCAGCGTTTTCGCGCCCCAAGAGCAGGAATACCAGCAGGTGGGACCGGGCGC | 85 |
| 86 | cg20870512 | 7 | 1272515 | UNCX | GTCCCAAATTCCCCGGGCCGCGGCTAATTATCGGGAGCTTGATGTTGATAAGTAAAGCGC[**CG**]GAGTGCGGGCGAAGCATGTGTGGGGCTCCGGGTCCCTGTCTCCGCCGCCGCCGCCCGCGC | 86 |
| 87 | cg21678445 | 18 | 22930283 | ZNF521 | GAGGGGCGGTCAACTTCTGGGAATGGCCAAGAGGGGTGCTCTGAGGCCCGAGCCGGGGTC[**CG**]GTGCCCGCGGCCGGCGGCCGGGGTCTGTTTACTCCGGCGACGTGCGGAGAGGACCCAAGC | 87 |
| 88 | cg05560435 | 5 | 172671526 | | CGCCGCCTTTCCCTCCTCGCCTCTTCCTTCCTTCCGGGTCGTGCCCTCCAACCTGCTGTG[**CG**]TTACCGCAGCCAAGTTTCCACCGCCCGGCGGAGCGCATTGTGAACAGCAGCTGACAAATT | 88 |
| 89 | cg08382226 | 6 | 108440339 | | CCGACTCGGGATGACAATTGACGGGGATCAAGGGATTGCCCATTCTGTGCCTGTAAGAAC[**CG**]ATTCGTGCCAGAGAAACTCATCAAGTGGAGGCGGAGAATAAAGACCGTTCGGGGGTAAAT | 89 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 90 | cg25510609 | 15 | 86233236 | AKAP13; AKAP13; AKAP13 | GGCAGCTCAAAGCTGCTGAGCTCTGCCCTGACGGCATGCGCCCCCGCTTCTGTGAGAGCA[**CG**]CTTCCTGGCATGGGGGTCGAATCATGTCGATAAAATGGGCTCGGTTTCATGAAGTACCCC | 90 |
| 91 | cg19650157 | 13 | 78493297 | EDNRB; EDNRB; EDNRB | GAAAGCCGCTACTCCCTGGCTGGCTGAGCTACAGCTCCCGCAGCGCGCCCAGGAGTGCGC[**CG**]GAGATTCGGAAACCCGCAGAGACTTCTCAAGTCAGCAGGAACTTGGAAACCGCTGTTCCC | 91 |
| 92 | cg01283246 | 5 | 135266135 | FBXL21; FBXL21 | CTCGCTCGGGCGTGTTCCTGCGCCGACCGGACGGCCGGACTCCAGCACCTTGGCCCGGCC[**CG**]CGAACGCTGAGCACGCGCGGAAACCCTTTAAAGGTAGCACATTTTTCGGGTGTCGCGGGG | 92 |
| 93 | cg20872937 | 18 | 74961968 | GALR1 | CTGGAAAAGCCGGGAGGGAGTCGGAGGCGCCAGCCCACTGGGGAGGTGGCGCTGGGCGCG[**CG**]GGATGCGCGGGGAGCCTTCTCTGCAGGAGCCGCACAGTGCACTGCTGCGCGCTGGGCAGT | 93 |
| 94 | cg03698009 | 7 | 27204349 | HOXA9 | TCTCCCGTAGCCCTGCGGGCCGCTCTTCACTGCTCTCCAGACTTGGGGCCCTATCTGAGG[**CG**]TCCCAAACACCAACTTCTGGCTCCTGGCCCCAACTCGAGAGGCTTCCAGCGAGGACGAAG | 94 |
| 95 | cg01423964 | 1 | 111217575 | KCNA3; KCNA3 | GAGCCCACCGCCTGTTGCAGCCAAAGCCGCGATGCTCTGTCTGGGTCTGGCGCGGTCAGG[**CG**]GGCTCCCGCACGGGGACGCCTCCTCCCTCCTTCTCGCGCTCTCCGCCCCCTCCCCTGCGG | 95 |
| 96 | cg19923650 | 5 | 172659730 | NKX2-5; NKX2-5; NKX2-5 | CGAAGTTGTTGTTGGCGGCGGCAGTGGCCGGCTGCGCTGGGGAAGGCCCGGCGGGGTAAG[**CG**]GCAGTGCAGCTGTAGCCAGGGCTGCAGGCCGCGCCGCCGTAACCCGGATAGGCGGGGTAG | 96 |
| 97 | cg13324546 | 8 | 23564031 | NKX2-6 | GTCCATTGTCAGGTACTGAAAGTTTTCGGGGCTGTTGGGCAGGCGCGGATGTGGCGAAGC[**CG**]CGGGGCAGGTCCGGTCGGGCTGGAGTCGCAGGATGTCGTTGACCGAGAAGGGGGTGGAGG | 97 |
| 98 | cg27357571 | 21 | 34398226 | OLIG2 | CGCCCCCGCCCCCGCCACCGCTGCCGCCGTCGCCGCTGCCACCGGGCTATAAAAACCGGC[**CG**]AGCCCCTAAAGGTGCGGATGCTTATTATAGATCGACGCGACACCAGCGCCCGGTGCCAGG | 98 |
| 99 | cg08448701 | 20 | 21686282 | PAX1 | CAGTGACGGGAACCAATGAGCTGCCAACTCGCGCGTCTCCGGCGTGACTGCCGAGATTGA[**CG**]TGGAGGACACGTCAAATTGATTCCCGCACGCTGCAGCCTCCCGGTCAGACGAATTTCTCC | 99 |
| 100 | cg16002355 | 4 | 111544387 | PITX2 ;PITX2; PITX2 | CTCCGCCTCCTCCCAGACCCTTCTCCGGGTGCGACTGACGTGGCTCCGCACCAATCAGGA[**CG**]CCCGAGCCGCGGTGGAGGGACTGTCCTGCCTGCACCTATCAGCAGTGCGGGGCCGGGCT | 100 |
| 101 | cg05302386 | 14 | 52734525 | PTGDR; PTGDR | TTAGCACCCGGGCGCCGGGGCCCTCGCCCTTCCGCAGCCTTCACTCCAGCCCTCTGCTCC[**CG**]CACGCCATGAAGTCGCCGTTCTACCGCTGCCAGAACACCACCTCTGTGGAAAAAGGCAAC | 101 |
| 102 | cg17964510 | 2 | 175199694 | SP9 | AGGCGCAGCCAGCGGCACTTCAAAGCGGGTGCTCCTCGCACTTAGGCTGAGTTTAGCCGG[**CG**]GGAGCCTGGAGTCCGCTCGGCACGAGCGCGGGGACGCGGGAGCCGCGCGGGACCCAAGCA | 102 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 103 | cg24031355 | 10 | 22634439 | SPAG6; SPAG5; SPAG6; SPAG6 | GGCCGCGTTCCGGTTCCGGTAGGTTGCCCGGGAGACGCGGGTACACAGAGAAGCGGCTCC[**CG**]TCGGAGGCCGAGTCGTCGCCACGATCGCCCCCTTGGTGGACTCGCAGGCCGAGCGGCTTC | 103 |
| 104 | cg24961583 | 3 | 27765409 | | GGGAGCGCATTTTCCGGCTGAGATGTCGGGACTCTGCTTCCCCAACCGAACGCGATCACA[**CG**]GGAAACTCTTCGCCCACAACAGATGAGATGGCCAAAGGATTGCTGAGTGCGCACACGCAA | 104 |
| 105 | cg02167020 | 10 | 102899949 | | GGACTCATGCAGAAGAGGACATTCCGCAGGTAGGTACAATCCCAGCGCTGGGGCCTGGGG[**CG**]TCCGGGGGGCGGCCTTTGAGCTTCCCGGATACCGCTCGCCTGCTCCCGGAGCTGTTCGGC | 105 |
| 106 | cg25026529 | 1 | 91183051 | BARHL2 | GGGGGAGTTAAAAAAATTTCTGAGAAAACTCGGAACTTGCGCTCCAGGAACGACTGCGCA[**CG**]TGGCGCGGCGGTGGCGGCGCGGAGGACCCAGGCGAAGGCGAAGGCGAAGGCGAAGGCGCA | 106 |
| 107 | cg05783139 | 2 | 198650985 | BOLL; BOLL | GACTGCGTCGCCTCGGGTGGCAGGTGGCGGTGCGGGCGGGCGCTGCAAGCCGGAGAGGGG[**CG**]CGGGAGGGCGAGTTTCGGCTGTGGCCCTGGGACTCCGAGCCGGGGCGTCTCAGGGGCAGA | 107 |
| 108 | cg25691167 | 7 | 19184961 | FERD3L | GAGGGCGTCTCGGGGAGGCCAGGGACAGGTCTGCGACGAAGTCCAGCACCGTAGTGTCCA[**CG**]CAGCTCTCCGGATAGGCCGCCATCGCTTCGGCTTGGCCCTGCCTCTCATCGGTTTTCCGC | 108 |
| 109 | cg25951981 | 4 | 46995743 | GABRA4 | GTATACCGCTCCACACCCTTTCGTGCCCGCGCGCTGAAGGTTCTGGGGTTCGTATCCGCG[**CG**]CTTGCGCTGCAAGACTCGGCAAGTTTGTTCCGACTGTAACTCCGGGGATGAGGAACGGGG | 109 |
| 110 | cg11601252 | 15 | 68122139 | LBXCOR1 | CACAGAGGAGGGGTTGGGGGCAGCGGAAAATCGGGCAGGTCGAGGCAGCCGAACCCCGGA[**CG**]ATGTCCCCCCACCCACCCCGAAGGTCGCAGCCTGGGCCGCGTTCTCAGCAGGAGTCGGGC | 110 |
| 111 | cg10698928 | 8 | 65290320 | MIR124-2 | CAGAAGGACCATCTGCGGACTCGTTTTCACTGCTCCAGCTCCCGAAATCGTTTCTCTGGA[**CG**]CGGCAGTATCCGCAGCGCATGCACCCTCCTCTGGACTTCCGCAGCCCAGACCTGCGCTTA | 111 |
| 112 | cg25832771 | 8 | 72756058 | MSC | GGGGGCACCCAGGGCAGGCTGGTCTTGAGCCTGGAGAAGGCTTTGCTCAGCACGCGCATC[**CG**]GGCACGCTCACGGGCGTTGGCCGCGTTCCGCTGCGACTGCTTGCACTCTGCGGCTGAGCC | 112 |
| 113 | cg18507379 | 5 | 140787507 | PCDHGA4, PCDHGA6; PCDHGA9; PCDHGA1; PCDHGA8; PCDHGA5; PCDHGB1; PCDHGB6; PCDHGB4; PCDHGA3; PCDHGA2; | TCGGAGACCGAATTCAAAATGAAAAACCGGGCTGCTGTCCCGCACGGAGCCTCTGGGCGC[**CG**]CTGTCGGCCAGTGCAGAGCAAGCGCTGACGCCGGGGATCCGTCAGCCTCTGGCCTGGGAT | 113 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| | | | | PCDHGA7; PCDHGB2; PCDHGB6; PCDHGB5; PCDHGB3 | | |
| 114 | cg14733048 | 8 | 109095782 | RSPO2; RSPO2 | CTTTCTCCACGGTCACTTCACAGCTAAGATTTCTTTCTTTCCGAGCTGTAGAAGGCAGAA[**CG**]CTCTCGGGAGGACGAAGTGATCCGAAGGGATGTGGCAAGCGCACTTTCCGATGGAGATGC | 114 |
| 115 | cg09735723 | 10 | 106402042 | SORCS3 | GGGAGGGATCTGTGCTCACTTTCTCCAATACTTGGCTTGGAGGGTCAGTTTTCCTGTTTG[**CG**]GGGTGCTTGAATTCTTGGATGAGAAAAAGGGCTGACTTGGGGCGGGAGCCGCTGAACAGA | 115 |
| 116 | cg05099508 | 10 | 22634432 | SPAG6; SPAG5; SPAG6; SPAG6 | GCAAGACGGCCGCGTTCCGGTTCCGGTAGGTTGCCCGGGAGACGCGGGTACACAGAGAAG[**CG**]GCTCCCGTCGGAGGCCGAGTCGTCGCCACGATCGCCCCCTTGGTGGACTCGCAGGCCGAG | 116 |
| 117 | cg14638883 | 6 | 166582201 | T | TCTGAGAAGTGTCCTCCTCGCTCTCTTATAAAAACAGGACTTGTTGCCGAGGTCAGCGCG[**CG**]CATCGAGTGTGCCAGGCGTGTGCGTGGTTTCTGCTGTGTCATTGCTTTCACGGAAGGTGG | 117 |
| 118 | cg26673012 | 7 | 35293753 | TBX20; TBX20 | GGAACTACGGACAGTGAGCCCTGGCGCTCGCTGCCCTGCGCCTTAATTTGCTGGCGGCGG[**CG**]ATCCCGGAGGCCCGCAGCCAGTCAGCGCCGTCTCACGTCACCGCTTCCTGATTCCGCCGC | 118 |
| 119 | cg14763548 | 20 | 25052447 | VSX1; VSX1 | GCTCGGGGCCCCTGGGCGGCAGGAACGGCACGTCCGCTAGGAGCAGGCAGGGTGCTCGAG[**CG**]GCCGCCGGCGGCTGCGTGCCGAAGCCACAGAGGAGGCCGAGTCCCAGCGGTAGGGCCCCA | 119 |
| 120 | cg22884656 | 2 | 45157296 | | AATCACTGTAGTTAAAAATGTATGGGATTTTTGCCGTCGGAGCACCTCGTATCCGGCGCG[**CG**]GGCCCAGTGTGGGACTGCGGCTGGGAGCCCGGGCCCTCCGGGAGTGAAGATACCTTTGGA | 120 |
| 121 | cg21401879 | 2 | 45162036 | | GCGGGCTCCCCCTGGCCACATCCCGGGCCTCTCACACAAGAAGAATAGTTCTGTTTCCGC[**CG**]TAAACCCCCACACAAAGGCTGCCCGGCCACCGGGTCCCCTGTCCCCCTTCCCGGGGACTT | 121 |
| 122 | cg09797577 | 6 | 28778226 | | GTAGGCTGGACCAGGAAGGAGACCTGGTTCGTTTCGCCCAGGCTGTCACGGCTTCAAGAG[**CG**]CCTCTCCGCTATTTCCGTCGCTCGACAGACGGGCTGAGCTCTTTGGAGTGATGTTGGGTT | 122 |
| 123 | cg20567847 | 7 | 155167038 | | CCGGCGGGGGCTGGGCCGGGCGGGTGGGTTTCTGAGCCGCAGCGCTTGGAGCTGGGGGAG[**CG**]GGAGCAGGGGCGGCCCGGCGGGCGGGCCGGGACCCGGCTTTTCCGGCTACCCGTGGGCCA | 123 |
| 124 | cg04828133 | 7 | 155259845 | | GGAGGTTAATAGCGACTGACGACAAAGGGCCAAGGTGCAATTCCTAAAGCGGGGATTCGC[**CG**]GGTGAGGCAGAAATCAGCCTCCGGGGAGATGGGTCCCCCCTTCCCGACGCGCCCCTGCAC | 124 |
| 125 | cg04521510 | 7 | 27242044 | | CTTCGGTTTTCCGGCCAGACCCGGAAAAACGAAAACACAGCTTGGGGAGCCCCCACTAGC[**CG**]GCGCCTGTGCCAGCTCACCTCTGGCCATGGCGCAGCTGCCGGTGCACACGGCGGCCAAGG | 125 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 126 | cg24304093 | 11 | 14926738 | | TCGGCCTGGCCAGGCGGGGGGTCTTCTTCCCAGTCCGCGGAAGCCAGGTCCGGGAGACGG[**CG**]GGGCTCACTGTGCCTTCGGACCTACACTCTGCTCGGGGGCCGGATTTCTGCAAAGCGTCC | 126 |
| 127 | cg24292235 | 12 | 8171463 | | AGCCTAGGATTCGACTTTGAATGGTCCGTTAATGTGGTCGCAAAACGTGACTCGGTTCAT[**CG**]GGCGCTCCCTGTAAGCAAGACAAGCACCCACCTGCGGTCAGAGCAGGGGTCCGGCTCGCG | 127 |
| 128 | cg25092681 | 5 | 16180033 | Mar-11 | GCGGGAGGGAGGAGCGGCGCGGCGGGGGTGACGGGGCGCGGGCGCGGGGTGGGCTGGGGG[**CG**]CGGATCAGTGGGACGGAGTTCGGGGTTCGGCTCCGAGCGGGCGGGCTGGAAGTGGGGGAT | 128 |
| 129 | cg02984514 | 17 | 31618409 | ACCN1; ACCN1 | GGGGGCGGAACACCAGGCCTCCTGACTGCCGGGGAGTGGGGCGCAGAGGGAGCGGGTTCG[**CG**]CGGAGGGCAACTCACGGAGGAGAAGTTGTGCGGCCCGCAGAGCTCGCCGCGGTACTTGCA | 129 |
| 130 | cg07113542 | 20 | 2781262 | CPXM1; CPXM1 | AGCAGGAGCCCCCACATGGCGGGGATTGAGTGCCAGGGGCGCGCGGGCTACGGCGGGTGG[**CG**]GGTCGGTCTCTTCCTGCCGAGTGCGCCGAGCCCCCCGCCCCTTCCTGCCCCCCGCCCCTC | 130 |
| 131 | cg04609163 | 11 | 125774090 | DDX25; PUS3 | CGTAAAGCGCGGCGGGGAGTCCGGGGGGCTCCCGCCTGGAGGGCTGTGTGAGCGGCGGGC[**CG**]CGGGGCGGCGCGGGGGGCGCTCTCCACTCTGCGGAAGCTGCCCCCTCTGCCCTCCGGTCC | 131 |
| 132 | cg11193865 | 14 | 101193038 | DLK1 | CGGCCGCGTGCTGTACAGTGTGAGGGAACGTGTACCAAACGCTCGCGGGATACCTGTGCC[**CG**]TCTAGCCAAGAGTGCACCCGTGTGCGCGAGCGGGCTTCTGGGACGCCGCCGTGGTCGGGG | 132 |
| 133 | cg09124223 | 7 | 153749738 | DPP6; DPP6 | GGGGAGGGGGCGGAGGAGGCTGAGCCAGGCAGAGTCGCCAGCGGAGACTCGCGAGTGGCG[**CG**]CGGGAGGAGCGGCCGCCGGCGCTGGGCTTGCCTTGCTGCTGCTGCTGCTGCCTCCCC | 133 |
| 134 | cg14768785 | 3 | 172166517 | GHSR; GHSR | ACACCTCCCCTTTCCCCCACCAACTCCCCCAAAGTTTCTCCCAACACATCCTCCGGCCGA[**CG**]CCCACACGCATACCTGTCACCAGCCCTGCCTCGCATTTGCGTTCTCGATCCAGTTCCATC | 134 |
| 135 | cg12477716 | 17 | 47073436 | IGF2BP1; IGF2BP1 | GTATCCGGGACTCCGAAACGCGCGGCGAGCAGCCCCCTCCCCCACCGCCCAGACGGGGTG[**CG**]ACCGCCCACGTGTCGCCCCTTGCCCAGTCGGGTCCTTCCCTCGGGCTCCGGGAGCCGGAG | 135 |
| 136 | cg24826867 | 16 | 85932853 | IRF8 | GAACGCGGGCGGCGAGACGGCGGCAGGACGGCGGCAGGTAGGCACAGTGGGCGGGTAGGG[**CG**]CCCGTGTCCCGCGCGGTCCGGTCCCGCGGGGTCCCCGACGCCAGGCGGGGCGTGGGGGTG | 136 |
| 137 | cg24663256 | 4 | 21950307 | KCNIP4; KCNIP4 | ACATTCATGTCTAGGGACGCAGGGTGCAGAAGCGAGACTCGAGAGTCCACCGGCCAGGGG[**CG**]TCTGTCCACGGGTCTGCACGGGAGCGCACCGCCGCTCGGCCCGGGGGCGTCCGTGGCGCT | 137 |
| 138 | cg06653045 | 17 | 68165064 | KCN12 | TAATTCGCGAACAGTCGGGAGAACAAACAGCCAAGCGGCGCTGCAGTGGCCGCACTTGCG[**CG**]CGTCTCAATCCTGGGGGCTCTGCGCGCCCGCCCCAGTCCCTCGCCCCATTGACTCAGTGG | 138 |
| 139 | cg13592399 | 14 | 52535758 | NID2; NID2 | CCGGTCCCCCTCCATGCTCGCTCGGCCGTGCGCTTACCCGCTGCACAACGCGTCCCGCCC[**CG**]GCCTCCAGCCCACTCTCCGCGCCGCGCCAGCCTCGAACCTGGATCTCCGCGGGCGCCTGG | 139 |

TABLE 1-continued

Table 1 provides a list of 150 MVPs (CpGs) as used in the methods described herein. Provided for each CpGis the Illumina Identifier (Ilmn ID), the chromosome number (CHR) and chromosome position (MAPINFO) specifying the location of the CpGin the human genome, the gene name (if available), a forward sequence encompassing each CpGand a corresponding SEQ ID number. The cytosine of the CG dinucleotide motif subject to modification is identified in bold and in square brackets in each sequence. The CpGs are listed in rank order from 1 to 150. The rank order is in respect to the number of tumours in which a given locus is methylated. Thus, the MVP corresponding to SEQ ID NO: 1 is methylated in the largest number of tumours, whilst the MVP corresponding to SEQ ID NO: 150 is methylated in the lowest number of tumours.

| MVP No. | Ilmn ID | CHR | MAPINFO | UCSC_REFGENE_NAME | FORWARD SEQUENCE | SEQ ID NO. |
|---|---|---|---|---|---|---|
| 140 | cg20008332 | 2 | 5833169 | SOX11 | CGCTGGAAAATGCTGAAGGACAGCGAGAAGATCCCGTTCATCCGGGAGGCGGAGCGGCTG[**CG**]GCTCAAGCACATGGCCGACTACCCCGACTACAAGTACCGGCCCCGGAAAAAGCCCAAAAT | 140 |
| 141 | cg02071005 | 2 | 175200844 | SP9 | TTCCTCTTGCCCTCCTCCTTCTTGCTCCCTCCCCCATCCCACCCACTCTAGGAAGAGCCG[**CG**]CTTCGGAACGACCCCGTTGGCCATGCTGGCGGCGACCTGCAACAAGATCGGCAACACGAG | 141 |
| 142 | cg23302682 | 6 | 166580952 | T | ATCATCTCATTGGTGAGCTCCTTGAAGCGCAGCCACAGCTCGCTCTCCTCCAGGCCCACG[**CG**]CAGTTCGCGCTCTGTGGGGTCGCCCTTCTCGCTGCCCGCCTGCAGCTCATTCTCCACGGC | 142 |
| 143 | cg07978472 | 4 | 122686493 | TMEM155; LOC100192379 | GCCAAGGAGCTGAGGAAATCCGGCGCAGACTCTCCCAGCTGGCACCAAAGCCTTCCGCTT[**CG**]CCGAGATCCTCTCAGGTGCTCTTGAGGACGCGAGCGACTTCCCTAGGAGCGAACTTCCGC | 143 |
| 144 | cg14732324 | 5 | 528621 | | CCCTCGGGGACAGCCCGGCCGGCCACGCCGCCGAACTCGCCATGGGCCTCTCTCCGCATC[**CG**]CATGTGCATCCGCAACCGCTTCCGTCCCGCTGAGCGCACGAACCCTCTCGCTCCTGTCCC | 144 |
| 145 | cg00228475 | 6 | 58149279 | | TCCTCAAGAGAGGTAGGGTCCGTTCCCCCCGGCGGGGCCGGTTAGCTCAGTTGGTTAGAG[**CG**]TGGCGCTAATAACGCCAAGGTCGCGGGTTCGATCCCCGTACGGGCCACAGGCTTTTCTAA | 145 |
| 146 | cg12812583 | 8 | 23567310 | | GAGCAGGCTCCCCAGCGTAGCGAGTCCTTGTTATCGAAAGGGTCGTTTCGGCTCAGGATG[**CG**]CGCTCCCGGCGTAGACCTGGGGATAGGGGTCCCTGTCCCGCTCGCCCCACCCCTGCAGGG | 146 |
| 147 | cg01163842 | 14 | 95235125 | GSC | GTGGCGGCGGGACACCCCGCGCAGGCCAACAAAAGGAGGGGAGCCGCTCGCTCCCGCTTC[**CG**]CGTTTTCATTCAACTTCCTGGGCCTAAAGCGCCCTCCAGCAGCCTGCGGGCCGCCATCGG | 147 |
| 148 | cg17394649 | 6 | 29760164 | HCG4 | AAACGCCGTCTGTGGGGAGTAGCTAGGGGCCTGCCCGGCGGGGGCGCAGGAACCCGGTTG[**CG**]CTGCCGGGAGGAGGGTCGGGAGGGTCTCAGCCCCCTCCTTGCTCCCAGGCTTCCACTCCT | 148 |
| 149 | cg10723962 | 6 | 26240782 | HIST1H4F | GCGTGACAACATACAGGGCATCACGAAGCCCGCCATCCGTCGCTTGGCCCGACGCGGCGG[**CG**]TGAAACGCATTTCGGGCCTCATTTATGAGGAGACCCGCGGTGTTCTTAAGGTGTTCCTGG | 149 |
| 150 | cg17466857 | 7 | 27225528 | HOXA11AS; HOXA11 | GGCTTGTCCGATTTGCACGGTGACTTGATTACACTCTCTCATTCATGGTCACTTCCGAAG[**CG**]CTTTAGTGCCTTCCGTCCCTAAACCGCCAACAGCCAGAACGGCTTCTCCCCGCGGTTTGT | 150 |

TABLE 2

Table 2 below provides exemplary primers which may be used to amplify or sequence MVPs defined in Table 1 above.

| Chr | Sense Start | Antisense Start | Sense sequence | Sense SEQ ID NO |
|---|---|---|---|---|
| 2 | 119, 606, 705 | 119, 606, 804 | TTGGAGGATTAGTATTYGATTATGTTGAA | 152 |
| 19 | 54, 926, 752 | 54, 926, 852 | CCTCAACTTAAATACATCTCCTCC | 153 |
| 7 | 70, 597, 038 | 70, 597, 139 | GGGGTGGGGTGGATTT | 154 |
| 4 | 111, 544, 332 | 111, 544, 433 | CCTCCTCCCAAACCCTTCT | 155 |
| 7 | 27, 205, 053 | 27, 205, 155 | GTTTAGGGTTTTAGTGGTGGT | 156 |
| 7 | 5, 569, 082 | 5, 569, 184 | GGAAATYGGGAGGTTTTTGTGTA | 157 |
| 1 | 237, 205, 102 | 237, 205, 205 | ATCTCTACTTAAAAATTAACCACCC | 158 |
| 15 | 68, 122, 063 | 68, 122, 166 | RCCTTACCAAATTCCTCACAA | 159 |
| 13 | 78, 493, 251 | 78, 493, 354 | TTTGGTTGGTTGAGTTATAGTTTT | 160 |
| 7 | 70, 597, 035 | 70, 597, 140 | GGYGGGGTGGGGTGGA | 161 |
| 8 | 65, 290, 282 | 65, 290, 387 | RTTTTCACTACTCCAACTCCC | 162 |
| 18 | 74, 961, 907 | 74, 962, 016 | TTTGGAAAAGTYGGGAGGGAG | 163 |
| 6 | 28, 367, 508 | 28, 367, 619 | YGGAATTTATTAAAAGTGATTTATAAAGGT | 164 |
| 2 | 223, 163, 755 | 223, 163, 866 | CCCAAAACTTAATCAAAAACCCT | 165 |
| 6 | 166, 582, 153 | 166, 582, 264 | CCTCCTCRCTCTCTTATAAAAACAAAACT | 166 |
| 8 | 26, 723, 555 | 26, 723, 669 | GGGGAATTTTGGAGGATGTATT | 167 |
| 6 | 108, 440, 301 | 108, 440, 416 | GGGGATTAAGGGATTGTTTATTTTG | 168 |
| 8 | 132, 054, 523 | 132, 054, 639 | GTTTAGTGTYGGTGTTAATGATAGATG | 169 |
| 5 | 115, 152, 343 | 115, 152, 460 | AGGTTTAGATTTGTGGGGTTTA | 170 |
| 10 | 106, 401, 968 | 106, 402, 085 | TTAAAGATGAGTGGGGGAGG | 171 |
| 11 | 20, 618, 161 | 20, 618, 279 | AAAGTAATTAAGGTYGTAGTGATTGGT | 172 |
| 19 | 54, 926, 741 | 54, 926, 860 | GGGTTATYGGTTTTTAGTTTGGGTG | 173 |
| 2 | 223, 163, 760 | 223, 163, 880 | AGTTTGGTTAGGAGTTTTGAGT | 174 |
| 22 | 22, 862, 820 | 22, 862, 940 | CCTACACTCCCCCACAAAA | 175 |
| 11 | 120, 434, 955 | 120, 435, 076 | YGGGGGAAAATGTTTTTATTGA | 176 |
| 8 | 23, 563, 877 | 23, 563, 998 | CCTCACAAAAACCCCCAAAA | 177 |
| 2 | 198, 650, 902 | 198, 651, 024 | TATTTGGYGGGTGGGGAGAA | 178 |
| 6 | 10, 882, 276 | 10, 882, 398 | ACCTCTAACAACTACCCCCT | 179 |
| 20 | 25, 065, 180 | 25, 065, 302 | CCACCCAAAACCCAACRTCAAATTA | 180 |
| 7 | 27, 204, 952 | 27, 205, 074 | GTTTGTYGGGGAGGTTGGTTT | 181 |
| 5 | 172, 671, 485 | 172, 671, 608 | CCTCTTCCTTCCTTCCAAATC | 182 |
| 3 | 147, 113, 701 | 147, 113, 826 | GGGAAAGGATAAGGGAAGGG | 183 |
| 12 | 85, 667, 301 | 85, 667, 427 | AGAGTTGTTTTTGATTGTAAGGGA | 184 |
| 7 | 27, 232, 754 | 27, 232, 882 | ACCACTCACCCRCACAAACAC | 185 |
| 8 | 145, 106, 354 | 145, 106, 483 | RTATAAAAACAAAACACATCCTATTAAC | 186 |
| 11 | 112, 833, 711 | 112, 833, 841 | GGGGYGGGTTAGGGAGTATTT | 187 |
| 7 | 155, 259, 749 | 155, 259, 880 | AAATTGTAGTTTGTTAGGTTGAGT | 188 |

TABLE 2-continued

| Table 2 below provides exemplary primers which may be used to amplify or sequence MVPs defined in Table 1 above. | | | | |
|---|---|---|---|---|
| 4 | 174, 450, 311 | 174, 450, 443 | AAAAATAAAAATTCTCCTCATaactacaa | 189 |
| 8 | 132, 054, 519 | 132, 054, 651 | AAAAACTTAATACCRATACTAATAACAAATAAAC | 190 |
| 10 | 118, 030, 953 | 118, 031, 086 | AACTCCCRAACCACCCCC | 191 |
| 1 | 111, 217, 615 | 111, 217, 749 | CTCTCCRCCCCCTCCCCTA | 192 |
| 15 | 86, 233, 181 | 86, 233, 315 | CTCAAAACTACTAAACTCTACCCTA | 193 |
| 1 | 248, 020, 537 | 248, 020, 671 | GGGAGGYGGGTTATGGTTTGG | 194 |
| 2 | 66, 667, 006 | 66, 667, 141 | TTTGAGAAATGTGAATTAGTTATTTGT | 195 |
| 5 | 16, 180, 236 | 16, 180, 371 | TTGGATGGGTYGGTGGGATG | 196 |
| 3 | 42, 306, 888 | 42, 307, 023 | ACCACAACTAACTCTTAATATCCT | 197 |
| 7 | 24, 323, 740 | 24, 323, 875 | AACTACCCRAAACCCCTCCT | 198 |
| 10 | 15, 761, 845 | 15, 761, 980 | AAAATCTAACRATCCCCAACTACC | 199 |
| 8 | 72, 755, 998 | 72, 756, 133 | GGGGGTATTTAGGGTAGGTTG | 200 |
| 12 | 54, 408, 585 | 54, 408, 721 | YGTTTGGAAAGAAATGGAGGTA | 201 |
| 3 | 147, 113, 681 | 147, 113, 817 | CAAAAACCTTCCCACACCC | 202 |
| 11 | 71, 955, 309 | 71, 955, 445 | AAAACCCAAACACCRCCCAAAA | 203 |
| 6 | 29, 760, 051 | 29, 760, 188 | GGGGGTTTTGGTTTTGATTTAG | 204 |
| 2 | 66, 667, 480 | 66, 667, 618 | AAGATTGAGTTTTGGGTTTGTT | 205 |
| 11 | 71, 955, 292 | 71, 955, 431 | GAAGGGGYGGGGTTTAGGAG | 206 |
| 1 | 50, 886, 838 | 50, 886, 977 | TTCTCCTCCTACRCCTACTACCT | 207 |
| 14 | 95, 235, 085 | 95, 235, 226 | GTAGGTTAATAAAAGGAGGGGAG | 208 |
| 7 | 5, 569, 280 | 5, 569, 421 | ATTATTTATGGTGAGTTGYGAGAATAGT | 209 |
| 10 | 15, 761, 835 | 15, 761, 977 | GGGGGTTGGTGGAATTTG | 210 |
| 1 | 119, 530, 560 | 119, 530, 702 | TCTCCACCCTCCCCCT | 211 |
| 4 | 174, 450, 301 | 174, 450, 443 | AGTTAGTTATGGAAGTAGGGGT | 212 |
| 7 | 5, 569, 274 | 5, 569, 417 | GATATTATTATTTATGGTGAGTTGYGAGAATA | 213 |
| 2 | 198, 650, 997 | 198, 651, 141 | AGTTTYGGTTGTGGTTTTGGGA | 214 |
| 3 | 42, 306, 941 | 42, 307, 085 | GGATGATATTATTTGGTTTTGTTTAGAG | 215 |
| 7 | 19, 184, 912 | 19, 185, 056 | GGGGAGGTTAGGGATAGGTT | 216 |
| 14 | 52, 734, 499 | 52, 734, 643 | CAACCTTCACTCCAACCCT | 217 |
| 13 | 109, 147, 820 | 109, 147, 965 | GGGGAAYGTGGAAAGGAGGG | 218 |
| 1 | 50, 513, 833 | 50, 513, 979 | AAAAATACRCCTCAAAAACCAAATAAAAAC | 219 |
| 14 | 101, 192, 985 | 101, 193, 133 | GTGTTGTATAGTGTGAGGGAA | 220 |
| 20 | 21, 686, 229 | 21, 686, 377 | RAAAACCAATAAACTACCAACTC | 221 |
| 7 | 24, 324, 907 | 24, 325, 055 | GTTTTTGTTYGTGTGTTTGGGTG | 222 |
| 2 | 66, 666, 426 | 66, 666, 575 | TGGGGTTGGGATTTTTAGGT | 223 |
| 5 | 76, 923, 868 | 76, 924, 017 | GAGTTTTGGTAGGTGTTGGT | 224 |
| 2 | 66, 667, 385 | 66, 667, 534 | CTCTACAAAATAAAATCAAAAACACCA | 225 |
| 10 | 106, 401, 990 | 106, 402, 139 | TCTATACTCACTTTCTCCAATACTT | 226 |
| 20 | 2, 781, 198 | 2, 781, 347 | AACAAACAAAAACCCCCACA | 227 |

TABLE 2-continued

| Table 2 below provides exemplary primers which may be used to amplify or sequence MVPs defined in Table 1 above. | | | | |
|---|---|---|---|---|
| 11 | 112, 833, 653 | 112, 833, 803 | CAACTCCAAATACCRTTATACCTACCCTA | 228 |
| 1 | 248, 020, 634 | 248, 020, 786 | TGGATTGYGGTTATAGTTTTTGTTTTAGG | 229 |
| 13 | 78, 493, 250 | 78, 493, 403 | CCCTAACTAACTAAACTACAACTCC | 230 |
| 6 | 108, 440, 232 | 108, 440, 386 | TCTAAAAATTAACTCTAACTTCCCCA | 231 |
| 2 | 182, 322, 443 | 182, 322, 597 | TGTTGTTGTTGTGTTTGGGG | 232 |
| 11 | 20, 618, 126 | 20, 618, 280 | RAAAACAAAATCAATTACTATTTTTCATCT | 233 |
| 8 | 145, 106, 394 | 145, 106, 549 | GGGGAGGYGGGTTTAGTGTAG | 234 |
| 15 | 86, 233, 182 | 86, 233, 337 | TTAAAGTTGTTGAGTTTTGTTTTGA | 235 |
| 6 | 29, 760, 062 | 29, 760, 217 | TCCTAACCCAAACCTAAACAAA | 236 |
| 12 | 85, 667, 262 | 85, 667, 417 | TCAAAATAAAAACTCCTCCACCTAT | 237 |
| 4 | 147, 561, 686 | 147, 561, 841 | TGTAGGTATGGTTYGAGGAGGT | 238 |
| 6 | 28, 778, 138 | 28, 778, 295 | GTGAGGGAAGAGAGGTGTTT | 239 |
| 7 | 27, 225, 023 | 27, 225, 180 | TGTAGTTATTTTAGGGGAAGTAATAGAT | 240 |
| 14 | 24, 045, 512 | 24, 045, 669 | GGTAGGGGYGGGGGTGG | 241 |
| 13 | 28, 366, 707 | 28, 366, 864 | RTTCAACCTCCTAAACAAAAACAA | 242 |
| 4 | 147, 561, 678 | 147, 561, 835 | ACCCATCCTACAAACATAACTC | 243 |
| 10 | 22, 518, 210 | 22, 518, 368 | GAAGATTTYGGGGAAGGAGTGG | 244 |
| 7 | 27, 225, 011 | 27, 225, 169 | ACTTCCTTTCTTTATAACCACCTC | 245 |
| 14 | 95, 234, 999 | 95, 235, 157 | RAAAAACAAAACAATTCAAATCAA | 246 |
| 1 | 50, 513, 832 | 50, 513, 991 | GGAAGATGYGTTTTAAGAATTAGGTAGAA | 247 |
| 10 | 106, 401, 430 | 106, 401, 589 | GGGTYGGGGTATTTTAGTTTTTGT | 248 |
| X | 136, 656, 476 | 136, 656, 635 | GAGGTTTGGGGATTGGTTG | 249 |
| 2 | 66, 666, 980 | 66, 667, 139 | CCCTCTTCCCTCTCTTAACAC | 250 |
| 10 | 106, 401, 346 | 106, 401, 505 | AAAACTACTACCCCAACAAAAC | 251 |
| 12 | 62, 584, 934 | 62, 585, 094 | GGGGAAGGGAGAYGTGTGTA | 252 |
| 1 | 111, 217, 518 | 111, 217, 678 | CCCACCRCCTATTACAACCAAAAC | 253 |
| 2 | 66, 666, 422 | 66, 666, 582 | ACCTTAAAATTAAAATCCCTAAATACAAC | 254 |
| 5 | 115, 152, 387 | 115, 152, 547 | RCTTAAAATCACTAAAAATATACCAAC | 255 |
| 5 | 180, 596, 604 | 180, 596, 764 | GTGTAAgttttygtagtgtagtggt | 256 |
| 22 | 50, 216, 544 | 50, 216, 704 | TCCCAAAATCCCACACTACA | 257 |
| 7 | 27, 225, 490 | 27, 225, 651 | ACTTAATTACACTCTCTCATTCATAATC | 258 |
| 11 | 120, 434, 988 | 120, 435, 149 | RCAACTTCTACCTTTTATTACAAAC | 259 |
| 1 | 237, 205, 044 | 237, 205, 207 | AATTTTTATTTGATTATGAATAGAGGTAATTT | 260 |
| 20 | 2, 781, 222 | 2, 781, 385 | GGGGATTGAGTGTTAGGGG | 261 |
| 7 | 5, 569, 852 | 5, 570, 016 | CCACCCTACRATCCCCATTAAC | 262 |
| 2 | 175, 199, 604 | 175, 199, 769 | TCTACTCTACCTACRCCCTCATTAAA | 263 |
| 18 | 44, 787, 470 | 44, 787, 635 | CRAAATCCTCCCTCCTACCTC | 264 |
| 11 | 14, 926, 608 | 14, 926, 773 | CACAAACCCAAAAACCCCA | 265 |

TABLE 2-continued

Table 2 below provides exemplary primers which may be used to amplify or sequence MVPs defined in Table 1 above.

| | | | | |
|---|---|---|---|---|
| 20 | 25, 062, 422 | 25, 062, 588 | GTTAGGAGTAGGTAGGGTGT | 266 |
| 6 | 391, 841 | 392, 007 | GTGAGGTTGATATTAGAGAGGAT | 267 |
| 7 | 19, 184, 852 | 19, 185, 019 | RCAAAAACTAAATCCCCCAAAAA | 268 |
| 5 | 140, 787, 404 | 140, 787, 572 | TTGAGGGGGATGTATATTTGTATT | 269 |
| 18 | 74, 961, 845 | 74, 962, 014 | RACTCTATCCACCACCAA | 270 |
| 6 | 27, 513, 424 | 27, 513, 594 | AACCATTATAAATTCACCCCAAC | 271 |
| 6 | 26, 240, 675 | 26, 240, 845 | GGTAAAGGTTTAGGAAAGGGAG | 272 |
| 6 | 28, 778, 185 | 28, 778, 355 | AAACCTAATTCRTTTCACCCAAACTATC | 273 |
| 2 | 66, 666, 605 | 66, 666, 776 | TCCACCRAATCCTAAATATACAATAAAAA | 274 |
| 7 | 27, 204, 213 | 27, 204, 386 | TTAAGGAGAGGGGYGGTTAGTT | 275 |
| 20 | 25, 065, 065 | 25, 065, 239 | ACATTTTCATAACCTCCTACAATAAA | 276 |
| 7 | 20, 817, 774 | 20, 817, 949 | CTACAAAACRAAAACAAAACACAAAATAA | 277 |
| 11 | 125, 773, 960 | 125, 774, 135 | AACCAATTCRCTAACCTTTCTAACATC | 278 |
| 7 | 27, 204, 899 | 27, 205, 074 | CCTTAAACTAAAAACTACACRAACTAAAAT | 279 |
| 5 | 172, 671, 421 | 172, 671, 597 | AGTGTTGAATTGATGTTGGAAA | 280 |
| 18 | 55, 108, 733 | 55, 108, 909 | TCTACACCCCCTCCCC | 281 |
| 14 | 70, 653, 838 | 70, 654, 015 | TTTTTGATTATTTAGGAGTTTGGTTG | 282 |
| 6 | 99, 841, 571 | 99, 841, 748 | AAACACAAATACAAAACTATACATAACT | 283 |
| 14 | 24, 045, 441 | 24, 045, 620 | CCCCRAACCCAACCAACA | 284 |
| 2 | 66, 666, 618 | 66, 666, 799 | GGATGTGTAGTGGAGGGG | 285 |
| 10 | 135, 043, 371 | 135, 043, 552 | gggggtAGTATTGGGGGT | 286 |
| 4 | 122, 686, 466 | 122, 686, 647 | CCCAACTAACACCAAAACCTT | 287 |
| 20 | 37, 352, 962 | 37, 353, 143 | TCCAATCCCCCACCCC | 288 |
| 7 | 27, 204, 196 | 27, 204, 378 | ATCCTAAACCTAAACAACCAAAAA | 289 |
| 8 | 26, 723, 434 | 26, 723, 616 | CCAAAACCCCAAACTCCAA | 290 |
| 1 | 50, 886, 642 | 50, 886, 825 | RCTCTCACCTAAACCCCC | 291 |
| 6 | 27, 513, 336 | 27, 513, 519 | GTTATTGATGTGTTTTGAATGAGTT | 292 |
| 7 | 5, 569, 687 | 5, 569, 870 | ACACCCCRAACCCCAAAAC | 293 |
| 10 | 22, 518, 180 | 22, 518, 364 | CCAACACCCTAACRAAACCTAAAC | 294 |
| 7 | 27, 232, 735 | 27, 232, 920 | GTTAGTTTGTAGTTGYGGGGTTATTTA | 295 |
| 2 | 162, 283, 572 | 162, 283, 757 | ACAATACATTCRTATCATCACCCACC | 296 |
| 2 | 45, 161, 903 | 45, 162, 088 | aaatctaccccaccctacc | 297 |
| 6 | 166, 582, 063 | 166, 582, 250 | GTTTTTATTATTTGGAAAAGGAAGGTT | 298 |
| 8 | 72, 756, 006 | 72, 756, 193 | CCAAAACAAACTAATCTTAAACCTAAA | 299 |
| 14 | 29, 254, 632 | 29, 254, 819 | CCCTCTTTCCCCTTCAATCTT | 300 |
| 15 | 76, 629, 983 | 76, 630, 170 | ATCATCTTTCCTTATAATCRCAAATCTTAAAAA | 301 |
| 8 | 72, 754, 933 | 72, 755, 121 | ACTTCTTTAATATCAAAATCCRATCTTCC | 302 |
| 8 | 23, 567, 163 | 23, 567, 352 | atactttctaaCCCCTCTCRAAAAATA | 303 |
| 12 | 62, 584, 867 | 62, 585, 056 | ACCCRCATCTACCCTCACCT | 304 |

TABLE 2-continued

Table 2 below provides exemplary primers which may be used to amplify or sequence MVPs defined in Table 1 above.

| | | | | |
|---|---|---|---|---|
| 7 | 5, 569, 805 | 5, 569, 994 | CAATAACRCCCCAACCCCCAC | 305 |
| 19 | 58, 238, 678 | 58, 238, 868 | CTAAAACACAAAAACTACAAACACT | 306 |
| 5 | 16, 180, 017 | 16, 180, 207 | yggggtgggttgggg | 307 |
| 13 | 28, 366, 672 | 28, 366, 863 | AGAGGTTATTGTTTTAGTTTAGGTTT | 308 |
| 1 | 248, 020, 475 | 248, 020, 666 | ACTCCTCCCCCTATACAAAC | 309 |
| 4 | 147, 559, 282 | 147, 559, 473 | AAACCCTACAACCCCTCC | 310 |
| 3 | 147, 113, 702 | 147, 113, 894 | GGAAAGGATAAGGGAAGGGT | 311 |
| 4 | 147, 559, 273 | 147, 559, 465 | AGTGAGAGAAAGTTTTGTAGTTTT | 312 |
| 6 | 10, 882, 217 | 10, 882, 409 | GGGYGGGGTTTTGTTTTTGGT | 313 |
| 12 | 54, 408, 539 | 54, 408, 731 | ACAATACCCRCTCCCCCACC | 314 |
| 18 | 22, 930, 230 | 22, 930, 422 | RATCAACTTCTAAAAATAACCAAAAA | 315 |
| 8 | 72, 754, 903 | 72, 755, 096 | GTGGTTTTATATAGTTTGTTGGTTG | 316 |
| 2 | 66, 667, 490 | 66, 667, 683 | TCTAAACTTATTTTCAACTTATTTAATTCAC | 317 |
| 20 | 21, 492, 888 | 21, 493, 082 | GATGAGGTTGGTTAGGTGTT | 318 |
| 6 | 391, 785 | 391, 979 | CCCTCAACTCCRAATCCAAAAC | 319 |
| 7 | 24, 324, 845 | 24, 325, 039 | CTTCTATACCTACAAATACTAAATAACAAA | 320 |
| 7 | 70, 596, 935 | 70, 597, 129 | AAACCRATATACCCTAAAAACCCC | 321 |
| 5 | 528, 491 | 528, 685 | RACAAACCCTCCCAACA | 322 |
| 2 | 66, 667, 301 | 66, 667, 496 | TGTTTGAGTGTTTGTTTGTAGAT | 323 |
| 4 | 174, 450, 245 | 174, 450, 440 | GGTTGTAGGATAGGGTTATGTTG | 324 |
| 20 | 21, 686, 179 | 21, 686, 374 | GGAGGGGGTAGAGTTTTAGG | 325 |
| 1 | 149, 719, 383 | 149, 719, 579 | ATGTTGAGGGTGTTAYGGTTTTATT | 326 |
| 7 | 1, 272, 352 | 1, 272, 548 | GTTTATTGAGGTGTATGTTAGGTATAAT | 327 |
| 2 | 119, 607, 734 | 119, 607, 930 | AATTCATTTTACCTTTCATATAATAAAACC | 328 |
| 15 | 68, 122, 089 | 68, 122, 286 | GGGTTGGGGGTAGYGGAAAAT | 329 |
| 15 | 76, 630, 037 | 76, 630, 234 | GTTGGGTTGGGGTTGGA | 330 |
| 3 | 129, 693, 494 | 129, 693, 691 | CCTCCCCACTAACCTCAC | 331 |
| 5 | 172, 659, 564 | 172, 659, 761 | TCCCTTCCCTACCAAACTC | 332 |
| 7 | 149, 917, 234 | 149, 917, 431 | CCCTCCACAAACCTACCAAA | 333 |
| 14 | 60, 975, 848 | 60, 976, 045 | CCAATCCRCCCACCCCAATAAC | 334 |
| 2 | 162, 283, 566 | 162, 283, 764 | AGTGGAGTAGTGTATTYGTGTTATTATTTA | 335 |
| 20 | 21, 081, 785 | 21, 081, 983 | GGGATGGGGAAATTATTTGATTAG | 336 |
| 8 | 23, 563, 886 | 23, 564, 084 | GATTTTTAGGAGGTTTYGAATTATTTAGTTT | 337 |
| 16 | 85, 932, 830 | 85, 933, 028 | GTAGGTATAGTGGGYGGGTAGG | 338 |
| 13 | 53, 420, 219 | 53, 420, 417 | CCCCTTTACRCACCTCCTTCTT | 339 |
| 2 | 119, 606, 711 | 119, 606, 910 | AACCAATATCCRACTATACTAAAACCTA | 340 |
| 7 | 27, 205, 063 | 27, 205, 262 | CCAATAATAACCATCACCRTACCCAA | 341 |
| 22 | 50, 216, 594 | 50, 216, 793 | TTTATTTTTGYGGGGGAATATAAGGAG | 342 |

TABLE 2-continued

| Table 2 below provides exemplary primers which may be used to amplify or sequence MVPs defined in Table 1 above. | | | | |
|---|---|---|---|---|
| 22 | 50, 922, 498 | 50, 922, 697 | CAACAAAACTCAAAACATTCCC | 343 |
| 22 | 22, 862, 796 | 22, 862, 997 | GGGGATYGTGGGATTTGGTT | 344 |
| 1 | 111, 217, 055 | 111, 217, 259 | GGGAATTGGTAAAGGGTTTTTAG | 345 |
| 6 | 28, 367, 514 | 28, 367, 722 | CCATCAAAAATAACCCACAAAAAC | 346 |
| 1 | 111, 217, 355 | 111, 217, 565 | GGGYGTTGAGGAGGGTGG | 347 |
| 2 | 119, 607, 767 | 119, 607, 977 | ATTTGTTATAGTAATGGGATGATAAATG | 348 |
| 7 | 149, 917, 184 | 149, 917, 394 | AGTTATYGATTTTTGTAAGGGATGTAGA | 349 |
| 2 | 63, 281, 084 | 63, 281, 295 | AAGGTYGAGATTTGGGTTTGTTAG | 350 |
| 1 | 50, 886, 613 | 50, 886, 825 | TTTGTTGTTTTTATTTGYGGTTTGGT | 351 |
| 5 | 135, 266, 111 | 135, 266, 323 | RAACTCCAACACCTTAACC | 352 |
| 7 | 155, 166, 900 | 155, 167, 114 | GGTAGGAAGAAGGGYGATGTTTTT | 353 |
| 14 | 95, 239, 509 | 95, 239, 725 | ACTAAACAAACCATCAAAACCC | 354 |
| 10 | 118, 030, 867 | 118, 031, 084 | TTTTAAGGGTTTGTTTTAGAGTTTG | 355 |
| 3 | 147, 113, 558 | 147, 113, 776 | AGTTGGGATTTGAGGAAATTTAG | 356 |
| 11 | 20, 618, 134 | 20, 618, 352 | AATCAATTACTATTTTTCATCTTTAACAAAA | 357 |
| 10 | 118, 030, 866 | 118, 031, 086 | ACTTCAAAAATTTACTCCAAAACCT | 358 |
| 11 | 71, 955, 207 | 71, 955, 427 | AATACAACRCAAATACAACCAACCC | 359 |
| 11 | 14, 926, 603 | 14, 926, 824 | GGGTGTATAGGTTTAGGGGT | 360 |
| 5 | 15, 500, 202 | 15, 500, 423 | CCTCCCCRAAACTCCAACTAT | 361 |
| 2 | 63, 281, 053 | 63, 281, 282 | TCTTTTATTCCCAATTCRACTTTCTTT | 362 |
| 14 | 29, 254, 647 | 29, 254, 879 | AGTTTTTAGGGAGGGGGAG | 363 |
| 1 | 111, 217, 544 | 111, 217, 780 | YGATGTTTTGTTTGGGTTTGG | 364 |
| 11 | 31, 848, 615 | 31, 848, 857 | GTTGGGTTGGGAGAAGTTT | 365 |
| 4 | 111, 544, 173 | 111, 544, 425 | GGGTTTTGTYGTAGTTTAGTTTTAGG | 366 |
| 7 | 27, 205, 054 | 27, 205, 314 | TTTAGGGTTTTAGTGGTGGTT | 367 |
| 19 | 58, 238, 712 | 58, 238, 972 | GGAGTYGGAGAAAGGGTGATT | 368 |
| 5 | 180, 596, 452 | 180, 596, 712 | CATCTCAACCTTCCAAATACTAAA | 369 |
| 2 | 63, 283, 871 | 63, 284, 132 | TGGYGTGTTTTTGTTTATTGGAGTATT | 370 |
| 15 | 65, 116, 211 | 65, 116, 473 | ACAATCCRAAAACAACAACTACACT | 371 |
| 5 | 140, 787, 349 | 140, 787, 617 | ATTTAAAACACAAAACATAAAAATATCTACTA | 372 |
| 14 | 95, 239, 425 | 95, 239, 697 | GGAGGTAGGTTTYGGGAAAGG | 373 |
| 10 | 135, 043, 275 | 135, 043, 552 | ACCCATCCCCTAACCTAAC | 374 |
| 19 | 58, 238, 625 | 58, 238, 903 | CCCACACCCACCCAC | 375 |
| 6 | 26, 240, 714 | 26, 240, 993 | AAAATACTACRTAACAACATACAAAACATCAC | 376 |
| 20 | 25, 065, 005 | 25, 065, 285 | TGTGTTTTGGGTTATTTTGTGTT | 377 |
| 7 | 155, 259, 636 | 155, 259, 918 | AAAATTCTACTAAAAATCATTCTATCTCC | 378 |
| 5 | 172, 659, 477 | 172, 659, 760 | GGATTTAGGGTTATGTTGGGAG | 379 |
| 7 | 20, 817, 773 | 20, 818, 057 | GTTGTAGAAYGGGAGTAGGGTATAG | 380 |
| 14 | 52, 734, 368 | 52, 734, 652 | GGAGGTTTTTGTYGTGGGGAATA | 381 |

TABLE 2-continued

Table 2 below provides exemplary primers which may be used to amplify or sequence MVPs defined in Table 1 above.

| | | | | |
|---|---|---|---|---|
| 20 | 61, 638, 444 | 61, 638, 729 | CACAAACCRAAAATAAAAACTCTAAACC | 382 |
| 18 | 77, 547, 903 | 77, 548, 190 | CTAACAAAACRACCCAACCAAAAA | 383 |
| 11 | 120, 434, 917 | 120, 435, 205 | TTAGAYGGTATTAGGTAGTTGAATTTAGT | 384 |
| 9 | 37, 002, 424 | 37, 002, 713 | GGTTAGTAAGAATGTTATAGTTTTATTTTGT | 385 |
| 1 | 91, 182, 909 | 91, 183, 198 | AACAATCTATAAATACTTTCRACACAACT | 386 |
| 18 | 44, 787, 350 | 44, 787, 639 | AAAACTAAAAATTCCTAAAATCCCTTTA | 387 |
| 1 | 111, 217, 246 | 111, 217, 537 | CAACAAATAATCCCCRAACACCA | 388 |
| 7 | 1, 272, 400 | 1, 272, 691 | RTTTCCCTACACCCAACAC | 389 |
| 11 | 125, 774, 055 | 125, 774, 347 | GGGTTTTYGTTTGGAGGGTTGT | 390 |
| 7 | 24, 323, 635 | 24, 323, 929 | GGGGTGTGGGTGGTTTT | 391 |
| X | 136, 656, 432 | 136, 656, 726 | RACCCCTCCAACCTTT | 392 |
| 1 | 91, 182, 902 | 91, 183, 197 | GGGAAGTGGTAATTTGTGGATA | 393 |
| 7 | 27, 225, 460 | 27, 225, 755 | TGTTTGGTGGTTTGTTYGATTTGTA | 394 |
| 2 | 182, 322, 235 | 182, 322, 530 | CTTCCCTCTCTCCTTCCTTTA | 395 |
| 2 | 63, 283, 941 | 63, 284, 236 | CAAACTACTACCCCTTCAACT | 396 |
| 11 | 20, 618, 153 | 20, 618, 450 | TTTTTGATAAAGTAATTAAGGTYGTAGTGA | 397 |
| 14 | 70, 653, 836 | 70, 654, 133 | ATTTCTTAACCACCCAAAAACTTA | 398 |
| 1 | 119, 530, 348 | 119, 530, 646 | ATTAAGGTTTTAAYGGAGAAGGTATGT | 399 |
| 17 | 47, 073, 268 | 47, 073, 566 | CCCCTAACRCCATCCCAACC | 400 |
| 8 | 23, 567, 042 | 23, 567, 341 | GAAAAGATATTTTGTGGGggatt | 401 |
| 17 | 47, 073, 229 | 47, 073, 528 | YGAGGGGGTTTTAGGGT | 402 |
| 2 | 198, 650, 889 | 198, 651, 188 | ACCCTAAACCTACCACCTAAC | 403 |
| 13 | 109, 147, 667 | 109, 147, 966 | TCCTCCTACTCCCAAAATCT | 404 |

| Chr | Antisense sequence | Antisense SEQ ID NO |
|---|---|---|
| 2 | AATCCRCTAAAACTCTAAAATAACACCC | 405 |
| 19 | TTGTTGGTATTTTTGTTTTTGGG | 406 |
| 7 | CTCAAATCTCAATTACTCTCAAAATAAA | 407 |
| 4 | TGTTGATAGGTGTAGGTAGGATAG | 408 |
| 7 | CCACCAAATTATTACATAAAATCTACAA | 409 |
| 7 | AAAACRCCCCAAACACCAAATAAAA | 410 |
| 1 | TTTTGGATTGGGTTAGGGTATT | 411 |
| 15 | GATTTTYGGGGTGGGTGGG | 412 |
| 13 | ACAACRATTTCCAAATTCCTACTAAC | 413 |
| 7 | RCTCAAATCTCAATTACTCTCAAA | 414 |
| 8 | TGATTGTAAGYGTAGGTTTGGGT | 415 |
| 18 | CAACAATACACTATACRACTCCTACAA | 416 |
| 6 | ACCCCTTTCRCTCCCTTCCTA | 417 |
| 2 | AGAGATGGGAAGAGAAAGTGG | 418 |

TABLE 2-continued

Table 2 below provides exemplary primers which may be used to amplify or sequence MVPs defined in Table 1 above.

| | | |
|---|---|---|
| 6 | TTTTATTTTTYGTGAAAGTAATGATATAGTAGAA | 419 |
| 8 | ATCCTAACCCTAAAATCCCTAAAT | 420 |
| 6 | CCTTCTCAATAAATACATTTACCCC | 421 |
| 8 | AATAACCACCACCRCTCCTCC | 422 |
| 5 | RCCACCTTTCTTAAATAACTCT | 423 |
| 10 | CCCCAAATCAACCCTTTTTC | 424 |
| 11 | RCCTATTTATAATAATAATCAAACCCA | 425 |
| 19 | RATCCCACCTACTAATATTCC | 426 |
| 2 | ACCTCRACACCACCAAAAATAAA | 427 |
| 22 | TGAGGGGAGATTTGAGGGAT | 428 |
| 11 | AATTCCCRAACCCCCTCCC | 429 |
| 8 | GGAAAATTTTTAGTATTTGAGAATGGA | 430 |
| 2 | TCRAAATCCCAAAACCACAACC | 431 |
| 6 | TTTTTGGGATTGTGGTGGAG | 432 |
| 20 | GGGTGGATYGTGGGTTAGTTTT | 433 |
| 7 | AACCACCACTAAAACCCTAAA | 434 |
| 5 | GGTGTGTGTGTGTAATATAATAATTTGT | 435 |
| 3 | ACAAACCAACCACATTTACTTCT | 436 |
| 12 | AAAACCACCTTCCTAACTCC | 437 |
| 7 | ATGGAGGTTTAGGTYGGTGTAAA | 438 |
| 8 | TTATGGGGGYGGGTGATGGA | 439 |
| 11 | ACTTCCCRCCCAACCAACTTC | 440 |
| 7 | ACCCATCTCCCCRAAAACTAAT | 441 |
| 4 | GAAATGAGTTTGGTAGGTGGTT | 442 |
| 8 | GGTGGAGGAGGTGGTGATTA | 443 |
| 10 | YGTTGATTATGGTTGGTTTGTT | 444 |
| 1 | GAGGGGTTTTGAGGGTTGTA | 445 |
| 15 | TGAATTTTATTGTTATGTGGGGTATT | 446 |
| 1 | RAAAATACACCTAAAACAAAAACTAT | 447 |
| 2 | ACTTTTTAACATCTATTTTACTAACCTATT | 448 |
| 5 | CCCTTTCCCRCTCCACTACTC | 449 |
| 3 | GGGTGGTGGTAATTTGGTT | 450 |
| 7 | TGGTTGGGYGGTAAGTATTATGTTG | 451 |
| 10 | AGGGTTAGAGTTTTTGGGTTAG | 452 |
| 8 | CCCTCCCRACCAAAAACTCA | 453 |
| 12 | ACAACAACCRAATAATCCCCATTC | 454 |
| 3 | TTATATTTGTTTTTGGGAGGAGTG | 455 |
| 11 | TGGTTYGGATTGGGGTAGGAT | 456 |

TABLE 2-continued

Table 2 below provides exemplary primers which may be used to amplify or sequence MVPs defined in Table 1 above.

| | | |
|---|---|---|
| 6 | CCTCCCRACCCTCCTCCC | 457 |
| 2 | TCCTAATTTCTTACCTCATTACACT | 458 |
| 11 | ACAAAATAAAAACTCCRAAAATAAAATCCC | 459 |
| 1 | GTGGTGTYGGTTTTTAAGGGTT | 460 |
| 14 | ACCCAACCCTACTTAACTCTC | 461 |
| 7 | ACCCRACTTCCTTTATCCCCA | 462 |
| 10 | ACTAAAACCCCTAAACCAACC | 463 |
| 1 | GGTGGGTGGGAAGTAGGAT | 464 |
| 4 | RAAATAAATCTAATAAATAATTTTCCCC | 465 |
| 7 | RACTTCCTTTATCCCCAATCTa | 466 |
| 2 | TCTCTCCTCCCCAACCRTCTAAAA | 467 |
| 3 | ATCAAATTCCCCAAAACCCT | 468 |
| 7 | TTAAAAATCCCCACCAACAAC | 469 |
| 14 | GGTTAGTAGGTTGTTTAGGAGG | 470 |
| 13 | RTAAAACTAAACTCCAACTCCC | 471 |
| 1 | TTGGGAGTYGGGGTGGTTAG | 472 |
| 14 | CAATCCCTATAACCCCCTCC | 473 |
| 20 | YGATTTTAGGTTTAGGGTGAATTTT | 474 |
| 7 | CCACCCACCTCTACCTAAT | 475 |
| 2 | AAAACTAATTCCTACRAATTCCTCCTA | 476 |
| 5 | AACCTCTTTAAAACCTTCCCTAA | 477 |
| 2 | AGAAATATTTTAGTGTGAATTAAATAAGTTG | 478 |
| 10 | tgggggtaggggGAGTT | 479 |
| 20 | GTTGTGGGYGGGTAGGAGGT | 480 |
| 11 | TGGGAGGGATTYGAGTTGGTTG | 481 |
| 1 | CCACCAAACCCRCCAACTACC | 482 |
| 13 | TAGGTTGGGTAAAGGAAGGA | 483 |
| 6 | GGTTTTTATTTTTYGTTTTTATTTGATGAGTT | 484 |
| 2 | TCAATCCAACTCTACTCACCAT | 485 |
| 11 | YGTTTGTTTATAGTGATAATTAGGTTTA | 486 |
| 8 | CCTAACCAAAAACCRAATTTAATTTAACC | 487 |
| 15 | ACCTCCCCATACTTTAATCCT | 488 |
| 6 | AAGTTTGGGAGTAAGGAGGG | 489 |
| 12 | TTTTGGTTTTYGGTTTGGAGGG | 490 |
| 4 | AAAACCRAAACTAAATAACAAAATAAACTTC | 491 |
| 6 | CAAACCAAAACCCAACATCAC | 492 |
| 7 | AACCCTACAATTAAACACAAACAT | 493 |
| 14 | RCAAACACCTACCAAAACCA | 494 |
| 13 | GTAGTATTAGYGAGTTTATTAGGAAGGAG | 495 |

TABLE 2-continued

Table 2 below provides exemplary primers which may be used to amplify or sequence MVPs defined in Table 1 above.

| | | |
|---|---|---|
| 4 | GAGGTTGAATGGTAAAGTAGGTT | 496 |
| 10 | AAATAAATTTCCAAAAACCAAACAAAA | 497 |
| 7 | TGAGTATAAGTATGTTGTATGGGG | 498 |
| 14 | YGTTTTAGGTTTAGGAAGTTGAATG | 499 |
| 1 | CTCTCCCCCTCCCTAAAAAT | 500 |
| 10 | CACCTCCTCCCRAAAACCCT | 501 |
| X | CCTCCTCTTTCCTCCCAA | 502 |
| 2 | TTTTTAATATTTATTTTGTTGATTTGTTTGG | 503 |
| 10 | TTGGGTGATTGGGGGTT | 504 |
| 12 | CAAAAACTACAAAAACATCRCTAAATATTACC | 505 |
| 1 | GTGGGYGGGAATTTTAAGGGG | 506 |
| 2 | GTTGGGGAGGGTTGGTT | 507 |
| 5 | GAGATAAYGGGGTTTTTGGGAAG | 508 |
| 5 | CCAAATAAAAATAATAATAAAATATTCCAAACT | 509 |
| 22 | GGTTTATATTTAAGGTTAGGAAGAAGG | 510 |
| 7 | AGATGAGGGGAGAGGTGG | 511 |
| 11 | GGAAAGGAGGGTTAYGGGTAAAG | 512 |
| 1 | CCTCCTAAACTAAACTAAAACACTAAC | 513 |
| 20 | ACCCTCTCCTCCTCTCC | 514 |
| 7 | YGGGAGAAGTTTTTGGGTT | 515 |
| 2 | TTGTTYGGAAAAATTGTTTGGGTTT | 516 |
| 18 | GGGTGGGATAGGATAGGGT | 517 |
| 11 | GAGTAGAGTGTAGGTTYGAAGGTAT | 518 |
| 20 | CCAAAACAAAAATCTAACTACRAAAATCC | 519 |
| 6 | AACCTTAAAACCCAAACCAAC | 520 |
| 7 | GAAAATYGATGAGAGGTAGGGTTAAG | 521 |
| 5 | AAAAATCCCAAACCAAAAACTAAC | 522 |
| 18 | GTAGTGTATTGTGTGGTTTTTGT | 523 |
| 6 | TTTGGGTAAGTTTTGAGGAAAG | 524 |
| 6 | CTCCAAAAACACCTTAAAAACAC | 525 |
| 6 | GGAAGTTAGGTAATTTTTGAAGTTTTT | 526 |
| 2 | YGGAGGTTTTGAGTTATGGA | 527 |
| 7 | RAATTAAAACCAAAAACCAAAAAT | 528 |
| 20 | TTTGGTTTTGGTTGAYGTTGAGT | 529 |
| 7 | GGTGGTGGTTTGGGGT | 530 |
| 11 | gggGTAGTTTTYGTAGAGTGGAG | 531 |
| 7 | GGTTATTATTGGGGTTTTGGGTAA | 532 |
| 5 | ACAACACAACAATTTATCAACTACT | 533 |

TABLE 2-continued

Table 2 below provides exemplary primers which may be used to amplify or sequence MVPs defined in Table 1 above.

| | | |
|---|---|---|
| 18 | GGTTTAGTTATTAGGGTTTAGTGGT | 534 |
| 14 | ctttcctctctctctctct | 535 |
| 6 | GGATTAGTGGTTTTGTTTGGAAAA | 536 |
| 14 | GGGTAYGTTAGAGTGTGTTTTATTATTAG | 537 |
| 2 | CCTTCCTCCTAAAACCCTAAAAT | 538 |
| 10 | AATCCTCAAAAATTCTATTCTTAAACC | 539 |
| 4 | ATGTTGGGGGTGGAATTTT | 540 |
| 20 | GGTGGTTAGTGTATTGYGGAGTTG | 541 |
| 7 | GTTAGGAGTTAGAAGTTGGTGT | 542 |
| 8 | TTTTAGGTGATTGYGAGGTAATTTGT | 543 |
| 1 | GTTGTAGTTGTTTTAYGGTATTGTTGA | 544 |
| 6 | aaaaccccaataaatttcaaatcc | 545 |
| 7 | AATGGGGATYGTAGGGTGGG | 546 |
| 10 | GGATTTTTAGGGATTAAGTAAAGAAATTAT | 547 |
| 7 | CAAACCCTCCACRCTTCTACAAAAA | 548 |
| 2 | TGGTTTAGTTTGGGYGGAGAGTA | 549 |
| 2 | GGAAGGGGGATAGGGGAT | 550 |
| 6 | AAAACAATAACACAACAAAAACCA | 551 |
| 8 | GGTTTYGTGTGGTTGGGGG | 552 |
| 14 | TGAGGTTTGTAGTGAAGGGT | 553 |
| 15 | TGGTYGTGGATTTGATTTTTGTAGT | 554 |
| 8 | AGAGGATATGTAAATTTTTAGAATGTTG | 555 |
| 8 | GTGYGATAGGGATTTTTATTTTTAGGTTTA | 556 |
| 12 | GGGAAGYGGGGTTGTAGGTA | 557 |
| 7 | GGAGATGGGGGATATTTTAYGTTAGTT | 558 |
| 19 | TTGATGTTTTGTAGGGATGGA | 559 |
| 5 | CCTACCCCCTACTTCCCA | 560 |
| 13 | CAACACTAACRAATCCACCAAAAA | 561 |
| 1 | TGTATTTGAGGTAGAAGTTGTGG | 562 |
| 4 | GTTTAGGTGATTTTGATTTTAGGTTTT | 563 |
| 3 | TCCAAAACTTTCAACACCATAC | 564 |
| 4 | AACCCTAATCCCAAATTCCC | 565 |
| 6 | CTCCACCTCCRTTCCTAAAACTATAATAA | 566 |
| 12 | AGTTTTATTTGTAGTAGTYGAATGGTTTT | 567 |
| 18 | YGGAGGTGGGGAGTAGTT | 568 |
| 8 | CTAATAAAATCTTAACTACTCCAAATCAA | 569 |
| 2 | GTGAGAAGGAGAGGGGAG | 570 |
| 20 | TCCAAATCCCCRAAACCCTC | 571 |
| 6 | GTTTAGYGTAGATGGGGTGGGA | 572 |

TABLE 2-continued

| Table 2 below provides exemplary primers which may be used to amplify or sequence MVPs defined in Table 1 above. | | |
|---|---|---|
| 7 | GGTGATGAGGTTGATGTAGTGT | 573 |
| 7 | AATTATTTTTAAAGTGGGGGTAGTAT | 574 |
| 5 | ggAGGGATAGGAGYGAGAGGG | 575 |
| 2 | ACCCAAAACTCAATCTTACTTCT | 576 |
| 4 | ATAAATCTAATAAATAATTTTCCCCACC | 577 |
| 20 | CCCCAAACCCAAAATAAACTTC | 578 |
| 1 | CACCTACCAAATTTACAAATCCC | 579 |
| 7 | CCCRAAACCCCACACATACTT | 580 |
| 2 | TTTGGGTGGAGGTTATGGA | 581 |
| 15 | AACAACCRAACCCACCAAAAA | 582 |
| 15 | ACACTCRACACACTTAAAACAAAC | 583 |
| 3 | GAAGGAGAGGGGTTGGG | 584 |
| 5 | GGTTTGTAGTTTTGGTTATAGTTGT | 585 |
| 7 | GAAGGTAGAGAATTTGGGTTTTT | 586 |
| 14 | TTGAGTGTGTTAGGYGTTTGTTG | 587 |
| 2 | RCTCCAATAACCCAACCTAA | 588 |
| 20 | CCTATTTCTACCCCCACCC | 589 |
| 8 | CCCTTCTCRATCAAAAACATCCTAC | 590 |
| 16 | AATCAACRACTTAAACATTCAAATTAAACT | 591 |
| 13 | GTTGYGTTTGTTAGTGTAGGAAGTT | 592 |
| 2 | GGAAAATTGGAGGTAGGGG | 593 |
| 7 | GGAGTGATTTATGYGTTATTGTTTTGT | 594 |
| 22 | AAACTACACCCRAAAACCTCTAAAT | 595 |
| 22 | GAGGTTTTTATAGGGTAGGATTAGT | 596 |
| 22 | AACAACAACTAATCCRAACTAATAAAAAC | 597 |
| 1 | AAAACCACCTACTAAAACCRAAAATAA | 598 |
| 6 | GGGTAAAGAAGAGGAGAAGATAAA | 599 |
| 1 | RCCAAACCCAAACAAAACA | 600 |
| 2 | ATTCCCAATAACATATTCATTTACAAAA | 601 |
| 7 | CATAAATCAAACCRCAAAAATCTCCAATA | 602 |
| 2 | CCTCCTCCCRCATAAAAATATCAAAATAA | 603 |
| 1 | ACTACAACTACTCTACRACACTACC | 604 |
| 5 | ggAGGGGTYGTTTTAGGGGG | 605 |
| 7 | ACTAAAACCCRCACCTAACCCA | 606 |
| 14 | GTTTGGGTGATAATAGGGAAAATTA | 607 |
| 10 | CTAACCATAACTAACCTACCCC | 608 |
| 3 | CCTTCAAAACCAAATACAAACTTAT | 609 |
| 11 | aaagaagaagaagaagaagaagaTTAG | 610 |

TABLE 2-continued

| Table 2 below provides exemplary primers which may be used to amplify or sequence MVPs defined in Table 1 above. | | |
|---|---|---|
| 10 | YGTTGATTATGGTTGGTTTGT | 611 |
| 11 | GATAGGGATTTYGGGGATAGGG | 612 |
| 11 | CTACAAATAAAACTTCTTTCCAAATAAAC | 613 |
| 5 | GAGTYGGGTAGGTTTTTGGGTT | 614 |
| 2 | GAAGATGTTAGGGTAGYGAGTTTTG | 615 |
| 14 | CAAAACAATAATTTCTCAACTTTTCC | 616 |
| 1 | AATACAACATAAAAACTCTTTCRCTAACAC | 617 |
| 11 | ACTCCCTCCCTTCTATTTTCA | 618 |
| 4 | AATACAAACAAAACAATCCCTCCAC | 619 |
| 7 | ACTTTTACTATAAAAATTATAACTACAAAACATC | 620 |
| 19 | ATCAAACTATCCCTAACCRAAATTCTA | 621 |
| 5 | TGAAGTAATGAGATGAAAAGTATAAGAG | 622 |
| 2 | RAAAACTTAAACCAATCCAAC | 623 |
| 15 | TGGTTGTGGAGGAGTTGAG | 624 |
| 5 | TTTTGTGTGGGAGTTGGTT | 625 |
| 14 | ACATATTTACTACATTTCCRACCTAAAC | 626 |
| 10 | GGTTTTTAGGAGTTTTGTTTTTAGAT | 627 |
| 19 | GGAGGAGATGTTGTTTTTAGTG | 628 |
| 6 | GTTGTTAAATAAAAAGTYGGGGTGAG | 629 |
| 20 | ACTTTTTATCTCTTACAAACRTCTCCTAAAC | 630 |
| 7 | GGGTAGTAGTGTGTGTAGGG | 631 |
| 5 | ACCTACAACCCTAACTACAACTA | 632 |
| 7 | CAACTCCTCRAAATACCCAATACA | 633 |
| 14 | CAACCCCAAAACCAACAAAT | 634 |
| 20 | TTTTTAGYGGGATAGGGTGTTGG | 635 |
| 18 | GTTAGGAGGGATTYGGGAGGT | 636 |
| 11 | AAACCCTTCCCAACCCT | 637 |
| 9 | ACTCCATCAACRACATCCTAAACA | 638 |
| 1 | yggtgttaggttgtgggt | 639 |
| 18 | GGAGGGGTGGGATAGGA | 640 |
| 1 | TGGTTGTAATAGGYGGTGGGT | 641 |
| 7 | TGGGTATGYGGGTGTTTTAGGA | 642 |
| 11 | CATCCRCTAACCAATAAACTTCCTTAAA | 643 |
| 7 | CTCCCACCCCTAAACAAAC | 644 |
| X | GTGGGTGTGGGAGGTTT | 645 |
| 1 | rataccaaactataaacaaaccc | 646 |
| 7 | CCCCTATACCTCTATCTCTACC | 647 |
| 2 | GTGTTGTGGGGGTTTTGG | 648 |
| 2 | GGGTGTTAAGATAAGATATGTTTAGT | 649 |

TABLE 2-continued

Table 2 below provides exemplary primers which may be used to amplify or sequence MVPs defined in Table 1 above.

| | | |
|---|---|---|
| 11 | ACCAAACCCTAAAACAACAAAT | 650 |
| 14 | GGGTTAAATAGAAGAAATGTTTTTAATG | 651 |
| 1 | RCTAATTCCTAACAACTAAACCAAC | 652 |
| 17 | GTTTTTGGGGAGGGGGAA | 653 |
| 8 | ACCCCTATCCCCAAATCTAC | 654 |
| 17 | TCCCTCRACTTTAACCAACTCA | 655 |
| 2 | GTGGAGGAGAGGGGAAG | 656 |
| 13 | YGTGGGGTTGAGTTTTAGTT | 657 |

Table 3 below provides statistical information of exemplary assays involving all 150 MVPs as defined in Table 1 above, the top 3 ranked MVPs (SEQ ID NOs:1-3), the top 5 ranked MVPs (SEQ ID NOs:1-5) and the top 10 ranked MVPs (SEQ ID NOs:1-10).

TABLE 3

| | All 150 | Top 3 | Top 5 | Top 10 |
|---|---|---|---|---|
| Sensitivity | 0.93 | 0.61 | 0.66 | 0.70 |
| Specificity | 0.97 | 0.71 | 0.74 | 0.80 |
| PPV | 0.98 | 0.79 | 0.82 | 0.86 |
| NPV | 0.89 | 0.51 | 0.55 | 0.61 |
| AUC | 0.95 | 0.66 | 0.70 | 0.75 |

REFERENCES

1. Siegel R, Ward E, Brawley O, Jemal A: Cancer statistics, 2011: the impact of eliminating socioeconomic and racial disparities on premature cancer deaths. *CA Cancer J Clin* 2011, 61:212-236.
2. Jemal A, Siegel R, Ward E, Hao Y, Xu J, Thun M J: Cancer statistics, 2009. *CA Cancer J Clin* 2009, 59:225-249.
3. Khadra M H, Pickard R S, Charlton M, Powell P H, Neal D E: A prospective analysis of 1,930 patients with hematuria to evaluate current diagnostic practice. *J Urol* 2000, 163:524-527.
4. Cha E K, Tirsar L A, Schwentner C, Hennenlotter J, Christos P J, Stenzl A, Mian C, Martini T, Pycha A, Shariat S F, Schmitz-Drager B J: Accurate risk assessment of patients with asymptomatic hematuria for the presence of bladder cancer. *World J Urol* 2012, 30:847-852.
5. Lyratzopoulos G, Abel G A, McPhail S, Neal R D, Rubin G P: Gender inequalities in the promptness of diagnosis of bladder and renal cancer after symptomatic presentation: evidence from secondary analysis of an English primary care audit survey. *BMJ Open* 2013, 3.
6. Burke D M, Shackley D C, O'Reilly P H: The community-based morbidity of flexible cystoscopy. *BJU Int* 2002, 89:347-349.
7. Denzinger S, Burger M, Walter B, Knuechel R, Roessler W, Wieland W F, Filbeck T: Clinically relevant reduction in risk of recurrence of superficial bladder cancer using 5-aminolevulinic acid-induced fluorescence diagnosis: 8-year results of prospective randomized study. *Urology* 2007, 69:675-679.
8. Zaak D, Kriegmair M, Stepp H, Stepp H, Baumgartner R, Oberneder R, Schneede P, Corvin S, Frimberger D, Knuchel R, Hofstetter A: Endoscopic detection of transitional cell carcinoma with 5-aminolevulinic acid: results of 1012 fluorescence endoscopies. *Urology* 2001, 57:690-694.
9. Schlake A, Crispen P L, Cap A P, Atkinson T, Davenport D, Preston D M: NMP-22, urinary cytology, and cystoscopy: a 1 year comparison study. *Can J Urol* 2012, 19:6345-6350.
10. Burns M B, Lackey L, Carpenter M A, Rathore A, Land A M, Leonard B, Refsland E W, Kotandeniya D, Tretyakova N, Nikas J B, et al: APOBEC3B is an enzymatic source of mutation in breast cancer. *Nature* 2013, 494:366-370.
11. Kelly J D, Fawcett D P, Goldberg L C: Assessment and management of nonvisible haematuria in primary care. *BMJ* 2009, 338:a3021.
12. Lotan Y, Roehrborn C G: Sensitivity and specificity of commonly available bladder tumor markers versus cytology: results of a comprehensive literature review and meta-analyses. *Urology* 2003, 61:109-118; discussion 118.
13. van Rhijn B W, van der Poel H G, van der Kwast T H: Urine markers for bladder cancer surveillance: a systematic review. *Eur Urol* 2005, 47:736-748.
14. Tilki D, Burger M, Dalbagni G, Grossman H B, Hakenberg O W, Palou J, Reich O, Roupret M, Shariat S F, Zlotta A R: Urine markers for detection and surveillance of non-muscle-invasive bladder cancer. *Eur Urol* 2011, 60:484-492.
15. Beukers W, Hercegovac A, Vermeij M, Kandimalla R, Blok A C, van der Aa M M, Zwarthoff E C, Zuiverloon T C: Hypermethylation of the polycomb group target gene PCDH7 in bladder tumors from patients of all ages. *J Urol* 2013, 190:311-316.
16. Hogue M O, Kim M S, Ostrow K L, Liu J, Wisman G B, Park H L, Poeta M L, Jeronimo C, Henrique R, Lendvai A, et al: Genome-wide promoter analysis uncovers portions of the cancer methylome. *Cancer Res* 2008, 68:2661-2670.
17. Kandimalla R, van Tilborg A A, Zwarthoff E C: DNA methylation-based biomarkers in bladder cancer. *Nat Rev Urol* 2013.
18. Kandimalla R, Masius R, Beukers W, Bangma C H, Orntoft T F, Dyrskjot L, van Leeuwen N, Lingsma H, van Tilborg A A, Zwarthoff E C: A 3-plex methylation assay combined with the FGFR3 mutation assay sensitively detects recurrent bladder cancer in voided urine. *Clin Cancer Res* 2013, 19:4760-4769.
19. Yu J, Zhu T, Wang Z, Zhang H, Qian Z, Xu H, Gao B, Wang W, Gu L, Meng J, et al: A novel set of DNA methylation markers in urine sediments for sensitive/specific detection of bladder cancer. *Clin Cancer Res* 2007, 13:7296-7304.
20. Friedrich M G, Weisenberger D J, Cheng J C, Chandrasoma S, Siegmund K D, Gonzalgo 438 M L, Toma M I, Huland H, Yoo C, Tsai Y C, et al: Detection of methylated apoptosis-associated genes in urine sediments of bladder cancer patients. *Clin Cancer Res* 440 2004, 10:7457-7465.
21. Hogue M O, Begum S, Topaloglu O, Chatterjee A, Rosenbaum E, Van Criekinge W, Westra W H, Schoenberg M, Zahurak M, Goodman S N, Sidransky D: Quantitation of promoter methylation of multiple genes in urine DNA and bladder cancer detection. *J Natl Cancer Inst* 2006, 98:996-1004.
22. Su S F, de Castro Abreu A L, Chihara Y, Tsai Y, Andreu-Vieyra C, Daneshmand S, Skinner E C, Jones P A, Siegmund K D, Liang G: A panel of three markers hyper- and hypomethylated in urine sediments accurately predicts bladder cancer recurrence. *Clin Cancer Res* 2014, 20:1978-1989.
23. Andersson E, Steven K, Guldberg P: Size-based enrichment of exfoliated tumor cells in urine increases the sensitivity for DNA-based detection of bladder cancer. *PLoS One* 2014, 9:e94023.
24. Fackler M J, Lopez Bujanda Z, Umbricht C, Teo W W, Cho S, Zhang Z, Visvanathan K, Jeter S, Argani P, Wang C, et al: Novel methylated biomarkers and a robust assay to detect circulating tumor DNA in metastatic breast cancer. *Cancer Res* 2014, 74:2160-2170.
25. Philipp A B, Stieber P, Nagel D, Neumann J, Spelsberg F, Jung A, Lamerz R, Herbst A, Kolligs F T: Prognostic role of methylated free circulating DNA in colorectal cancer. *Int J Cancer* 2012, 131:2308-2319.
26. Campan M, Moffitt M, Houshdaran S, Shen H, Widschwendter M, Daxenbichler G, Long T, Marth C, Laird-Offringa I A, Press M F, et al: Genome-scale screen for DNA methylation-based detection markers for ovarian cancer. *PLoS One* 2011, 6:e28141.
27. Leng S, Do K, Yingling C M, Picchi M A, Wolf H J, Kennedy T C, Feser W J, Baron A E, Franklin W A, Brock M V, et al: Defining a gene promoter methylation signature in sputum for lung cancer risk assessment. *Clin Cancer Res* 2012, 18:3387-3395.
28. Belinsky S A: Gene-promoter hypermethylation as a biomarker in lung cancer. *Nat Rev Cancer* 2004, 4:707-717.
29. Kulis M, Esteller M: DNA methylation and cancer. *Adv Genet* 2010, 70:27-56. 469
30. Tewhey R, Warner J B, Nakano M, Libby B, Medkova M, David P H, Kotsopoulos S K, Samuels M L, Hutchison J B, Larson J W, et al: Microdroplet-based PCR enrichment for large-scale targeted sequencing. *Nat Biotechnol* 2009, 27:1025-1031.
31. Paul D S, Guilhamon P, Karpathakis A, Butcher L M, Thirlwell C, Feber A, Beck S: Assessment of RainDrop BS-seq as a method for large-scale, targeted bisulfite sequencing. *Epigenetics* 2014, 9.
32. Guilhamon P, Eskandarpour M, Halai D, Wilson G A, Feber A, Teschendorff A E, Gomez V, Hergovich A, Tirabosco R, Fernanda Amary M, et al: Meta-analysis of IDH-mutant cancers identifies EBF1 as an interaction partner for TET2. *Nat Commun* 2013, 4:2166.
33. Komori H K, LaMere S A, Torkamani A, Hart G T, Kotsopoulos S, Warner J, Samuels M L, Olson J, Head S R, Ordoukhanian P, et al: Application of microdroplet PCR for large-scale targeted bisulfite sequencing. *Genome Res* 2011, 21:1738-1745.
34. Lowe R, Rakyan V K: Marmal-aid—a database for Infinium HumanMethylation450. *BMC Bioinformatics* 2013, 14:359.
35. R: A language and environment for statistical computing. 485
36. Morris T J, Butcher L M, Feber A, Teschendorff A E, Chakravarthy A R, Wojdacz T K, Beck S: ChAMP: 450 k Chip Analysis Methylation Pipeline. *Bioinformatics* 2013.
37. Teschendorff A E, Marabita F, Lechner M, Bartlett T, Tegner J, Gomez-Cabrero D, 488 Beck S: A beta-mixture quantile normalization method for correcting probe design bias in Illumina Infinium 450 k DNA methylation data. *Bioinformatics* 2013, 29:189-196.
38. Morris T J, Butcher L M, Feber A, Teschendorff A E, Chakravarthy A R, Wojdacz T K, Beck S: ChAMP: 450 k Chip Analysis Methylation Pipeline. *Bioinformatics* 2014, 30:428-430.
39. Butcher L M, Beck S: Probe Lasso: A novel method to rope in differentially methylated regions with 450K DNA methylation data. *Methods* 2015, 72:21-28.
40. Deaton A M, Webb S, Kerr A R, Illingworth R S, Guy J, Andrews R, Bird A: Cell type-specific DNA methylation at intragenic CpG islands in the immune system. *Genome Res* 2011, 21:1074-1086.
41. Hajdinjak T: UroVysion FISH test for detecting urothelial cancers: meta-analysis of diagnostic accuracy and comparison with urinary cytology testing. *Urol Oncol* 2008, 26:646-651.
42. Gerlinger M, Catto J W, Orntoft T F, Real F X, Zwarthoff E C, Swanton C: Intratumour Heterogeneity in Urologic Cancers: From Molecular Evidence to Clinical Implications. *Eur Urol* 2014.
43. Hoffmann A C, Wild P, Leicht C, Bertz S, Danenberg K D, Danenberg P V, Stohr R, Stockle M, Lehmann J, Schuler M, Hartmann A: MDR1 and ERCC1 expression predict outcome of patients with locally advanced bladder cancer receiving adjuvant chemotherapy. *Neoplasia* 2010, 12:628-636.
44. Venkatesan A, Chu P, Kerlikowske K, Sickles E A, Smith-Bindman R: Positive predictive value of specific mammographic findings according to reader and patient variables. *Radiology* 2009, 250:648-657.
45. Mandel J S, Church T R, Bond J H, Ederer F, Geisser M S, Mongin S J, Snover D C, Schuman L M: The effect of fecal occult-blood screening on the incidence of colorectal cancer. *N Engl J Med* 2000, 343:1603-1607.
46. Hoffman R M, Gilliland F D, Adams-Cameron M, Hunt W C, Key C R: Prostate-specific antigen testing accuracy in community practice. *BMC Fam Pract* 2002, 3:19.
47. Chung W, Bondaruk J, Jelinek J, Lotan Y, Liang S, Czerniak B, Issa J P: Detection of bladder cancer using novel DNA methylation biomarkers in urine sediments. *Cancer Epidemiol Biomarkers Prev* 2011, 20:1483-1491.
48. Catalona W J, Smith D S, Ratliff T L, Dodds K M, Coplen D E, Yuan J J, Petros J A, Andriole G L: Measurement of prostate-specific antigen in serum as a screening test for prostate cancer. *N Engl J Med* 1991, 324:1156-1161.
49. Blick C G, Nazir S A, Mallett S, Turney B W, Onwu N N, Roberts I S, Crew J P, Cowan N C: Evaluation of diagnostic strategies for bladder cancer using computed tomography (CT) urography, flexible cystoscopy and voided urine cytology: results for 778 patients from a hospital haematuria clinic. *BJU Int* 2012, 110:84-94.

50. Wolff E M, Chihara Y, Pan F, Weisenberger D J, Siegmund K D, Sugano K, Kawashima K, Laird P W, Jones P A, Liang G: Unique DNA methylation patterns distinguish noninvasive and invasive urothelial cancers and establish an epigenetic field defect in premalignant tissue. *Cancer Res* 2010, 70:8169-8178.
51. Olkhov-Mitsel, E and Bapat, B: Strategies for discovery and validation of methylated and hydroxymethylated DNA biomarkers. *Cancer Medicine* 2012, 1(2): 237-260.
52. Eng, J: Receiver Operating Characteristic Analysis: A Primer. *Academic Radiology* 2005, 12(7): 909-916.
53. Herman, J. G., Graff, J. R., Myohanen, S., Nelkin, B. D. & Baylin, S. B.: Methylation-specific PCR: a novel PCR assay for methylation status of CpG islands. *Proc. Natl Acad. Sci. USA* 1996, 93: 9821-9826.
54. Frommer, M. et al.: A genomic sequencing protocol that yields a positive display of 5-methylcytosine residues in individual DNA strands. *Proc. Natl Acad. Sci. USA* 1992, 89: 1827-1831.
55. Xiong, Z. & Laird, P. W.: COBRA: a sensitive and quantitative DNA methylation assay. *Nucleic Acids Res.* 1997, 25: 2532-2534.
56. Gonzalgo, M. L. & Jones, P. A.: Rapid quantitation of methylation differences at specific sites using methylationsensitive single nucleotide primer extension (Ms-SNuPE). *Nucleic Acids Res.* 1997, 25: 2529-2531.
57. Singal, R. & Grimes, S. R.: Microsoft Word macro for analysis of cytosine methylation by the bisulfite deamination reaction. *Biotechniques* 2001, 30: 116-120.
58. Anbazhagan, R., Herman, J. G., Enika, K. & Gabrielson, E.: Spreadsheet-based program for the analysis of DNA methylation. *Biotechniques* 2001, 30: 110-114.
59. Li, L. C. & Dahiya, R.: MethPrimer: designing primers for methylation PCRs. *Bioinformatics* 2002, 18: 1427-1431.
60. Aronesty, E.: Comparison of Sequencing Utility Programs. The Open *Bioinformatics Journal,* 2013, 7: 1-8.
61. Krueger, F. & Andrews, S. R.: Bismark: a flexible aligner and methylation caller for Bisulfite-Seq applications. *Bioinformatics,* 2011, 27(11):1571-2.

The invention claimed is:

1. A method, comprising measuring from a biological sample from an individual the methylation status in each one of a group of Methylation Variable Positions (MVPs) selected from a panel comprising the MVPs identified in SEQ ID NOS 1 to 150 and denoted by [CG], wherein the group comprises at least 25 of the MVPs identified in SEQ ID NOS 1 to 150 and denoted by [CG], wherein the measuring identifies the presence of methylation in the [CG] of each of SEQ ID NOs 1 to 3.

2. The method of claim 1, wherein the group of MVPs comprises at least 40 of the MVPs identified in SEQ ID NOS 1 to 150 and denoted by [CG].

3. The method of claim 1, wherein the group of MVPs comprises at least 50 of the MVPs identified in SEQ ID NOS 1 to 150 and denoted by [CG].

4. The method of claim 1, wherein the group of MVPs comprises at least 100 of the MVPs identified in SEQ ID NOS 1 to 150 and denoted by [CG].

5. The method of claim 1, wherein the group of MVPs comprises all of the MVPs identified in SEQ ID NOS 1 to 150 and denoted by [CG].

6. The method of claim 1, wherein the MVPs determined to be methylated include the MVPs identified in SEQ ID NOS 1 to 3 and denoted by [CG], or include the MVPs identified in SEQ ID NOS 1 to 5 and denoted by [CG], or include the MVPs identified in SEQ ID NOS 1 to 10 and denoted by [CG], or include the MVPs identified in SEQ ID NOS 1 to 40 and denoted by [CG].

7. The method of claim 1, wherein a treatment for bladder cancer is administered to the individual when at least 25 of the MVPs of the group are methylated.

8. The method of claim 1, wherein a treatment for bladder cancer is administered to the individual when at least 40 of the MVPs of the group are methylated.

9. The method of claim 1, wherein a treatment for bladder cancer is administered to the individual when at least 50 of the MVPs of the group are methylated.

10. The method of claim 1, wherein a treatment for bladder cancer is administered to the individual when all of the MVPs of the group are methylated.

11. The method of claim 1, wherein a biological sample obtained from the individual is a sample of urine, blood, serum, plasma or cell-free DNA.

12. The method of claim 1, wherein the measuring step comprises bisulphite treatment of DNA from the sample, amplification of the group of MVPs using methylation specific PCR primers, sequencing, and/or using methylation-discriminatory microarrays.

13. A method of analyzing urine or a bladder sample from a patient, comprising the steps of:

assaying from the urine or bladder sample the methylation status of each one of a group of Methylation Variable Positions (MVPs) selected from a panel comprising the MVPs identified in SEQ ID NOS 1 to 150 and denoted by [CG], wherein the group comprises at least 25 of the MVPs identified in SEQ ID NOS 1 to 150 and denoted by [CG], wherein the assaying identifies the presence of methylation in the [CG] of each of SEQ ID NOs 1 to 3.

14. A method of treating a patient for bladder cancer comprising administering bladder cancer therapy to a patient after being determined to have at least 25 Methylation Variable Positions (MVPs) methylated, wherein the MVPs are selected from a panel comprising the MVPs identified in SEQ ID NOS 1 to 150 and denoted by [CG], and after being determined to have methylation in the [CG] of each of SEQ ID NOs 1 to 3.

15. The method of claim 14, wherein bladder cancer therapy is administered to a patient after being determined to have at least 40 MVPs methylated.

16. The method of claim 14, wherein bladder cancer therapy is administered to a patient after being determined to have at least 50 MVPs methylated.

17. The method of claim 14, wherein bladder cancer therapy is administered to a patient after being determined to have all of the MVPs methylated.

18. The method of claim 14, wherein the cancer is non-muscle invasive bladder cancer (NMIBC) or muscle invasive bladder cancer (MIBC).

19. A method, comprising measuring the presence of methylation in the Methylation Variable Positions MVPs identified in [CG] of each of SEQ ID NOs 1 to 3 in DNA from a urine sample from an individual, said presence of methylation relative to a non-cancer control, wherein the measuring identifies the presence of methylation in the [CG] of each of SEQ ID NOs 1 to 3.

20. The method of claim 19, further comprising measuring from the urine sample the methylation status in each one of a group of MVPs selected from a panel comprising the MVPs identified in SEQ ID NOS 1 to 150 and denoted by [CG], wherein the group comprises at least 25 of the MVPs identified in SEQ ID NOS 1 to 150 and denoted by [CG].

* * * * *